US009872899B2

(12) United States Patent
Tobin et al.

(10) Patent No.: US 9,872,899 B2
(45) Date of Patent: Jan. 23, 2018

(54) IMMUNOGENIC HUMAN RHINOVIRUS (HRV) COMPOSITIONS

(71) Applicant: Biological Mimetics, Inc., Frederick, MD (US)

(72) Inventors: Gregory J Tobin, Frederick, MD (US); Peter L Nara, Frederick, MD (US)

(73) Assignee: Biological Mimetics, Inc., Frederick, MD (US)

( * ) Notice: Subject to any disclaimer, the term of this patent is extended or adjusted under 35 U.S.C. 154(b) by 0 days.

(21) Appl. No.: 14/774,924

(22) PCT Filed: Mar. 15, 2014

(86) PCT No.: PCT/US2014/029891
§ 371 (c)(1),
(2) Date: Sep. 11, 2015

(87) PCT Pub. No.: WO2014/145174
PCT Pub. Date: Sep. 18, 2014

(65) Prior Publication Data
US 2016/0022804 A1    Jan. 28, 2016

Related U.S. Application Data

(60) Provisional application No. 61/793,788, filed on Mar. 15, 2013.

(51) Int. Cl.
*A61K 39/12*     (2006.01)
*A61K 39/125*    (2006.01)
*C07K 14/095*    (2006.01)
*C07K 14/005*    (2006.01)
*C07K 16/10*     (2006.01)
*A61K 39/00*     (2006.01)

(52) U.S. Cl.
CPC ............ *A61K 39/125* (2013.01); *A61K 39/12* (2013.01); *C07K 14/005* (2013.01); *C07K 14/095* (2013.01); *C07K 16/1009* (2013.01); A61K 2039/5258 (2013.01); A61K 2039/58 (2013.01); C07K 2317/33 (2013.01); C07K 2317/76 (2013.01); C07K 2319/00 (2013.01); C12N 2770/32722 (2013.01); C12N 2770/32723 (2013.01); C12N 2770/32734 (2013.01)

(58) Field of Classification Search
None
See application file for complete search history.

(56) References Cited

U.S. PATENT DOCUMENTS 8,652,486 B2      2/2014  Kalnin et al.
2010/0239605 A1*  9/2010  Kalnin ................ A61K 39/145
                                                424/199.1
2014/0161833 A1   6/2014  Kalnin et al.

OTHER PUBLICATIONS

Katpally et al. Antibodies to the Buried N Terminus of Rhinovirus VP4 Exhibit Cross-Serotypic Neutralization. J Virol. Jul. 2009;83(14):7040-8. Epub Apr. 29, 2009.*
Tobin et al. Deceptive imprinting and immune refocusing in vaccine design. Vaccine 26 (2008) 6189-6199.*
GenBank CAG08266.
Katpally et al., "Antibodies . . . Neutralization?" J Virol 83:7040-7048, 2009.

* cited by examiner

*Primary Examiner* — Nianxiang Zou
(74) *Attorney, Agent, or Firm* — MDIP LLC

(57) ABSTRACT

Novel compositions useful as human rhinovirus immunogens are provided. The compositions enable a host response to sites normally not recognized by a host.

10 Claims, 11 Drawing Sheets

Figure 1

```
        VP2       C epitope    C              B       B epitope
HRV2   139  TWSS(42 a.a.)KFH(16 a.a.)ALHGNVNVGYNY 215(SEQ ID NO:1)
HRV39  139  VWKR(42 a.a.)KFH(16 a.a.)ANYGNVTAGYNY 215(SEQ ID NO:2)

VP2                B epitope
HRV2   217  HPGETGREVKAETRLNPDLQPTEEYWLNFDGT-248(SEQ ID NO:3)
HRV39  217  HPGEAGRDV-GQQRTNNEKQPSDDNWLNFDGT-247(SEQ ID NO:4)

C epitope
HRV2   297  ICPLETSSAINTIPITISIS-316 (SEQ ID NO:5)
HRV39  297  SPLDADTSATAIVPITVSIS-316 (SEQ ID NO:6)

VP3      B epitope
HRV2   284  PINNTDTYINS 394 (SEQ ID NO:7)
HRV39  288  PINNTNERIGN 398 (SEQ ID NO:8)

VP1        A epitope
HRV2   647  SKLEVTLANYNKENFTVW 664 (SEQ ID NO:9)
HRV39  652  STITMKKENYNEHNFVDW 669 (SEQ ID NO:10)

A epitope
HRV2   788  TEKHIRKVHIMTR 801 (SEQ ID NO:11)
HRV39  795  TNQQEHLVEVTTR 808 (SEQ ID NO:12)

B epitope
HRV2   819  ALEYTRAHRTNFKIEDRSIQTAIVTRPIITT 849 (SEQ ID NO 13)
HRV39  826  AVFYTHSNVTNYKVRDGEPTLFIKPRESLTT 856 (SEQ ID NO 14)
```

Figure 4

```
Examples of Mutations to Antigenic Sites of HRV39

←     A Epitope     →
     ITMKKENYNEHN QQEHLVEV    (SEQ ID NO:15)
M1---LI------- --------      (SEQ ID NO:16)
M2-----------A --------      (SEQ ID NO:17)
M3-----Q----Q- --------      (SEQ ID NO:18)
M4------------ --A---Q-      (SEQ ID NO:19)
M5---LI------A --------      (SEQ ID NO:20)
M6------------ --A---Q-      (SEQ ID NO:21)

←            B Epitope                    →
       QRTNNEKQPP INNTNERIGNY KVRDGEPTLF IKPRESLTT  (SEQ ID NO:62)
M7     ---LI----- ----------- ----------- ---------- (SEQ ID NO:22)
M8     ---------- -----A----- ----------- ----Q---- (SEQ ID NO:23)
M9     ---------- ----------- A-----A--- ---------- (SEQ ID NO:24)
M10    -I---Q---- -------A--- ----------- ---------- (SEQ ID NO:25)
M11    ---------- ----------- --I-------- --L-I---- (SEQ ID NO:26)
M12    ---LI----- -----A----- A-----A--- ----Q---- (SEQ ID NO:27)
M13    -I---Q---- -------A--- --I-------- --L-I---- (SEQ ID NO:28)

← C Epitope →
       WKRD ETSSAINTI     (SEQ ID NO:63)
M14    ---- ----G-L--(SEQ ID NO:29)
M15    -AG- ---------(SEQ ID NO:30)
M16    -AG- ----G-L--(SEQ ID NO:31)

M17 = M5 + M12 + M14 (SEQ ID NO:32)
M18 = M6 + M13 + M15 (SEQ ID NO 33)
```

Figure 5

| HRV Serotypes Analyzed ||
| --- | --- |
| HRV-A | HRV-B |
| 1A, 1B, 2, 8, 9, 10, 11, 12, 13, 15, 16, 19, 20, 21, 22, 23, 25, 28, 30, 31, 38, 39, 43, 45, 46, 47, 49, 50, 51, 55, 56, 58, 59, 60, 61, 66, 73, 81, 85, 88, 89, 90, 98 | 3, 4, 5, 6, 14, 17, 26, 35, 52, 69, 79, 83, 84, 86, 91, 93, 97, 99 |

Figure 7

List of HRV Serotypes Neutralized by HRV39 IRT Sera >4-fold Better Than
Non-immune Sera
Statistical Analysis of Graded CPE Screening Data

| Student's T Test | 39WT | 39M4 | 39M5 | 39M9 | 39M10 | 39M16 |
|---|---|---|---|---|---|---|
| p<0.05 | 39 | 1A, 1B, 2, 4, 8, 9, 11, 13, 16, 17, 20, 21, 23, 30, 38, 39, 43, 45, 47, 49, 51, 52, 55, 58, 60, 69, 73, 79, 81, 83, 85, 86, 89, 93, 99 | 1A, 1B, 3, 4, 5, 6, 8, 11, 13, 15, 16, 17, 20, 21, 23, 28, 30, 38, 39, 43, 45, 46, 47, 49, 50, 51, 52, 58, 60, 69, 73, 79, 81, 83, 85, 86, 89, 93, 97, 98, 99 | 1B, 2, 3, 4, 5, 6, 8, 10, 11, 13, 16, 17, 20, 21, 30, 31, 39, 43, 45, 47, 49, 52, 55, 58, 61, 69, 73, 79, 81, 83, 85, 86, 89, 93, 97, 98, 99 | 1B, 3, 4, 5, 6, 8, 12, 13, 16, 17, 20, 21, 25, 30, 39, 43, 45, 46, 47, 49, 52, 56, 58, 60, 69, 73, 79, 81, 83, 85, 86, 93, 97, 98, 99 | 1B, 3, 4, 12, 13, 16, 17, 19, 20, 21, 23, 25, 30, 39, 43, 45, 46, 47, 49, 52, 55, 58, 60, 69, 73, 79, 81, 83, 85, 86, 91, 93, 97, 98, 99 |
| Totals | 1 | 35 | 41 | 37 | 36 | 35 |

Note: HRV39 is an HRV-A virus. HRV-B serotypes neutralized are designated by underlined numbers.

Figure 8

```
          M6 A epitope 650
WT       SVLDIVDNYNDQSFTKWKI (SEQ ID NO:34)
IRT      SVLAIVANYNGASFTAWKI (SEQ ID NO:35)

M7 A epitope 790
WT       SRIVTSEQLH KVKVVTRIYH (SEQ ID NO:36)
IRT      SRIVTAGALH AVAVVTRIYH (SEQ ID NO:37)

M2 B epitope 220
WT       GREVGTQV--ENEKQPSDDNW (SEQ ID NO:38)
IRT      GAQVGTQV--QNQAQPSDDNW (SEQ ID NO:39)

M5 390
WT       TQSNIGNVSM (SEQ ID NO:40)
IRT      TASAIGNVSM (SEQ ID NO:41)

M8    830         M9 850
WT       THTTNYKLSSEVHNDVAIRPR (SEQ ID NO:42)
IRT      THTTNYALSVQVHNDVAIAPA (SEQ ID NO:43)

M1  C epitope 130
WT       FYTLDSKMWN STSKGWWWKL (SEQ ID NO:44)
IRT      FYTLDSKMWA GTSAGWWWKL (SEQ ID NO:45)

M3   C epitope 290
WT       VIIPVCQLQSNNISNIVPI (SEQ ID NO:46)
IRT      VIIPVCQLASNAISAIVPI (SEQ ID NO:47)

M4 variable 330
WT       FSGARAKT (SEQ ID NO:48)
IRT      FSGAVALT (SEQ ID NO:49)
```

Figure 9

List of HRV Serotypes Neutralized by HRV16 IRT Sera >4-fold Better than
Non-immune Sera
Statistical Analysis of Graded CPE Screening Data

| Student's T Test | 16WT | 16M1 | 16M2 | 16M3 | 16M5 | 16M8 |
|---|---|---|---|---|---|---|
| $p < 0.05$ | 16 | 1A, 1B, 8, 9, 10, 11, 16, 19, 21, 23, 25, 38, 39, 46, 50, 59, 66, 73, 90, 91 | 1A, 1B, 8, 9, 10, 11, 12, 13, 16, 19, 21, 23, 25, 28, 38, 39, 45, 46, 47, 50, 55, 56, 58, 59, 60, 61, 66, 73, 81, 90 | 1A, 1B, 8, 9, 10, 11, 13, 15, 16, 19, 20, 21, 22, 23, 25, 28, 38, 39, 43, 45, 46, 50, 51, 55, 56, 59, 60, 61, 66, 73, 81, 89, 90, 97 | 1A, 1B, 8, 10, 11, 12, 13, 16, 19, 20, 21, 22, 23, 25, 28, 35, 38, 39, 45, 46, 50, 55, 58, 59, 60, 66, 73, 81, 85, 89 | 1A, 1B, 8, 9, 11, 13, 15, 16, 21, 23, 25, 30, 35, 38, 39, 43, 45, 46, 49, 55, 56, 61, 66, 73, 81, 89, 90 |
| Totals | 1 | 20 | 30 | 34 | 30 | 26 |

Note: HRV26 is an HRV-A virus. HRV-B serotypes neutralized are designated by underlined numbers.

Figure 10

```
A. VP1       90           VP2 120
WT:   DATGI  DNHREAKLFN       IPEHQLASHE  SEQ ID NO:50
A5:   -----  ----------       ----------  SEQ ID NO:51
B5:   -----  ----d-----       ----------  SEQ ID NO:52
C5:   -----  n---------       ----------  SEQ ID NO:53
D5:   -----  ----------       ----------  SEQ ID NO:54

B. VP1       90           VP2 120
WT:   DATGI  DNHREAKLFN       IPEHQLASHE  SEQ ID NO:55
B4-1  -----  ----a-----       t---hhnq--  SEQ ID NO:56
B4-2  -----  n---------       ----------  SEQ ID NO:57
B4-3  -----  n---------       t---h-tq--  SEQ ID NO:58
B4-4  -----  g---------       t---h-nq--  SEQ ID NO:59
B5-6  -----  g---------       ----h-tq--  SEQ ID NO:60
C4-5  -----  g---d-----       ----h--q--  SEQ ID NO:61
```

| C. | | | | | |
|---|---|---|---|---|---|
| Virus | VP2 | VP2 | VP2 | VP2 | VP2 |
| isolate | #120 | #124 | #127 | #173 | #205 |
| 3B4-1 | I120T | Q124H | S127Q | | V205D |
| 3B4-3 | | | S127Q | F173Y | V205D |
| 3B4-4 | | | deleted | V205D | |
| 3B5-1 | | Q124H | S127Q | | V205D |
| 3B5-2 | | | S127Q | | V205D |
| 3B5-3 | | | S127Q | | V205D |
| 3B4-2 | (no mutation) | | | | |
| 3B5-4 | (no mutation) | | | | |

Figure 11

SEQUENCE LISTING

```
<160> NUMBER OF SEQ ID NOS: 92

<210> SEQ ID NO 1
<211> LENGTH: 77
<212> TYPE: PRT
<213> ORGANISM: Human rhinovirus
<220> FEATURE:
<221> NAME/KEY: MOD_RES
<222> LOCATION: (5)..(46)
<223> OTHER INFORMATION: Any amino acid
<220> FEATURE:
<221> NAME/KEY: MOD_RES
<222> LOCATION: (50)..(65)
<223> OTHER INFORMATION: Any amino acid

<400> SEQUENCE: 1

Thr Trp Ser Ser Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Lys Phe
        35                  40                  45

His Xaa Xaa Xaa Xaa Xaa Xaa Xaa Xaa Xaa Xaa Xaa Xaa Xaa Xaa
    50                  55                  60

Xaa Ala Leu His Gly Asn Val Asn Val Gly Tyr Asn Tyr
65                  70                  75

<210> SEQ ID NO 2
<211> LENGTH: 77
<212> TYPE: PRT
<213> ORGANISM: Human rhinovirus
<220> FEATURE:
<221> NAME/KEY: MOD_RES
<222> LOCATION: (5)..(46)
<223> OTHER INFORMATION: Any amino acid
<220> FEATURE:
<221> NAME/KEY: MOD_RES
<222> LOCATION: (50)..(65)
<223> OTHER INFORMATION: Any amino acid

<400> SEQUENCE: 2

Val Trp Lys Arg Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Lys Phe
```

```
                35                  40                  45
His Xaa Xaa Xaa Xaa Xaa Xaa Xaa Xaa Xaa Xaa Xaa Xaa Xaa
    50                  55                  60

Xaa Ala Asn Tyr Gly Asn Val Thr Ala Gly Tyr Asn Tyr
65                  70                  75

<210> SEQ ID NO 3
<211> LENGTH: 32
<212> TYPE: PRT
<213> ORGANISM: Human rhinovirus

<400> SEQUENCE: 3

His Pro Gly Glu Thr Gly Arg Glu Val Lys Ala Glu Thr Arg Leu Asn
1               5                   10                  15

Pro Asp Leu Gln Pro Thr Glu Glu Tyr Trp Leu Asn Phe Asp Gly Thr
            20                  25                  30

<210> SEQ ID NO 4
<211> LENGTH: 31
<212> TYPE: PRT
<213> ORGANISM: Human rhinovirus

<400> SEQUENCE: 4

His Pro Gly Glu Ala Gly Arg Asp Val Gly Gln Gln Arg Thr Asn Asn
1               5                   10                  15

Glu Lys Gln Pro Ser Asp Asp Asn Trp Leu Asn Phe Asp Gly Thr
            20                  25                  30

<210> SEQ ID NO 5
<211> LENGTH: 20
<212> TYPE: PRT
<213> ORGANISM: Human rhinovirus

<400> SEQUENCE: 5

Ile Cys Pro Leu Glu Thr Ser Ser Ala Ile Asn Thr Ile Pro Ile Thr
1               5                   10                  15

Ile Ser Ile Ser
            20

<210> SEQ ID NO 6
<211> LENGTH: 20
<212> TYPE: PRT
<213> ORGANISM: Human rhinovirus

<400> SEQUENCE: 6

Ser Pro Leu Asp Ala Asp Thr Ser Ala Thr Ala Ile Val Pro Ile Thr
1               5                   10                  15

Val Ser Ile Ser
            20

<210> SEQ ID NO 7
<211> LENGTH: 11
<212> TYPE: PRT
<213> ORGANISM: Human rhinovirus

<400> SEQUENCE: 7

Pro Ile Asn Asn Thr Asp Thr Tyr Ile Asn Ser
1               5                   10

<210> SEQ ID NO 8
<211> LENGTH: 11
<212> TYPE: PRT
```

```
<213> ORGANISM: Human rhinovirus

<400> SEQUENCE: 8

Pro Ile Asn Asn Thr Asn Glu Arg Ile Gly Asn
1               5                   10

<210> SEQ ID NO 9
<211> LENGTH: 18
<212> TYPE: PRT
<213> ORGANISM: Human rhinovirus

<400> SEQUENCE: 9

Ser Lys Leu Glu Val Thr Leu Ala Asn Tyr Asn Lys Glu Asn Phe Thr
1               5                   10                  15

Val Trp

<210> SEQ ID NO 10
<211> LENGTH: 18
<212> TYPE: PRT
<213> ORGANISM: Human rhinovirus

<400> SEQUENCE: 10

Ser Thr Ile Thr Met Lys Lys Glu Asn Tyr Asn Glu His Asn Phe Val
1               5                   10                  15

Asp Trp

<210> SEQ ID NO 11
<211> LENGTH: 13
<212> TYPE: PRT
<213> ORGANISM: Human rhinovirus

<400> SEQUENCE: 11

Thr Glu Lys His Ile His Lys Val His Ile Met Thr Arg
1               5                   10

<210> SEQ ID NO 12
<211> LENGTH: 13
<212> TYPE: PRT
<213> ORGANISM: Human rhinovirus

<400> SEQUENCE: 12

Thr Asn Gln Gln Glu His Leu Val Glu Val Thr Thr Arg
1               5                   10

<210> SEQ ID NO 13
<211> LENGTH: 31
<212> TYPE: PRT
<213> ORGANISM: Human rhinovirus

<400> SEQUENCE: 13

Ala Leu Glu Tyr Thr Arg Ala His Arg Thr Asn Phe Lys Ile Glu Asp
1               5                   10                  15

Arg Ser Ile Gln Thr Ala Ile Val Thr Arg Pro Ile Thr Thr
                20                  25                  30

<210> SEQ ID NO 14
<211> LENGTH: 31
<212> TYPE: PRT
<213> ORGANISM: Human rhinovirus

<400> SEQUENCE: 14

Ala Val Pro Tyr Thr His Ser Asn Val Thr Asn Tyr Lys Val Arg Asp
1               5                   10                  15
```

-continued

Gly Glu Pro Thr Leu Phe Ile Lys Pro Arg Glu Ser Leu Thr Thr
            20                  25                  30

<210> SEQ ID NO 15
<211> LENGTH: 20
<212> TYPE: PRT
<213> ORGANISM: Human rhinovirus

<400> SEQUENCE: 15

Ile Thr Met Lys Lys Glu Asn Tyr Asn Glu His Asn Gln Gln Glu His
1               5                   10                  15

Leu Val Glu Val
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Thr Met Leu Ile Glu Asn Tyr Asn Glu His Asn Gln Gln Glu His
1               5                   10                  15

Leu Val Glu Val
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Thr Met Lys Lys Glu Asn Tyr Asn Glu His Ala Gln Gln Glu His
1               5                   10                  15

Leu Val Glu Val
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Thr Met Lys Lys Gln Asn Tyr Asn Glu Gln Asn Gln Gln Glu His
1               5                   10                  15

Leu Val Glu Val
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

-continued

Ile Thr Met Lys Lys Glu Asn Tyr Asn Glu His Asn Gln Gln Ala His
1               5                   10                  15

Leu Val Gln Val
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Thr Met Leu Ile Glu Asn Tyr Asn Glu His Ala Gln Gln Glu His
1               5                   10                  15

Leu Val Glu Val
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Thr Met Lys Lys Glu Asn Tyr Asn Glu His Asn Gln Gln Ala His
1               5                   10                  15

Leu Val Gln Val
            20

<210> SEQ ID NO 22
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Arg Thr Leu Ile Glu Lys Gln Pro Pro Ile Asn Asn Thr Asn Glu
1               5                   10                  15

Arg Ile Gly Asn Tyr Lys Val Arg Asp Gly Glu Pro Thr Leu Phe Ile
            20                  25                  30

Lys Pro Arg Glu Ser Leu Thr Thr
            35                  40

<210> SEQ ID NO 23
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Arg Thr Asn Asn Glu Lys Gln Pro Pro Ile Asn Asn Thr Asn Ala
1               5                   10                  15

Arg Ile Gly Asn Tyr Lys Val Arg Asp Gly Glu Pro Thr Leu Phe Ile
            20                  25                  30

Lys Pro Arg Gln Ser Leu Thr Thr

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Arg Thr Asn Asn Glu Lys Gln Pro Pro Ile Asn Asn Thr Asn Glu
1               5                   10                  15

Arg Ile Gly Asn Tyr Ala Val Arg Asp Gly Glu Ala Thr Leu Phe Ile
            20                  25                  30

Lys Pro Arg Glu Ser Leu Thr Thr
        35                  40

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Ile Thr Asn Asn Gln Lys Gln Pro Pro Ile Asn Asn Thr Asn Glu
1               5                   10                  15

Arg Ala Gly Asn Tyr Lys Val Arg Asp Gly Glu Pro Thr Leu Phe Ile
            20                  25                  30

Lys Pro Arg Glu Ser Leu Thr Thr
        35                  40

<210> SEQ ID NO 26
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Arg Thr Asn Asn Glu Lys Gln Pro Pro Ile Asn Asn Thr Asn Glu
1               5                   10                  15

Arg Ile Gly Asn Tyr Lys Val Ile Asp Gly Glu Pro Thr Leu Phe Ile
            20                  25                  30

Lys Leu Arg Ile Ser Leu Thr Thr
        35                  40

<210> SEQ ID NO 27
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Arg Thr Leu Ile Glu Lys Gln Pro Pro Ile Asn Asn Thr Asn Ala
1               5                   10                  15

Arg Ile Gly Asn Tyr Ala Val Arg Asp Gly Glu Ala Thr Leu Phe Ile
            20                  25                  30

Lys Pro Arg Gln Ser Leu Thr Thr
            35                  40

<210> SEQ ID NO 28
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ile Thr Asn Asn Gln Lys Gln Pro Pro Ile Asn Asn Thr Asn Glu
1               5                   10                  15

Arg Ala Gly Asn Tyr Lys Val Ile Asp Gly Glu Pro Thr Leu Phe Ile
            20                  25                  30

Lys Leu Arg Ile Ser Leu Thr Thr
            35                  40

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Lys Arg Asp Glu Thr Ser Ser Gly Ile Leu Thr Ile
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Ala Gly Asp Glu Thr Ser Ser Ala Ile Asn Thr Ile
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Ala Gly Asp Glu Thr Ser Ser Gly Ile Leu Thr Ile
1               5                   10

<210> SEQ ID NO 32
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ile Thr Met Leu Ile Glu Asn Tyr Asn Glu His Ala Gln Gln Glu His
1               5                   10                  15

```
Leu Val Glu Val Gln Arg Thr Leu Ile Glu Lys Gln Pro Ile Asn
            20                  25                  30

Asn Thr Asn Ala Arg Ile Gly Asn Tyr Ala Val Arg Asp Gly Glu Ala
        35                  40                  45

Thr Leu Phe Ile Lys Pro Arg Gln Ser Leu Thr Thr Trp Lys Arg Asp
    50                  55                  60

Glu Thr Ser Ser Gly Ile Leu Thr Ile
65                  70

<210> SEQ ID NO 33
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ile Thr Met Lys Lys Glu Asn Tyr Asn Glu His Asn Gln Gln Ala His
1               5                   10                  15

Leu Val Gln Val Gln Ile Thr Asn Asn Gln Lys Gln Pro Pro Ile Asn
            20                  25                  30

Asn Thr Asn Glu Arg Ala Gly Asn Tyr Lys Val Ile Asp Gly Glu Pro
        35                  40                  45

Thr Leu Phe Ile Lys Leu Arg Ile Ser Leu Thr Thr Trp Ala Gly Asp
    50                  55                  60

Glu Thr Ser Ser Ala Ile Asn Thr Ile
65                  70

<210> SEQ ID NO 34
<211> LENGTH: 19
<212> TYPE: PRT
<213> ORGANISM: Human rhinovirus

<400> SEQUENCE: 34

Ser Val Leu Asp Ile Val Asp Asn Tyr Asn Asp Gln Ser Phe Thr Lys
1               5                   10                  15

Trp Lys Ile

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Val Leu Ala Ile Val Ala Asn Tyr Asn Gly Ala Ser Phe Thr Ala
1               5                   10                  15

Trp Lys Ile

<210> SEQ ID NO 36
<211> LENGTH: 20
<212> TYPE: PRT
<213> ORGANISM: Human rhinovirus

<400> SEQUENCE: 36

Ser Arg Ile Val Thr Ser Glu Gln Leu His Lys Val Lys Val Val Thr
1               5                   10                  15

Arg Ile Tyr His
```

```
<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Arg Ile Val Thr Ala Gly Ala Leu His Ala Val Ala Val Val Thr
1               5                   10                  15

Arg Ile Tyr His
            20

<210> SEQ ID NO 38
<211> LENGTH: 19
<212> TYPE: PRT
<213> ORGANISM: Human rhinovirus

<400> SEQUENCE: 38

Gly Arg Glu Val Gly Thr Gln Val Glu Asn Glu Lys Gln Pro Ser Asp
1               5                   10                  15

Asp Asn Trp

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ala Gln Val Gly Thr Gln Val Gln Asn Gln Ala Gln Pro Ser Asp
1               5                   10                  15

Asp Asn Trp

<210> SEQ ID NO 40
<211> LENGTH: 10
<212> TYPE: PRT
<213> ORGANISM: Human rhinovirus

<400> SEQUENCE: 40

Thr Gln Ser Asn Ile Gly Asn Val Ser Met
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ala Ser Ala Ile Gly Asn Val Ser Met
1               5                   10

<210> SEQ ID NO 42
<211> LENGTH: 21
<212> TYPE: PRT
<213> ORGANISM: Human rhinovirus
```

```
<400> SEQUENCE: 42

Thr His Thr Thr Asn Tyr Lys Leu Ser Ser Glu Val His Asn Asp Val
1               5                   10                  15

Ala Ile Arg Pro Arg
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr His Thr Thr Asn Tyr Ala Leu Ser Val Gln Val His Asn Asp Val
1               5                   10                  15

Ala Ile Ala Pro Ala
            20

<210> SEQ ID NO 44
<211> LENGTH: 20
<212> TYPE: PRT
<213> ORGANISM: Human rhinovirus

<400> SEQUENCE: 44

Phe Tyr Thr Leu Asp Ser Lys Met Trp Asn Ser Thr Ser Lys Gly Trp
1               5                   10                  15

Trp Trp Lys Leu
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Tyr Thr Leu Asp Ser Lys Met Trp Ala Gly Thr Ser Ala Gly Trp
1               5                   10                  15

Trp Trp Lys Leu
            20

<210> SEQ ID NO 46
<211> LENGTH: 19
<212> TYPE: PRT
<213> ORGANISM: Human rhinovirus

<400> SEQUENCE: 46

Val Ile Ile Pro Val Cys Gln Leu Gln Ser Asn Asn Ile Ser Asn Ile
1               5                   10                  15

Val Pro Ile

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
Val Ile Ile Pro Val Cys Gln Leu Ala Ser Asn Ala Ile Ser Ala Ile
1               5                   10                  15

Val Pro Ile

<210> SEQ ID NO 48
<211> LENGTH: 8
<212> TYPE: PRT
<213> ORGANISM: Human rhinovirus

<400> SEQUENCE: 48

Phe Ser Gly Ala Arg Ala Lys Thr
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Ser Gly Ala Val Ala Leu Thr
1               5

<210> SEQ ID NO 50
<211> LENGTH: 25
<212> TYPE: PRT
<213> ORGANISM: Human rhinovirus

<400> SEQUENCE: 50

Asp Ala Thr Gly Ile Asp Asn His Arg Glu Ala Lys Leu Phe Asn Ile
1               5                   10                  15

Pro Glu His Gln Leu Ala Ser His Glu
            20                  25

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ala Thr Gly Ile Asp Asn His Arg Glu Ala Lys Leu Phe Asn Ile
1               5                   10                  15

Pro Glu His Gln Leu Ala Ser His Glu
            20                  25

<210> SEQ ID NO 52
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ala Thr Gly Ile Asp Asn His Arg Asp Ala Lys Leu Phe Asn Ile
1               5                   10                  15

Pro Glu His Gln Leu Ala Ser His Glu
            20                  25
```

<210> SEQ ID NO 53
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Ala Thr Gly Ile Asn Asn His Arg Glu Ala Lys Leu Phe Asn Ile
1               5                   10                  15

Pro Glu His Gln Leu Ala Ser His Glu
            20                  25

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ala Thr Gly Ile Asp Asn His Arg Glu Ala Lys Leu Phe Asn Ile
1               5                   10                  15

Pro Glu His Gln Leu Ala Ser His Glu
            20                  25

<210> SEQ ID NO 55
<211> LENGTH: 25
<212> TYPE: PRT
<213> ORGANISM: Human rhinovirus

<400> SEQUENCE: 55

Asp Ala Thr Gly Ile Asp Asn His Arg Glu Ala Lys Leu Phe Asn Ile
1               5                   10                  15

Pro Glu His Gln Leu Ala Ser His Glu
            20                  25

<210> SEQ ID NO 56
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Ala Thr Gly Ile Asp Asn His Arg Ala Ala Lys Leu Phe Asn Thr
1               5                   10                  15

Pro Glu His His His Asn Gln His Glu
            20                  25

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ala Thr Gly Ile Asn Asn His Arg Glu Ala Lys Leu Phe Asn Ile
1               5                   10                  15

Pro Glu His Gln Leu Ala Ser His Glu
            20                  25

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Thr Gly Ile Asn Asn His Arg Glu Ala Lys Leu Phe Asn Thr
1               5                   10                  15

Pro Glu His His Leu Thr Gln His Glu
            20                  25

<210> SEQ ID NO 59
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ala Thr Gly Ile Gly Asn His Arg Glu Ala Lys Leu Phe Asn Thr
1               5                   10                  15

Pro Glu His His Leu Asn Gln His Glu
            20                  25

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Ala Thr Gly Ile Gly Asn His Arg Glu Ala Lys Leu Phe Asn Ile
1               5                   10                  15

Pro Glu His His Leu Thr Gln His Glu
            20                  25

<210> SEQ ID NO 61
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Ala Thr Gly Ile Gly Asn His Arg Asp Ala Lys Leu Phe Asn Ile
1               5                   10                  15

Pro Glu His His Leu Ala Gln His Glu
            20                  25

<210> SEQ ID NO 62
<211> LENGTH: 40
<212> TYPE: PRT
<213> ORGANISM: Human rhinovirus

<400> SEQUENCE: 62

-continued

Gln Arg Thr Asn Asn Glu Lys Gln Pro Pro Ile Asn Asn Thr Asn Glu
1               5                   10                  15

Arg Ile Gly Asn Tyr Lys Val Arg Asp Gly Glu Pro Thr Leu Phe Ile
            20                  25                  30

Lys Pro Arg Glu Ser Leu Thr Thr
            35                  40

<210> SEQ ID NO 63
<211> LENGTH: 13
<212> TYPE: PRT
<213> ORGANISM: Human rhinovirus

<400> SEQUENCE: 63

Trp Lys Arg Asp Glu Thr Ser Ser Ala Ile Asn Thr Ile
1               5                   10

<210> SEQ ID NO 64
<211> LENGTH: 859
<212> TYPE: PRT
<213> ORGANISM: Human rhinovirus

<400> SEQUENCE: 64

Met Gly Ala Gln Val Ser Arg Gln Asn Val Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
            115                 120                 125

Ser Asn Arg Phe Tyr Thr Leu Asp Ser Lys Met Trp Asn Ser Thr Ser
        130                 135                 140

Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
            195                 200                 205

Val Asn Ala Gly Tyr Lys Tyr Thr His Pro Gly Glu Ala Gly Arg Glu
        210                 215                 220

Val Gly Thr Gln Val Glu Asn Glu Lys Gln Pro Ser Asp Asp Asn Trp
225                 230                 235                 240

Leu Asn Phe Asp Gly Thr Leu Leu Gly Asn Leu Leu Ile Phe Pro His
                245                 250                 255

Gln Phe Ile Asn Leu Arg Ser Asn Asn Ser Ala Thr Leu Ile Val Pro
            260                 265                 270

-continued

Tyr Val Asn Ala Val Pro Met Asp Ser Met Val Arg His Asn Asn Trp
            275                 280                 285

Ser Leu Val Ile Ile Pro Val Cys Gln Leu Gln Ser Asn Asn Ile Ser
    290                 295                 300

Asn Ile Val Pro Ile Thr Val Ser Ile Ser Pro Met Cys Ala Glu Phe
305                 310                 315                 320

Ser Gly Ala Arg Ala Lys Thr Val Val Gln Gly Leu Pro Val Tyr Val
                325                 330                 335

Thr Pro Gly Ser Gly Gln Phe Met Thr Thr Asp Met Gln Ser Pro
            340                 345                 350

Cys Ala Leu Pro Trp Tyr His Pro Thr Lys Glu Ile Phe Ile Pro Gly
            355                 360                 365

Glu Val Lys Asn Leu Ile Glu Met Cys Gln Val Asp Thr Leu Ile Pro
370                 375                 380

Ile Asn Ser Thr Gln Ser Asn Ile Gly Asn Val Ser Met Tyr Thr Val
385                 390                 395                 400

Thr Leu Ser Pro Gln Thr Lys Leu Ala Glu Glu Ile Phe Ala Ile Lys
                405                 410                 415

Val Asp Ile Ala Ser His Pro Leu Ala Thr Thr Leu Ile Gly Glu Ile
                420                 425                 430

Ala Ser Tyr Phe Thr His Trp Thr Gly Ser Leu Arg Phe Ser Phe Met
            435                 440                 445

Phe Cys Gly Thr Ala Asn Thr Thr Leu Lys Val Leu Leu Ala Tyr Thr
            450                 455                 460

Pro Pro Gly Ile Gly Lys Pro Arg Ser Arg Lys Glu Ala Met Leu Gly
465                 470                 475                 480

Thr His Val Val Trp Asp Val Gly Leu Gln Ser Thr Val Ser Leu Val
                485                 490                 495

Val Pro Trp Ile Ser Ala Ser Gln Tyr Arg Phe Thr Thr Pro Asp Thr
                500                 505                 510

Tyr Ser Ser Ala Gly Tyr Ile Thr Cys Trp Tyr Gln Thr Asn Phe Val
            515                 520                 525

Val Pro Pro Asn Thr Pro Asn Thr Ala Glu Met Leu Cys Phe Val Ser
530                 535                 540

Gly Cys Asn His Phe Cys Leu Arg Met Ala Arg Asp Thr Asp Leu His
545                 550                 555                 560

Lys Gln Thr Gly Pro Ile Thr Gln Asn Pro Val Glu Arg Tyr Val Asp
                565                 570                 575

Glu Val Leu Asn Glu Val Leu Val Pro Asn Ile Asn Gln Ser His
            580                 585                 590

Pro Thr Thr Ser Asn Ala Ala Pro Val Leu Asp Ala Ala Glu Thr Gly
            595                 600                 605

His Thr Asn Lys Ile Gln Pro Glu Asp Thr Ile Glu Thr Arg Tyr Val
    610                 615                 620

Gln Ser Ser Gln Thr Leu Asp Glu Met Ser Val Glu Ser Phe Leu Gly
625                 630                 635                 640

Arg Ser Gly Cys Ile His Glu Ser Val Leu Asp Ile Val Asp Asn Tyr
                645                 650                 655

Asn Asp Gln Ser Phe Thr Lys Trp Asn Ile Asn Leu Gln Glu Met Ala
                660                 665                 670

Gln Ile Arg Arg Lys Phe Glu Met Phe Thr Tyr Ala Arg Phe Asp Ser
            675                 680                 685

Glu Ile Thr Met Val Pro Ser Val Ala Ala Lys Asp Gly His Ile Gly

```
               690              695              700
His Ile Val Met Gln Tyr Met Tyr Val Pro Pro Gly Ala Pro Ile Pro
705              710              715              720

Thr Thr Arg Asp Asp Tyr Ala Trp Gln Ser Gly Thr Asn Ala Ser Val
             725              730              735

Phe Trp Gln His Gly Gln Pro Phe Pro Arg Phe Ser Leu Pro Phe Leu
             740              745              750

Ser Ile Ala Ser Ala Tyr Tyr Met Phe Tyr Asp Gly Tyr Asp Gly Asp
             755              760              765

Thr Tyr Lys Ser Arg Tyr Gly Thr Val Val Thr Asn Asp Met Gly Thr
770              775              780

Leu Cys Ser Arg Ile Val Thr Ser Glu Gln Leu His Lys Val Lys Val
785              790              795              800

Val Thr Arg Ile Tyr His Lys Ala Lys His Thr Lys Ala Trp Cys Pro
             805              810              815

Arg Pro Pro Arg Ala Val Gln Tyr Ser His Thr His Thr Thr Asn Tyr
             820              825              830

Lys Leu Ser Ser Glu Val His Asn Asp Val Ala Ile Arg Pro Arg Thr
             835              840              845

Asn Leu Thr Thr Val Gly Pro Ser Asp Met Tyr
850              855
```

<210> SEQ ID NO 65
<211> LENGTH: 859
<212> TYPE: PRT
<213> ORGANISM: Human rhinovirus

<400> SEQUENCE: 65

```
Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
                20                  25                  30

Phe Lys Asp Ala Ala Ser Ser Gly Ala Ser Arg Leu Asp Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Asp Ser Lys Met Trp Ala Gly Thr Ser
130                 135                 140

Ala Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
        195                 200                 205
```

-continued

```
Val Asn Ala Gly Tyr Lys Tyr Thr His Pro Gly Ala Gly Arg Glu
210                 215                 220

Val Gly Thr Gln Val Glu Asn Glu Lys Gln Pro Ser Asp Asp Asn Trp
225                 230                 235                 240

Leu Asn Phe Asp Gly Thr Leu Leu Gly Asn Leu Leu Ile Phe Pro His
                245                 250                 255

Gln Phe Ile Asn Leu Arg Ser Asn Asn Ser Ala Thr Leu Ile Val Pro
            260                 265                 270

Tyr Val Asn Ala Val Pro Met Asp Ser Met Val Arg His Asn Asn Trp
        275                 280                 285

Ser Leu Val Ile Ile Pro Val Cys Gln Leu Gln Ser Asn Asn Ile Ser
290                 295                 300

Asn Ile Val Pro Ile Thr Val Ser Ile Ser Pro Met Cys Ala Glu Phe
305                 310                 315                 320

Ser Gly Ala Arg Ala Lys Thr Val Val Gln Gly Leu Pro Val Tyr Val
                325                 330                 335

Thr Pro Gly Ser Gly Gln Phe Met Thr Thr Asp Asp Met Gln Ser Pro
            340                 345                 350

Cys Ala Leu Pro Trp Tyr His Pro Thr Lys Glu Ile Phe Ile Pro Gly
        355                 360                 365

Glu Val Lys Asn Leu Ile Glu Met Cys Gln Val Asp Thr Leu Ile Pro
370                 375                 380

Ile Asn Ser Thr Gln Ser Asn Ile Gly Asn Val Ser Met Tyr Thr Val
385                 390                 395                 400

Thr Leu Ser Pro Gln Thr Lys Leu Ala Glu Glu Ile Phe Ala Ile Lys
                405                 410                 415

Val Asp Ile Ala Ser His Pro Leu Ala Thr Leu Ile Gly Glu Ile
            420                 425                 430

Ala Ser Tyr Phe Thr His Trp Thr Gly Ser Leu Arg Phe Ser Phe Met
        435                 440                 445

Phe Cys Gly Thr Ala Asn Thr Thr Leu Lys Val Leu Leu Ala Tyr Thr
450                 455                 460

Pro Pro Gly Ile Gly Lys Pro Arg Ser Arg Lys Glu Ala Met Leu Gly
465                 470                 475                 480

Thr His Val Val Trp Asp Val Gly Leu Gln Ser Thr Val Ser Leu Val
                485                 490                 495

Val Pro Trp Ile Ser Ala Ser Gln Tyr Arg Phe Thr Thr Pro Asp Thr
            500                 505                 510

Tyr Ser Ser Ala Gly Tyr Ile Thr Cys Trp Tyr Gln Thr Asn Phe Val
        515                 520                 525

Val Pro Pro Asn Thr Pro Asn Thr Ala Glu Met Leu Cys Phe Val Ser
530                 535                 540

Gly Cys Asn His Phe Cys Leu Arg Met Ala Arg Asp Thr Asp Leu His
545                 550                 555                 560

Lys Gln Thr Gly Pro Ile Thr Gln Asn Pro Val Glu Arg Tyr Val Asp
                565                 570                 575

Glu Val Leu Asn Glu Val Leu Val Pro Asn Ile Asn Gln Ser His
            580                 585                 590

Pro Thr Thr Ser Asn Ala Ala Pro Val Leu Asp Ala Ala Glu Thr Gly
        595                 600                 605

His Thr Asn Lys Ile Gln Pro Glu Asp Thr Ile Glu Thr Arg Tyr Val
610                 615                 620

Gln Ser Ser Gln Thr Leu Asp Glu Met Ser Val Glu Ser Phe Leu Gly
```

```
                 625                 630                 635                 640
Arg Ser Gly Cys Ile His Glu Ser Val Leu Asp Ile Val Asp Asn Tyr
                                645                 650                 655

Asn Asp Gln Ser Phe Thr Lys Trp Asn Ile Asn Leu Gln Glu Met Ala
                660                 665                 670

Gln Ile Arg Arg Lys Phe Glu Met Phe Thr Tyr Ala Arg Phe Asp Ser
                675                 680                 685

Glu Ile Thr Met Val Pro Ser Val Ala Ala Lys Asp Gly His Ile Gly
            690                 695                 700

His Ile Val Met Gln Tyr Met Tyr Val Pro Pro Gly Ala Pro Ile Pro
705                 710                 715                 720

Thr Thr Arg Asp Asp Tyr Ala Trp Gln Ser Gly Thr Asn Ala Ser Val
                725                 730                 735

Phe Trp Gln His Gly Gln Pro Phe Pro Arg Phe Ser Leu Pro Phe Leu
                740                 745                 750

Ser Ile Ala Ser Ala Tyr Tyr Met Phe Tyr Asp Gly Tyr Asp Gly Asp
                755                 760                 765

Thr Tyr Lys Ser Arg Tyr Gly Thr Val Val Thr Asn Asp Met Gly Thr
            770                 775                 780

Leu Cys Ser Arg Ile Val Thr Ser Glu Gln Leu His Lys Val Lys Val
785                 790                 795                 800

Val Thr Arg Ile Tyr His Lys Ala Lys His Thr Lys Ala Trp Cys Pro
                805                 810                 815

Arg Pro Pro Arg Ala Val Gln Tyr Ser His Thr His Thr Thr Asn Tyr
                820                 825                 830

Lys Leu Ser Ser Glu Val His Asn Asp Val Ala Ile Arg Pro Arg Thr
            835                 840                 845

Asn Leu Thr Thr Val Gly Pro Ser Asp Met Tyr
        850                 855

<210> SEQ ID NO 66
<211> LENGTH: 859
<212> TYPE: PRT
<213> ORGANISM: Human rhinovirus

<400> SEQUENCE: 66

Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Asp Ser Lys Met Trp Asn Ser Thr Ser
    130                 135                 140
```

-continued

```
Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
        195                 200                 205

Val Asn Ala Gly Tyr Lys Tyr Thr His Pro Gly Glu Ala Gly Ala Gln
    210                 215                 220

Val Gly Thr Gln Val Gln Asn Gln Ala Gln Pro Ser Asp Asp Asn Trp
225                 230                 235                 240

Leu Asn Phe Asp Gly Thr Leu Leu Gly Asn Leu Leu Ile Phe Pro His
                245                 250                 255

Gln Phe Ile Asn Leu Arg Ser Asn Asn Ser Ala Thr Leu Ile Val Pro
                260                 265                 270

Tyr Val Asn Ala Val Pro Met Asp Ser Met Val Arg His Asn Asn Trp
            275                 280                 285

Ser Leu Val Ile Ile Pro Val Cys Gln Leu Gln Ser Asn Asn Ile Ser
        290                 295                 300

Asn Ile Val Pro Ile Thr Val Ser Ile Ser Pro Met Cys Ala Glu Phe
305                 310                 315                 320

Ser Gly Ala Arg Ala Lys Thr Val Val Gln Gly Leu Pro Val Tyr Val
                325                 330                 335

Thr Pro Gly Ser Gly Gln Phe Met Thr Thr Asp Asp Met Gln Ser Pro
            340                 345                 350

Cys Ala Leu Pro Trp Tyr His Pro Thr Lys Glu Ile Phe Ile Pro Gly
        355                 360                 365

Glu Val Lys Asn Leu Ile Glu Met Cys Gln Val Asp Thr Leu Ile Pro
    370                 375                 380

Ile Asn Ser Thr Gln Ser Asn Ile Gly Asn Val Ser Met Tyr Thr Val
385                 390                 395                 400

Thr Leu Ser Pro Gln Thr Lys Leu Ala Glu Glu Ile Phe Ala Ile Lys
                405                 410                 415

Val Asp Ile Ala Ser His Pro Leu Ala Thr Thr Leu Ile Gly Glu Ile
            420                 425                 430

Ala Ser Tyr Phe Thr His Trp Thr Gly Ser Leu Arg Phe Ser Phe Met
        435                 440                 445

Phe Cys Gly Thr Ala Asn Thr Thr Leu Lys Val Leu Leu Ala Tyr Thr
    450                 455                 460

Pro Pro Gly Ile Gly Lys Pro Arg Ser Arg Lys Glu Ala Met Leu Gly
465                 470                 475                 480

Thr His Val Val Trp Asp Val Gly Leu Gln Ser Thr Val Ser Leu Val
                485                 490                 495

Val Pro Trp Ile Ser Ala Ser Gln Tyr Arg Phe Thr Thr Pro Asp Thr
            500                 505                 510

Tyr Ser Ser Ala Gly Tyr Ile Thr Cys Trp Tyr Gln Thr Asn Phe Val
        515                 520                 525

Val Pro Pro Asn Thr Pro Asn Thr Ala Glu Met Leu Cys Phe Val Ser
    530                 535                 540

Gly Cys Asn His Phe Cys Leu Arg Met Ala Arg Asp Thr Asp Leu His
545                 550                 555                 560

Lys Gln Thr Gly Pro Ile Thr Gln Asn Pro Val Glu Arg Tyr Val Asp
```

-continued

```
                565                 570                 575

Glu Val Leu Asn Glu Val Leu Val Pro Asn Ile Asn Gln Ser His
            580                 585                 590

Pro Thr Thr Ser Asn Ala Ala Pro Val Leu Asp Ala Ala Glu Thr Gly
            595                 600                 605

His Thr Asn Lys Ile Gln Pro Glu Asp Thr Ile Glu Thr Arg Tyr Val
            610                 615                 620

Gln Ser Ser Gln Thr Leu Asp Glu Met Ser Val Glu Ser Phe Leu Gly
625                 630                 635                 640

Arg Ser Gly Cys Ile His Glu Ser Val Leu Asp Ile Val Asp Asn Tyr
                645                 650                 655

Asn Asp Gln Ser Phe Thr Lys Trp Asn Ile Asn Leu Gln Glu Met Ala
                660                 665                 670

Gln Ile Arg Arg Lys Phe Glu Met Phe Thr Tyr Ala Arg Phe Asp Ser
                675                 680                 685

Glu Ile Thr Met Val Pro Ser Val Ala Ala Lys Asp Gly His Ile Gly
            690                 695                 700

His Ile Val Met Gln Tyr Met Tyr Val Pro Pro Gly Ala Pro Ile Pro
705                 710                 715                 720

Thr Thr Arg Asp Asp Tyr Ala Trp Gln Ser Gly Thr Asn Ala Ser Val
                725                 730                 735

Phe Trp Gln His Gly Gln Pro Phe Pro Arg Phe Ser Leu Pro Phe Leu
                740                 745                 750

Ser Ile Ala Ser Ala Tyr Tyr Met Phe Tyr Asp Gly Tyr Asp Gly Asp
                755                 760                 765

Thr Tyr Lys Ser Arg Tyr Gly Thr Val Val Thr Asn Asp Met Gly Thr
770                 775                 780

Leu Cys Ser Arg Ile Val Thr Ser Glu Gln Leu His Lys Val Lys Val
785                 790                 795                 800

Val Thr Arg Ile Tyr His Lys Ala Lys His Thr Lys Ala Trp Cys Pro
                805                 810                 815

Arg Pro Pro Arg Ala Val Gln Tyr Ser His Thr His Thr Thr Asn Tyr
                820                 825                 830

Lys Leu Ser Ser Glu Val His Asn Asp Val Ala Ile Arg Pro Arg Thr
                835                 840                 845

Asn Leu Thr Thr Val Gly Pro Ser Asp Met Tyr
                850                 855

<210> SEQ ID NO 67
<211> LENGTH: 859
<212> TYPE: PRT
<213> ORGANISM: Human rhinovirus

<400> SEQUENCE: 67

Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
                20                  25                  30

Phe Lys Asp Ala Ala Ser Ser Gly Ala Ser Arg Leu Asp Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Ser Val Glu Ala Cys Gly Tyr Ser Asp
65              70                  75                  80
```

-continued

Arg Ile Ile Gln Ile Thr Arg Gly Asp Ser Thr Ile Thr Ser Gln Asp
            85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
            115                 120                 125

Ser Asn Arg Phe Tyr Thr Leu Asp Ser Lys Met Trp Asn Ser Thr Ser
            130                 135                 140

Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
            165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
            195                 200                 205

Val Asn Ala Gly Tyr Lys Tyr Thr His Pro Gly Glu Ala Gly Arg Glu
            210                 215                 220

Val Gly Thr Gln Val Glu Asn Glu Lys Gln Pro Ser Asp Asp Asn Trp
225                 230                 235                 240

Leu Asn Phe Asp Gly Thr Leu Leu Gly Asn Leu Leu Ile Phe Pro His
            245                 250                 255

Gln Phe Ile Asn Leu Arg Ser Asn Asn Ser Ala Thr Leu Ile Val Pro
            260                 265                 270

Tyr Val Asn Ala Val Pro Met Asp Ser Met Val Arg His Asn Asn Trp
            275                 280                 285

Ser Leu Val Ile Ile Pro Val Cys Gln Leu Ala Ser Asn Ala Ile Ser
            290                 295                 300

Ala Ile Val Pro Ile Thr Val Ser Ile Ser Pro Met Cys Ala Glu Phe
305                 310                 315                 320

Ser Gly Ala Arg Ala Lys Thr Val Val Gln Gly Leu Pro Val Tyr Val
            325                 330                 335

Thr Pro Gly Ser Gly Gln Phe Met Thr Thr Asp Asp Met Gln Ser Pro
            340                 345                 350

Cys Ala Leu Pro Trp Tyr His Pro Thr Lys Glu Ile Phe Ile Pro Gly
            355                 360                 365

Glu Val Lys Asn Leu Ile Glu Met Cys Gln Val Asp Thr Leu Ile Pro
            370                 375                 380

Ile Asn Ser Thr Gln Ser Asn Ile Gly Asn Val Ser Met Tyr Thr Val
385                 390                 395                 400

Thr Leu Ser Pro Gln Thr Lys Leu Ala Glu Glu Ile Phe Ala Ile Lys
            405                 410                 415

Val Asp Ile Ala Ser His Pro Leu Ala Thr Thr Leu Ile Gly Glu Ile
            420                 425                 430

Ala Ser Tyr Phe Thr His Trp Thr Gly Ser Leu Arg Phe Ser Phe Met
            435                 440                 445

Phe Cys Gly Thr Ala Asn Thr Thr Leu Lys Val Leu Leu Ala Tyr Thr
            450                 455                 460

Pro Pro Gly Ile Gly Lys Pro Arg Ser Arg Lys Glu Ala Met Leu Gly
465                 470                 475                 480

Thr His Val Val Trp Asp Val Gly Leu Gln Ser Thr Val Ser Leu Val
            485                 490                 495

Val Pro Trp Ile Ser Ala Ser Gln Tyr Arg Phe Thr Thr Pro Asp Thr

```
                    500                 505                 510
Tyr Ser Ser Ala Gly Tyr Ile Thr Cys Trp Tyr Gln Thr Asn Phe Val
        515                 520                 525

Val Pro Pro Asn Thr Pro Asn Thr Ala Glu Met Leu Cys Phe Val Ser
    530                 535                 540

Gly Cys Asn His Phe Cys Leu Arg Met Ala Arg Asp Thr Asp Leu His
545                 550                 555                 560

Lys Gln Thr Gly Pro Ile Thr Gln Asn Pro Val Glu Arg Tyr Val Asp
                565                 570                 575

Glu Val Leu Asn Glu Val Leu Val Pro Asn Ile Asn Gln Ser His
            580                 585                 590

Pro Thr Thr Ser Asn Ala Ala Pro Val Leu Asp Ala Ala Glu Thr Gly
        595                 600                 605

His Thr Asn Lys Ile Gln Pro Glu Asp Thr Ile Glu Thr Arg Tyr Val
    610                 615                 620

Gln Ser Ser Gln Thr Leu Asp Glu Met Ser Val Glu Ser Phe Leu Gly
625                 630                 635                 640

Arg Ser Gly Cys Ile His Glu Ser Val Leu Asp Ile Val Asp Asn Tyr
                645                 650                 655

Asn Asp Gln Ser Phe Thr Lys Trp Asn Ile Asn Leu Gln Glu Met Ala
            660                 665                 670

Gln Ile Arg Arg Lys Phe Glu Met Phe Thr Tyr Ala Arg Phe Asp Ser
        675                 680                 685

Glu Ile Thr Met Val Pro Ser Val Ala Ala Lys Asp Gly His Ile Gly
    690                 695                 700

His Ile Val Met Gln Tyr Met Tyr Val Pro Pro Gly Ala Pro Ile Pro
705                 710                 715                 720

Thr Thr Arg Asp Asp Tyr Ala Trp Gln Ser Gly Thr Asn Ala Ser Val
                725                 730                 735

Phe Trp Gln His Gly Gln Pro Phe Pro Arg Phe Ser Leu Pro Phe Leu
            740                 745                 750

Ser Ile Ala Ser Ala Tyr Tyr Met Phe Tyr Asp Gly Tyr Asp Gly Asp
        755                 760                 765

Thr Tyr Lys Ser Arg Tyr Gly Thr Val Val Thr Asn Asp Met Gly Thr
    770                 775                 780

Leu Cys Ser Arg Ile Val Thr Ser Glu Gln Leu His Lys Val Lys Val
785                 790                 795                 800

Val Thr Arg Ile Tyr His Lys Ala Lys His Thr Lys Ala Trp Cys Pro
                805                 810                 815

Arg Pro Pro Arg Ala Val Gln Tyr Ser His Thr His Thr Thr Asn Tyr
            820                 825                 830

Lys Leu Ser Ser Glu Val His Asn Asp Val Ala Ile Arg Pro Arg Thr
        835                 840                 845

Asn Leu Thr Thr Val Gly Pro Ser Asp Met Tyr
    850                 855

<210> SEQ ID NO 68
<211> LENGTH: 859
<212> TYPE: PRT
<213> ORGANISM: Human rhinovirus

<400> SEQUENCE: 68

Met Gly Ala Gln Val Ser Arg Gln Asn Val Gly Thr His Ser Thr Gln
1               5                   10                  15
```

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Asp Ser Lys Met Trp Asn Ser Thr Ser
    130                 135                 140

Lys Gly Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
        195                 200                 205

Val Asn Ala Gly Tyr Lys Tyr Thr His Pro Gly Glu Ala Gly Arg Glu
    210                 215                 220

Val Gly Thr Gln Val Glu Asn Glu Lys Gln Pro Ser Asp Asp Asn Trp
225                 230                 235                 240

Leu Asn Phe Asp Gly Thr Leu Leu Gly Asn Leu Leu Ile Phe Pro His
                245                 250                 255

Gln Phe Ile Asn Leu Arg Ser Asn Asn Ser Ala Thr Leu Ile Val Pro
            260                 265                 270

Tyr Val Asn Ala Val Pro Met Asp Ser Met Val Arg His Asn Asn Trp
        275                 280                 285

Ser Leu Val Ile Ile Pro Val Cys Gln Leu Gln Ser Asn Asn Ile Ser
    290                 295                 300

Asn Ile Val Pro Ile Thr Val Ser Ile Ser Pro Met Cys Ala Glu Phe
305                 310                 315                 320

Ser Gly Ala Val Ala Leu Thr Val Val Gln Gly Leu Pro Val Tyr Val
                325                 330                 335

Thr Pro Gly Ser Gly Gln Phe Met Thr Thr Asp Asp Met Gln Ser Pro
            340                 345                 350

Cys Ala Leu Pro Trp Tyr His Pro Thr Lys Glu Ile Phe Ile Pro Gly
        355                 360                 365

Glu Val Lys Asn Leu Ile Glu Met Cys Gln Val Asp Thr Leu Ile Pro
    370                 375                 380

Ile Asn Ser Thr Gln Ser Asn Ile Gly Asn Val Ser Met Tyr Thr Val
385                 390                 395                 400

Thr Leu Ser Pro Gln Thr Lys Leu Ala Glu Glu Ile Phe Ala Ile Lys
                405                 410                 415

Val Asp Ile Ala Ser His Pro Leu Ala Thr Thr Leu Ile Gly Glu Ile
            420                 425                 430

Ala Ser Tyr Phe Thr His Trp Thr Gly Ser Leu Arg Phe Ser Phe Met

-continued

```
            435                 440                 445
Phe Cys Gly Thr Ala Asn Thr Thr Leu Lys Val Leu Ala Tyr Thr
450                 455                 460
Pro Pro Gly Ile Gly Lys Pro Arg Ser Arg Lys Glu Ala Met Leu Gly
465                 470                 475                 480
Thr His Val Val Trp Asp Val Gly Leu Gln Ser Thr Val Ser Leu Val
                    485                 490                 495
Val Pro Trp Ile Ser Ala Ser Gln Tyr Arg Phe Thr Thr Pro Asp Thr
                500                 505                 510
Tyr Ser Ser Ala Gly Tyr Ile Thr Cys Trp Tyr Gln Thr Asn Phe Val
            515                 520                 525
Val Pro Pro Asn Thr Pro Asn Thr Ala Glu Met Leu Cys Phe Val Ser
530                 535                 540
Gly Cys Asn His Phe Cys Leu Arg Met Ala Arg Asp Thr Asp Leu His
545                 550                 555                 560
Lys Gln Thr Gly Pro Ile Thr Gln Asn Pro Val Glu Arg Tyr Val Asp
                565                 570                 575
Glu Val Leu Asn Glu Val Leu Val Pro Asn Ile Asn Gln Ser His
                580                 585                 590
Pro Thr Thr Ser Asn Ala Ala Pro Val Leu Asp Ala Ala Glu Thr Gly
                595                 600                 605
His Thr Asn Lys Ile Gln Pro Glu Asp Thr Ile Glu Thr Arg Tyr Val
610                 615                 620
Gln Ser Ser Gln Thr Leu Asp Glu Met Ser Val Glu Ser Phe Leu Gly
625                 630                 635                 640
Arg Ser Gly Cys Ile His Glu Ser Val Leu Asp Ile Val Asp Asn Tyr
                645                 650                 655
Asn Asp Gln Ser Phe Thr Lys Trp Asn Ile Asn Leu Gln Glu Met Ala
                660                 665                 670
Gln Ile Arg Arg Lys Phe Glu Met Phe Thr Tyr Ala Arg Phe Asp Ser
            675                 680                 685
Glu Ile Thr Met Val Pro Ser Val Ala Ala Lys Asp Gly His Ile Gly
690                 695                 700
His Ile Val Met Gln Tyr Met Tyr Val Pro Pro Gly Ala Pro Ile Pro
705                 710                 715                 720
Thr Thr Arg Asp Asp Tyr Ala Trp Gln Ser Gly Thr Asn Ala Ser Val
                725                 730                 735
Phe Trp Gln His Gly Gln Pro Phe Pro Arg Phe Ser Leu Pro Phe Leu
                740                 745                 750
Ser Ile Ala Ser Ala Tyr Tyr Met Phe Tyr Asp Gly Tyr Asp Gly Asp
            755                 760                 765
Thr Tyr Lys Ser Arg Tyr Gly Thr Val Val Thr Asn Asp Met Gly Thr
        770                 775                 780
Leu Cys Ser Arg Ile Val Thr Ser Glu Gln Leu His Lys Val Lys Val
785                 790                 795                 800
Val Thr Arg Ile Tyr His Lys Ala Lys His Thr Lys Ala Trp Cys Pro
                805                 810                 815
Arg Pro Pro Arg Ala Val Gln Tyr Ser His Thr His Thr Thr Asn Tyr
            820                 825                 830
Lys Leu Ser Ser Glu Val His Asn Asp Val Ala Ile Arg Pro Arg Thr
            835                 840                 845
Asn Leu Thr Thr Val Gly Pro Ser Asp Met Tyr
850                 855
```

<210> SEQ ID NO 69
<211> LENGTH: 859
<212> TYPE: PRT
<213> ORGANISM: Human rhinovirus

<400> SEQUENCE: 69

```
Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
                20                  25                  30

Phe Lys Asp Ala Ala Ser Ser Gly Ala Ser Arg Leu Asp Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Asp Ser Lys Met Trp Asn Ser Thr Ser
    130                 135                 140

Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
        195                 200                 205

Val Asn Ala Gly Tyr Lys Tyr Thr His Pro Gly Glu Ala Gly Arg Glu
    210                 215                 220

Val Gly Thr Gln Val Glu Asn Glu Lys Gln Pro Ser Asp Asp Asn Trp
225                 230                 235                 240

Leu Asn Phe Asp Gly Thr Leu Leu Gly Asn Leu Leu Ile Phe Pro His
                245                 250                 255

Gln Phe Ile Asn Leu Arg Ser Asn Asn Ser Ala Thr Leu Ile Val Pro
            260                 265                 270

Tyr Val Asn Ala Val Pro Met Asp Ser Met Val Arg His Asn Asn Trp
        275                 280                 285

Ser Leu Val Ile Ile Pro Val Cys Gln Leu Gln Ser Asn Asn Ile Ser
    290                 295                 300

Asn Ile Val Pro Ile Thr Val Ser Ile Ser Pro Met Cys Ala Glu Phe
305                 310                 315                 320

Ser Gly Ala Arg Ala Lys Thr Val Val Gln Gly Leu Pro Val Tyr Val
                325                 330                 335

Thr Pro Gly Ser Gly Gln Phe Met Thr Thr Asp Asp Met Gln Ser Pro
            340                 345                 350

Cys Ala Leu Pro Trp Tyr His Pro Thr Lys Glu Ile Phe Ile Pro Gly
        355                 360                 365

Glu Val Lys Asn Leu Ile Glu Met Cys Gln Val Asp Thr Leu Ile Pro
```

```
              370                 375                 380
Ile Asn Ser Thr Gln Ser Ala Ile Gly Asn Val Ser Met Tyr Thr Val
385                 390                 395                 400

Thr Leu Ser Pro Gln Thr Lys Leu Ala Glu Glu Ile Phe Ala Ile Lys
                405                 410                 415

Val Asp Ile Ala Ser His Pro Leu Ala Thr Thr Leu Ile Gly Glu Ile
                420                 425                 430

Ala Ser Tyr Phe Thr His Trp Thr Gly Ser Leu Arg Phe Ser Phe Met
            435                 440                 445

Phe Cys Gly Thr Ala Asn Thr Thr Leu Lys Val Leu Leu Ala Tyr Thr
        450                 455                 460

Pro Pro Gly Ile Gly Lys Pro Arg Ser Arg Lys Glu Ala Met Leu Gly
465                 470                 475                 480

Thr His Val Val Trp Asp Val Gly Leu Gln Ser Thr Val Ser Leu Val
                485                 490                 495

Val Pro Trp Ile Ser Ala Ser Gln Tyr Arg Phe Thr Thr Pro Asp Thr
                500                 505                 510

Tyr Ser Ser Ala Gly Tyr Ile Thr Cys Trp Tyr Gln Thr Asn Phe Val
            515                 520                 525

Val Pro Pro Asn Thr Pro Asn Thr Ala Glu Met Leu Cys Phe Val Ser
        530                 535                 540

Gly Cys Asn His Phe Cys Leu Arg Met Ala Arg Asp Thr Asp Leu His
545                 550                 555                 560

Lys Gln Thr Gly Pro Ile Thr Gln Asn Pro Val Glu Arg Tyr Val Asp
                565                 570                 575

Glu Val Leu Asn Glu Val Leu Val Val Pro Asn Ile Asn Gln Ser His
                580                 585                 590

Pro Thr Thr Ser Asn Ala Ala Pro Val Leu Asp Ala Ala Glu Thr Gly
            595                 600                 605

His Thr Asn Lys Ile Gln Pro Glu Asp Thr Ile Glu Thr Arg Tyr Val
        610                 615                 620

Gln Ser Ser Gln Thr Leu Asp Glu Met Ser Val Glu Ser Phe Leu Gly
625                 630                 635                 640

Arg Ser Gly Cys Ile His Glu Ser Val Leu Asp Ile Val Asp Asn Tyr
                645                 650                 655

Asn Asp Gln Ser Phe Thr Lys Trp Asn Ile Asn Leu Gln Glu Met Ala
            660                 665                 670

Gln Ile Arg Arg Lys Phe Glu Met Phe Thr Tyr Ala Arg Phe Asp Ser
        675                 680                 685

Glu Ile Thr Met Val Pro Ser Val Ala Ala Lys Asp Gly His Ile Gly
        690                 695                 700

His Ile Val Met Gln Tyr Met Tyr Val Pro Pro Gly Ala Pro Ile Pro
705                 710                 715                 720

Thr Thr Arg Asp Asp Tyr Ala Trp Gln Ser Gly Thr Asn Ala Ser Val
                725                 730                 735

Phe Trp Gln His Gly Gln Pro Phe Pro Arg Phe Ser Leu Pro Phe Leu
            740                 745                 750

Ser Ile Ala Ser Ala Tyr Tyr Met Phe Tyr Asp Gly Tyr Asp Gly Asp
        755                 760                 765

Thr Tyr Lys Ser Arg Tyr Gly Thr Val Val Thr Asn Asp Met Gly Thr
    770                 775                 780

Leu Cys Ser Arg Ile Val Thr Ser Glu Gln Leu His Lys Val Lys Val
785                 790                 795                 800
```

```
Val Thr Arg Ile Tyr His Lys Ala Lys His Thr Lys Ala Trp Cys Pro
                805                 810                 815

Arg Pro Pro Arg Ala Val Gln Tyr Ser His Thr His Thr Thr Asn Tyr
            820                 825                 830

Lys Leu Ser Ser Glu Val His Asn Asp Val Ala Ile Arg Pro Arg Thr
        835                 840                 845

Asn Leu Thr Thr Val Gly Pro Ser Asp Met Tyr
        850                 855

<210> SEQ ID NO 70
<211> LENGTH: 859
<212> TYPE: PRT
<213> ORGANISM: Human rhinovirus

<400> SEQUENCE: 70

Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Asp Ser Lys Met Trp Asn Ser Thr Ser
    130                 135                 140

Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
        195                 200                 205

Val Asn Ala Gly Tyr Lys Tyr Thr His Pro Gly Glu Ala Gly Arg Glu
    210                 215                 220

Val Gly Thr Gln Val Glu Asn Glu Lys Gln Pro Ser Asp Asp Asn Trp
225                 230                 235                 240

Leu Asn Phe Asp Gly Thr Leu Leu Gly Asn Leu Leu Ile Phe Pro His
                245                 250                 255

Gln Phe Ile Asn Leu Arg Ser Asn Asn Ser Ala Thr Leu Ile Val Pro
            260                 265                 270

Tyr Val Asn Ala Val Pro Met Asp Ser Met Val Arg His Asn Asn Trp
        275                 280                 285

Ser Leu Val Ile Ile Pro Val Cys Gln Leu Gln Ser Asn Asn Ile Ser
    290                 295                 300

Asn Ile Val Pro Ile Thr Val Ser Ile Ser Pro Met Cys Ala Glu Phe
```

```
            305                 310                 315                 320
        Ser Gly Arg Ala Lys Thr Val Val Gln Gly Leu Pro Val Tyr Val
                        325                 330                 335

Thr Pro Gly Ser Gly Gln Phe Met Thr Thr Asp Asp Met Gln Ser Pro
                        340                 345                 350

Cys Ala Leu Pro Trp Tyr His Pro Thr Lys Glu Ile Phe Ile Pro Gly
                        355                 360                 365

Glu Val Lys Asn Leu Ile Glu Met Cys Gln Val Asp Thr Leu Ile Pro
                        370                 375                 380

Ile Asn Ser Thr Gln Ser Asn Ile Gly Asn Val Ser Met Tyr Thr Val
        385                 390                 395                 400

Thr Leu Ser Pro Gln Thr Lys Leu Ala Glu Glu Ile Phe Ala Ile Lys
                        405                 410                 415

Val Asp Ile Ala Ser His Pro Leu Ala Thr Thr Leu Ile Gly Glu Ile
                        420                 425                 430

Ala Ser Tyr Phe Thr His Trp Thr Gly Ser Leu Arg Phe Ser Phe Met
                        435                 440                 445

Phe Cys Gly Thr Ala Asn Thr Thr Leu Lys Val Leu Leu Ala Tyr Thr
        450                 455                 460

Pro Pro Gly Ile Gly Lys Pro Arg Ser Arg Lys Glu Ala Met Leu Gly
        465                 470                 475                 480

Thr His Val Val Trp Asp Val Gly Leu Gln Ser Thr Val Ser Leu Val
                        485                 490                 495

Val Pro Trp Ile Ser Ala Ser Gln Tyr Arg Phe Thr Thr Pro Asp Thr
                        500                 505                 510

Tyr Ser Ser Ala Gly Tyr Ile Thr Cys Trp Tyr Gln Thr Asn Phe Val
                        515                 520                 525

Val Pro Pro Asn Thr Pro Asn Thr Ala Glu Met Leu Cys Phe Val Ser
                        530                 535                 540

Gly Cys Asn His Phe Cys Leu Arg Met Ala Arg Asp Thr Asp Leu His
        545                 550                 555                 560

Lys Gln Thr Gly Pro Ile Thr Gln Asn Pro Val Glu Arg Tyr Val Asp
                        565                 570                 575

Glu Val Leu Asn Glu Val Leu Val Pro Asn Ile Asn Gln Ser His
                        580                 585                 590

Pro Thr Thr Ser Asn Ala Ala Pro Val Leu Asp Ala Ala Glu Thr Gly
                        595                 600                 605

His Thr Asn Lys Ile Gln Pro Glu Asp Thr Ile Glu Thr Arg Tyr Val
                        610                 615                 620

Gln Ser Ser Gln Thr Leu Asp Glu Met Ser Val Glu Ser Phe Leu Gly
        625                 630                 635                 640

Arg Ser Gly Cys Ile His Glu Ser Val Leu Ala Ile Val Ala Asn Tyr
                        645                 650                 655

Asn Gly Ala Ser Phe Thr Ala Trp Asn Ile Asn Leu Gln Glu Met Ala
                        660                 665                 670

Gln Ile Arg Arg Lys Phe Glu Met Phe Thr Tyr Ala Arg Phe Asp Ser
                        675                 680                 685

Glu Ile Thr Met Val Pro Ser Val Ala Ala Lys Asp Gly His Ile Gly
                        690                 695                 700

His Ile Val Met Gln Tyr Met Tyr Val Pro Pro Gly Ala Pro Ile Pro
        705                 710                 715                 720

Thr Thr Arg Asp Asp Tyr Ala Trp Gln Ser Gly Thr Asn Ala Ser Val
                        725                 730                 735
```

```
Phe Trp Gln His Gly Gln Pro Phe Pro Arg Phe Ser Leu Pro Phe Leu
            740                 745                 750

Ser Ile Ala Ser Ala Tyr Tyr Met Phe Tyr Asp Gly Tyr Asp Gly Asp
            755                 760                 765

Thr Tyr Lys Ser Arg Tyr Gly Thr Val Val Thr Asn Asp Met Gly Thr
            770                 775                 780

Leu Cys Ser Arg Ile Val Thr Ser Glu Gln Leu His Lys Val Lys Val
785                 790                 795                 800

Val Thr Arg Ile Tyr His Lys Ala Lys His Thr Lys Ala Trp Cys Pro
                805                 810                 815

Arg Pro Pro Arg Ala Val Gln Tyr Ser His Thr His Thr Thr Asn Tyr
            820                 825                 830

Lys Leu Ser Ser Glu Val His Asn Asp Val Ala Ile Arg Pro Arg Thr
            835                 840                 845

Asn Leu Thr Thr Val Gly Pro Ser Asp Met Tyr
            850                 855
```

<210> SEQ ID NO 71
<211> LENGTH: 859
<212> TYPE: PRT
<213> ORGANISM: Human rhinovirus

<400> SEQUENCE: 71

```
Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
            35                  40                  45

Asp Pro Ser Lys Phe Thr Asp Pro Val Lys Asp Val Leu Glu Lys Gly
            50                  55                  60

Ile Pro Thr Leu Gln Ser Pro Ser Val Glu Ala Cys Gly Tyr Ser Asp
65              70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
            115                 120                 125

Ser Asn Arg Phe Tyr Thr Leu Asp Ser Lys Met Trp Asn Ser Thr Ser
            130                 135                 140

Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Val Met Ile Pro Glu His Gln Leu Ala Thr Val Asn Lys Gly Asn
            195                 200                 205

Val Asn Ala Gly Tyr Lys Tyr Thr His Pro Gly Glu Ala Gly Arg Glu
            210                 215                 220

Val Gly Thr Gln Val Glu Asn Glu Lys Gln Pro Ser Asp Asp Asn Trp
225                 230                 235                 240

Leu Asn Phe Asp Gly Thr Leu Leu Gly Asn Leu Leu Ile Phe Pro His
```

```
            245                 250                 255
Gln Phe Ile Asn Leu Arg Ser Asn Ser Ala Thr Leu Ile Val Pro
            260                 265                 270
Tyr Val Asn Ala Val Pro Met Asp Ser Met Val Arg His Asn Asn Trp
            275                 280                 285
Ser Leu Val Ile Ile Pro Val Cys Gln Leu Gln Ser Asn Asn Ile Ser
            290                 295                 300
Asn Ile Val Pro Ile Thr Val Ser Ile Ser Pro Met Cys Ala Glu Phe
305                 310                 315                 320
Ser Gly Ala Arg Ala Lys Thr Val Gln Gly Leu Pro Val Tyr Val
                325                 330                 335
Thr Pro Gly Ser Gly Gln Phe Met Thr Thr Asp Asp Met Gln Ser Pro
            340                 345                 350
Cys Ala Leu Pro Trp Tyr His Pro Thr Lys Glu Ile Phe Ile Pro Gly
                355                 360                 365
Glu Val Lys Asn Leu Ile Glu Met Cys Gln Val Asp Thr Leu Ile Pro
            370                 375                 380
Ile Asn Ser Thr Gln Ser Asn Ile Gly Asn Val Ser Met Tyr Thr Val
385                 390                 395                 400
Thr Leu Ser Pro Gln Thr Lys Leu Ala Glu Glu Ile Phe Ala Ile Lys
                405                 410                 415
Val Asp Ile Ala Ser His Pro Leu Ala Thr Thr Leu Ile Gly Glu Ile
                420                 425                 430
Ala Ser Tyr Phe Thr His Trp Thr Gly Ser Leu Arg Phe Ser Phe Met
            435                 440                 445
Phe Cys Gly Thr Ala Asn Thr Thr Leu Lys Val Leu Leu Ala Tyr Thr
450                 455                 460
Pro Pro Gly Ile Gly Lys Pro Arg Ser Arg Lys Glu Ala Met Leu Gly
465                 470                 475                 480
Thr His Val Val Trp Asp Val Gly Leu Gln Ser Thr Val Ser Leu Val
                485                 490                 495
Val Pro Trp Ile Ser Ala Ser Gln Tyr Arg Phe Thr Thr Pro Asp Thr
            500                 505                 510
Tyr Ser Ser Ala Gly Tyr Ile Thr Cys Trp Tyr Gln Thr Asn Phe Val
            515                 520                 525
Val Pro Pro Asn Thr Pro Asn Thr Ala Glu Met Leu Cys Phe Val Ser
            530                 535                 540
Gly Cys Asn His Phe Cys Leu Arg Met Ala Arg Asp Thr Asp Leu His
545                 550                 555                 560
Lys Gln Thr Gly Pro Ile Thr Gln Asn Pro Val Glu Arg Tyr Val Asp
                565                 570                 575
Glu Val Leu Asn Glu Val Leu Val Pro Asn Ile Asn Gln Ser His
            580                 585                 590
Pro Thr Thr Ser Asn Ala Ala Pro Val Leu Asp Ala Ala Glu Thr Gly
                595                 600                 605
His Thr Asn Lys Ile Gln Pro Glu Asp Thr Ile Glu Thr Arg Tyr Val
            610                 615                 620
Gln Ser Ser Gln Thr Leu Asp Glu Met Ser Val Glu Ser Phe Leu Gly
625                 630                 635                 640
Arg Ser Gly Cys Ile His Glu Ser Val Leu Asp Ile Val Asp Asn Tyr
                645                 650                 655
Asn Asp Gln Ser Phe Thr Lys Trp Asn Ile Asn Leu Gln Glu Met Ala
            660                 665                 670
```

```
Gln Ile Arg Arg Lys Phe Glu Met Phe Thr Tyr Ala Arg Phe Asp Ser
                675                 680                 685

Glu Ile Thr Met Val Pro Ser Val Ala Ala Lys Asp Gly His Ile Gly
690                 695                 700

His Ile Val Met Gln Tyr Met Tyr Val Pro Pro Gly Ala Pro Ile Pro
705                 710                 715                 720

Thr Thr Arg Asp Asp Tyr Ala Trp Gln Ser Gly Thr Asn Ala Ser Val
                725                 730                 735

Phe Trp Gln His Gly Gln Pro Phe Pro Arg Phe Ser Leu Pro Phe Leu
                740                 745                 750

Ser Ile Ala Ser Ala Tyr Tyr Met Phe Tyr Asp Gly Tyr Asp Gly Asp
                755                 760                 765

Thr Tyr Lys Ser Arg Tyr Gly Thr Val Val Thr Asn Asp Met Gly Thr
770                 775                 780

Leu Cys Ser Arg Ile Val Thr Ala Gly Ala Leu His Ala Val Ala Val
785                 790                 795                 800

Val Thr Arg Ile Tyr His Lys Ala Lys His Thr Lys Ala Trp Cys Pro
                805                 810                 815

Arg Pro Pro Arg Ala Val Gln Tyr Ser His Thr His Thr Asn Tyr
                820                 825                 830

Lys Leu Ser Ser Glu Val His Asn Asp Val Ala Ile Arg Pro Arg Thr
835                 840                 845

Asn Leu Thr Thr Val Gly Pro Ser Asp Met Tyr
850                 855
```

```
<210> SEQ ID NO 72
<211> LENGTH: 859
<212> TYPE: PRT
<213> ORGANISM: Human rhinovirus

<400> SEQUENCE: 72

Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
                20                  25                  30

Phe Lys Asp Ala Ala Ser Ser Gly Ala Ser Arg Leu Asp Phe Ser Gln
                35                  40                  45

Asp Pro Ser Lys Phe Thr Asp Pro Val Lys Asp Val Leu Glu Lys Gly
            50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
                100                 105                 110

Pro Gln Asp Ala Thr Ala Ile Asp Lys Pro Thr Gln Pro Asp Thr Ser
            115                 120                 125

Ser Asn Arg Phe Tyr Thr Leu Asp Ser Lys Met Trp Asn Ser Thr Ser
        130                 135                 140

Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
```

```
            180                 185                 190
Val Val Met Ile Pro Glu His Gln Leu Ala Thr Val Asn Lys Gly Asn
            195                 200                 205
Val Asn Ala Gly Tyr Lys Tyr Thr His Pro Gly Glu Ala Gly Arg Glu
            210                 215                 220
Val Gly Thr Gln Val Glu Asn Glu Lys Gln Pro Ser Asp Asp Asn Trp
225                 230                 235                 240
Leu Asn Phe Asp Gly Thr Leu Leu Gly Asn Leu Leu Ile Phe Pro His
            245                 250                 255
Gln Phe Ile Asn Leu Arg Ser Asn Asn Ser Ala Thr Leu Ile Val Pro
            260                 265                 270
Tyr Val Asn Ala Val Pro Met Asp Ser Met Val Arg His Asn Asn Trp
            275                 280                 285
Ser Leu Val Ile Ile Pro Val Cys Gln Leu Gln Ser Asn Asn Ile Ser
            290                 295                 300
Asn Ile Val Pro Ile Thr Val Ser Ile Ser Pro Met Cys Ala Glu Phe
305                 310                 315                 320
Ser Gly Ala Arg Ala Lys Thr Val Val Gln Gly Leu Pro Val Tyr Val
            325                 330                 335
Thr Pro Gly Ser Gly Gln Phe Met Thr Thr Asp Asp Met Gln Ser Pro
            340                 345                 350
Cys Ala Leu Pro Trp Tyr His Pro Thr Lys Glu Ile Phe Ile Pro Gly
            355                 360                 365
Glu Val Lys Asn Leu Ile Glu Met Cys Gln Val Asp Thr Leu Ile Pro
            370                 375                 380
Ile Asn Ser Thr Gln Ser Asn Ile Gly Asn Val Ser Met Tyr Thr Val
385                 390                 395                 400
Thr Leu Ser Pro Gln Thr Lys Leu Ala Glu Glu Ile Phe Ala Ile Lys
            405                 410                 415
Val Asp Ile Ala Ser His Pro Leu Ala Thr Thr Leu Ile Gly Glu Ile
            420                 425                 430
Ala Ser Tyr Phe Thr His Trp Thr Gly Ser Leu Arg Phe Ser Phe Met
            435                 440                 445
Phe Cys Gly Thr Ala Asn Thr Thr Leu Lys Val Leu Leu Ala Tyr Thr
            450                 455                 460
Pro Pro Gly Ile Gly Lys Pro Arg Ser Arg Lys Glu Ala Met Leu Gly
465                 470                 475                 480
Thr His Val Val Trp Asp Val Gly Leu Gln Ser Thr Val Ser Leu Val
            485                 490                 495
Val Pro Trp Ile Ser Ala Ser Gln Tyr Arg Phe Thr Thr Pro Asp Thr
            500                 505                 510
Tyr Ser Ser Ala Gly Tyr Ile Thr Cys Trp Tyr Gln Thr Asn Phe Val
            515                 520                 525
Val Pro Pro Asn Thr Pro Asn Thr Ala Glu Met Leu Cys Phe Val Ser
            530                 535                 540
Gly Cys Asn His Phe Cys Leu Arg Met Ala Arg Asp Thr Asp Leu His
545                 550                 555                 560
Lys Gln Thr Gly Pro Ile Thr Gln Asn Pro Val Glu Arg Tyr Val Asp
            565                 570                 575
Glu Val Leu Asn Glu Val Leu Val Pro Asn Ile Asn Gln Ser His
            580                 585                 590
Pro Thr Thr Ser Asn Ala Ala Pro Val Leu Asp Ala Ala Glu Thr Gly
            595                 600                 605
```

His Thr Asn Lys Ile Gln Pro Glu Asp Thr Ile Glu Thr Arg Tyr Val
610                 615                 620

Gln Ser Ser Gln Thr Leu Asp Glu Met Ser Val Glu Ser Phe Leu Gly
625                 630                 635                 640

Arg Ser Gly Cys Ile His Glu Ser Val Leu Asp Ile Val Asp Asn Tyr
            645                 650                 655

Asn Asp Gln Ser Phe Thr Lys Trp Asn Ile Asn Leu Gln Glu Met Ala
            660                 665                 670

Gln Ile Arg Arg Lys Phe Glu Met Phe Thr Tyr Ala Arg Phe Asp Ser
            675                 680                 685

Glu Ile Thr Met Val Pro Ser Val Ala Ala Lys Asp Gly His Ile Gly
            690                 695                 700

His Ile Val Met Gln Tyr Met Tyr Val Pro Pro Gly Ala Pro Ile Pro
705                 710                 715                 720

Thr Thr Arg Asp Asp Tyr Ala Trp Gln Ser Gly Thr Asn Ala Ser Val
            725                 730                 735

Phe Trp Gln His Gly Gln Pro Phe Pro Arg Phe Ser Leu Pro Phe Leu
            740                 745                 750

Ser Ile Ala Ser Ala Tyr Tyr Met Phe Tyr Asp Gly Tyr Asp Gly Asp
            755                 760                 765

Thr Tyr Lys Ser Arg Tyr Gly Thr Val Val Thr Asn Asp Met Gly Thr
770                 775                 780

Leu Cys Ser Arg Ile Val Thr Ser Glu Gln Leu His Lys Val Lys Val
785                 790                 795                 800

Val Thr Arg Ile Tyr His Lys Ala Lys His Thr Lys Ala Trp Cys Pro
            805                 810                 815

Arg Pro Pro Arg Ala Val Gln Tyr Ser His Thr His Thr Thr Asn Tyr
            820                 825                 830

Ala Leu Ser Val Gln Val His Asn Asp Val Ala Ile Arg Pro Arg Thr
            835                 840                 845

Asn Leu Thr Thr Val Gly Pro Ser Asp Met Tyr
850                 855

<210> SEQ ID NO 73
<211> LENGTH: 859
<212> TYPE: PRT
<213> ORGANISM: Human rhinovirus

<400> SEQUENCE: 73

Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser

-continued

```
            115                 120                 125
Ser Asn Arg Phe Tyr Thr Leu Asp Ser Lys Met Trp Asn Ser Thr Ser
130                 135                 140
Lys Gly Trp Trp Lys Leu Pro Asp Ala Leu Lys Asp Met Gly Ile
145                 150                 155                 160
Phe Gly Glu Asn Met Phe Tyr His Phe Leu Gly Arg Ser Gly Tyr Thr
                    165                 170                 175
Val His Val Gln Cys Asn Ala Ser Lys Phe His Gln Gly Thr Leu Leu
                180                 185                 190
Val Val Met Ile Pro Glu His Gln Leu Ala Thr Val Asn Lys Gly Asn
            195                 200                 205
Val Asn Ala Gly Tyr Lys Tyr Thr His Pro Gly Glu Ala Gly Arg Glu
210                 215                 220
Val Gly Thr Gln Val Glu Asn Glu Lys Gln Pro Ser Asp Asp Asn Trp
225                 230                 235                 240
Leu Asn Phe Asp Gly Thr Leu Leu Gly Asn Leu Leu Ile Phe Pro His
                    245                 250                 255
Gln Phe Ile Asn Leu Arg Ser Asn Asn Ser Ala Thr Leu Ile Val Pro
                260                 265                 270
Tyr Val Asn Ala Val Pro Met Asp Ser Met Val Arg His Asn Asn Trp
            275                 280                 285
Ser Leu Val Ile Ile Pro Val Cys Gln Leu Gln Ser Asn Asn Ile Ser
290                 295                 300
Asn Ile Val Pro Ile Thr Val Ser Ile Ser Pro Met Cys Ala Glu Phe
305                 310                 315                 320
Ser Gly Ala Arg Ala Lys Thr Val Val Gln Gly Leu Pro Val Tyr Val
                    325                 330                 335
Thr Pro Gly Ser Gly Gln Phe Met Thr Thr Asp Asp Met Gln Ser Pro
                340                 345                 350
Cys Ala Leu Pro Trp Tyr His Pro Thr Lys Glu Ile Phe Ile Pro Gly
            355                 360                 365
Glu Val Lys Asn Leu Ile Glu Met Cys Gln Val Asp Thr Leu Ile Pro
370                 375                 380
Ile Asn Ser Thr Gln Ser Asn Ile Gly Asn Val Ser Met Tyr Thr Val
385                 390                 395                 400
Thr Leu Ser Pro Gln Thr Lys Leu Ala Glu Glu Ile Phe Ala Ile Lys
                    405                 410                 415
Val Asp Ile Ala Ser His Pro Leu Ala Thr Thr Leu Ile Gly Glu Ile
                420                 425                 430
Ala Ser Tyr Phe Thr His Trp Thr Gly Ser Leu Arg Phe Ser Phe Met
            435                 440                 445
Phe Cys Gly Thr Ala Asn Thr Thr Leu Lys Val Leu Leu Ala Tyr Thr
450                 455                 460
Pro Pro Gly Ile Gly Lys Pro Arg Ser Arg Lys Glu Ala Met Leu Gly
465                 470                 475                 480
Thr His Val Val Trp Asp Val Gly Leu Gln Ser Thr Val Ser Leu Val
                    485                 490                 495
Val Pro Trp Ile Ser Ala Ser Gln Tyr Arg Phe Thr Thr Pro Asp Thr
                500                 505                 510
Tyr Ser Ser Ala Gly Tyr Ile Thr Cys Trp Tyr Gln Thr Asn Phe Val
            515                 520                 525
Val Pro Pro Asn Thr Pro Asn Thr Ala Glu Met Leu Cys Phe Val Ser
530                 535                 540
```

-continued

Gly Cys Asn His Phe Cys Leu Arg Met Ala Arg Asp Thr Asp Leu His
545                 550                 555                 560

Lys Gln Thr Gly Pro Ile Thr Gln Asn Pro Val Glu Arg Tyr Val Asp
                565                 570                 575

Glu Val Leu Asn Glu Val Leu Val Val Pro Asn Ile Asn Gln Ser His
            580                 585                 590

Pro Thr Thr Ser Asn Ala Ala Pro Val Leu Asp Ala Ala Glu Thr Gly
        595                 600                 605

His Thr Asn Lys Ile Gln Pro Glu Asp Thr Ile Glu Thr Arg Tyr Val
    610                 615                 620

Gln Ser Ser Gln Thr Leu Asp Glu Met Ser Val Glu Ser Phe Leu Gly
625                 630                 635                 640

Arg Ser Gly Cys Ile His Glu Ser Val Leu Asp Ile Val Asp Asn Tyr
                645                 650                 655

Asn Asp Gln Ser Phe Thr Lys Trp Asn Ile Asn Leu Gln Glu Met Ala
            660                 665                 670

Gln Ile Arg Arg Lys Phe Glu Met Phe Thr Tyr Ala Arg Phe Asp Ser
        675                 680                 685

Glu Ile Thr Met Val Pro Ser Val Ala Ala Lys Asp Gly His Ile Gly
690                 695                 700

His Ile Val Met Gln Tyr Met Tyr Val Pro Pro Gly Ala Pro Ile Pro
705                 710                 715                 720

Thr Thr Arg Asp Asp Tyr Ala Trp Gln Ser Gly Thr Asn Ala Ser Val
                725                 730                 735

Phe Trp Gln His Gly Gln Pro Phe Pro Arg Phe Ser Leu Pro Phe Leu
            740                 745                 750

Ser Ile Ala Ser Ala Tyr Tyr Met Phe Tyr Asp Gly Tyr Asp Gly Asp
        755                 760                 765

Thr Tyr Lys Ser Arg Tyr Gly Thr Val Val Thr Asn Asp Met Gly Thr
770                 775                 780

Leu Cys Ser Arg Ile Val Thr Ser Glu Gln Leu His Lys Val Lys Val
785                 790                 795                 800

Val Thr Arg Ile Tyr His Lys Ala Lys His Thr Lys Ala Trp Cys Pro
                805                 810                 815

Arg Pro Pro Arg Ala Val Gln Tyr Ser His Thr His Thr Thr Asn Tyr
            820                 825                 830

Lys Leu Ser Ser Glu Val His Asn Asp Val Ala Ile Ala Pro Ala Thr
        835                 840                 845

Asn Leu Thr Thr Val Gly Pro Ser Asp Met Tyr
    850                 855

<210> SEQ ID NO 74
<211> LENGTH: 863
<212> TYPE: PRT
<213> ORGANISM: Human rhinovirus

<400> SEQUENCE: 74

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
                20                  25                  30

Phe Lys Asp Ala Ala Ser Ser Gly Ala Ser Lys Leu Glu Phe Ser Gln
            35                  40                  45

Asp Pro Ser Lys Phe Thr Asp Pro Val Lys Asp Val Leu Glu Lys Gly

```
              50                  55                  60
Ile Pro Thr Leu Gln Ser Pro Thr Val Glu Ala Cys Gly Tyr Ser Asp
 65                  70                  75                  80

Arg Ile Ile Gln Ile Thr Arg Gly Asp Ser Thr Ile Thr Ser Gln Asp
                     85                  90                  95

Val Ala Asn Ala Val Val Gly Tyr Gly Val Trp Pro His Tyr Leu Thr
                100                 105                 110

Ala Asp Asp Ala Ser Ala Ile Asp Lys Pro Thr Gln Pro Asp Thr Ser
            115                 120                 125

Ser Asn Arg Phe Tyr Thr Leu Glu Ser Lys Val Trp Lys Arg Asp Ser
        130                 135                 140

Lys Gly Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480
```

```
Ala Met Leu Gly Thr His Ile Val Trp Asp Ile Gly Leu Gln Ser Thr
            485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
            515                 520                 525

Thr Asn Phe Val Phe Pro Pro Asn Thr Pro Asn Asn Ala Asn Met Ile
            530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
            565                 570                 575

Asn Tyr Ile Asp Glu Val Leu Asn Glu Val Leu Val Pro Asn Ile
            580                 585                 590

Arg Glu Ser His Pro Thr Thr Ser Asn Ala Ala Thr Ala Leu Asp Ala
            595                 600                 605

Ala Gly Thr Gly His Thr Ser Ser Ile Gln Pro Glu Asp Thr Ile Glu
            610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
            645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
            675                 680                 685

Val Arg Phe Asp Ser Glu Ile Thr Leu Val Pro Cys Ile Ala Gly Arg
            690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
            725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
            755                 760                 765

Gly Tyr Asp Gly Asp Lys Ser Ser Arg Tyr Gly Val Ser Val Thr
            770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
            805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
            835                 840                 845

Lys Ser Arg Glu Asn Leu Thr Thr Ala Gly Pro Ser Asp Met Tyr
850                 855                 860

<210> SEQ ID NO 75
<211> LENGTH: 863
<212> TYPE: PRT
<213> ORGANISM: Human rhinovirus
```

<400> SEQUENCE: 75

```
Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
    290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
    370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415
```

```
Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
        515                 520                 525

Thr Asn Phe Val Phe Pro Pro Asn Thr Pro Asn Asn Ala Asn Met Ile
530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
        595                 600                 605

Ala Gly Thr Gly His Thr Ser Ser Ile Gln Pro Glu Asp Thr Ile Glu
610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830
```

```
Asn Val Thr Asn Tyr Lys Val Arg Asp Gly Glu Pro Thr Leu Phe Ile
            835                 840                 845

Lys Ser Arg Glu Asn Leu Thr Thr Ala Gly Pro Ser Asp Met Tyr
850                 855                 860

<210> SEQ ID NO 76
<211> LENGTH: 863
<212> TYPE: PRT
<213> ORGANISM: Human rhinovirus

<400> SEQUENCE: 76

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
    290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Ala Thr Gln Gly Leu
                325                 330                 335

Pro Val Tyr Met Thr Pro Gly Ser Gly Gln Phe Leu Thr Thr Asp Asp
            340                 345                 350
```

```
Leu Gln Ser Pro Ser Ala Leu Pro Trp Tyr His Pro Thr Lys Glu Ile
        355                 360                 365
Phe Ile Pro Gly Gln Val Arg Asn Leu Ile Glu Met Cys Gln Val Asp
    370                 375                 380
Thr Met Ile Pro Ile Asn Asn Thr Asn Glu Arg Ile Gly Asn Val Asn
385                 390                 395                 400
Met Tyr Thr Val Ser Leu Thr Ser Gln Thr Asn Thr Ala Glu Gln Ile
                405                 410                 415
Phe Ala Ile Lys Val Asp Ile Ala Ser Gln Pro Leu Ser Ser Thr Leu
            420                 425                 430
Ile Gly Glu Ile Ala Ser Tyr Tyr Thr His Trp Thr Gly Ser Leu Arg
        435                 440                 445
Phe Ser Phe Met Phe Cys Gly Thr Ala Asn Thr Thr Leu Lys Leu Leu
    450                 455                 460
Leu Ala Tyr Thr Pro Pro Gly Ile Asp Lys Pro Thr Thr Arg Lys Gln
465                 470                 475                 480
Ala Met Leu Gly Thr His Ile Val Trp Asp Ile Gly Leu Gln Ser Thr
                485                 490                 495
Val Ser Leu Val Val Pro Trp Val Ser Ala Ser His Phe Arg Tyr Thr
            500                 505                 510
Thr Pro Asp Thr Tyr Ser Met Ala Gly Tyr Ile Thr Cys Trp Tyr Gln
        515                 520                 525
Thr Asn Phe Val Phe Pro Pro Asn Thr Pro Asn Asn Ala Asn Met Ile
    530                 535                 540
Cys Phe Val Ser Gly Cys Lys Asp Phe Cys Leu Arg Met Ala Arg Asp
545                 550                 555                 560
Thr Asp Met His Val Gln Asn Val Pro Ile Thr Gln Asn Pro Val Glu
                565                 570                 575
Asn Tyr Ile Asp Glu Val Leu Asn Glu Val Leu Val Val Pro Asn Ile
            580                 585                 590
Arg Glu Ser His Pro Thr Thr Ser Asn Ala Ala Thr Ala Leu Asp Ala
        595                 600                 605
Ala Gly Thr Gly His Thr Ser Ser Ile Gln Pro Glu Asp Thr Ile Glu
    610                 615                 620
Thr Arg Tyr Val Gln Thr Ser His Thr Arg Asp Glu Met Ser Val Glu
625                 630                 635                 640
Ser Phe Leu Gly Arg Ser Gly Cys Ile His Ile Ser Thr Ile Thr Met
                645                 650                 655
Lys Lys Glu Asn Tyr Asn Asp Ala Asn Phe Val Asp Trp Lys Ile Thr
            660                 665                 670
Leu Gln Glu Met Ala Gln Val Arg Arg Lys Phe Glu Met Phe Thr Tyr
        675                 680                 685
Val Arg Phe Asp Ser Glu Ile Thr Leu Val Pro Cys Ile Ala Gly Arg
    690                 695                 700
Gly Glu Asp Ile Gly His Ile Val Met Gln Tyr Met Tyr Val Pro Pro
705                 710                 715                 720
Gly Ala Pro Val Pro Lys Lys Arg Asp Asp Tyr Thr Trp Gln Ser Gly
                725                 730                 735
Thr Asn Ala Ser Val Phe Trp Gln His Gly Gln Pro Tyr Pro Arg Phe
            740                 745                 750
Ser Leu Pro Phe Leu Ser Ile Ala Ser Ala Tyr Tyr Met Phe Tyr Asp
        755                 760                 765
```

```
Gly Tyr Asp Gly Asp Lys Ser Ser Arg Tyr Gly Val Ser Val Thr
        770                 775                 780
Asn Asp Met Gly Thr Leu Cys Thr Arg Ile Val Thr Asn Gln Gln Glu
785                 790                 795                 800
His Leu Val Glu Val Thr Thr Arg Val Tyr His Lys Ala Lys His Val
                    805                 810                 815
Lys Ala Trp Cys Pro Arg Ala Pro Arg Ala Val Pro Tyr Thr His Ser
                820                 825                 830
Asn Val Thr Asn Tyr Lys Val Arg Asp Gly Pro Thr Leu Phe Ile
                835                 840                 845
Lys Ser Arg Glu Asn Leu Thr Thr Ala Gly Pro Ser Asp Met Tyr
850                 855                 860

<210> SEQ ID NO 77
<211> LENGTH: 863
<212> TYPE: PRT
<213> ORGANISM: Human rhinovirus

<400> SEQUENCE: 77

Met Gly Ala Gln Val Ser Arg Gln Asn Val Gly Thr His Ser Thr Gln
1               5                   10                  15
Asn Ser Val Ser Gly Gly Ser Ser Leu Asn Tyr Phe Asn Ile Asn Tyr
                20                  25                  30
Phe Lys Asp Ala Ala Ser Ser Gly Ala Ser Lys Leu Glu Phe Ser Gln
            35                  40                  45
Asp Pro Ser Lys Phe Thr Asp Pro Val Lys Asp Val Leu Glu Lys Gly
        50                  55                  60
Ile Pro Thr Leu Gln Ser Pro Thr Val Glu Ala Cys Gly Tyr Ser Asp
65                  70                  75                  80
Arg Ile Ile Gln Ile Thr Arg Gly Asp Ser Thr Ile Thr Ser Gln Asp
                85                  90                  95
Val Ala Asn Ala Val Val Gly Tyr Gly Val Trp Pro His Tyr Leu Thr
            100                 105                 110
Ala Asp Asp Ala Ser Ala Ile Asp Lys Pro Thr Gln Pro Asp Thr Ser
        115                 120                 125
Ser Asn Arg Phe Tyr Thr Leu Glu Ser Lys Val Trp Lys Arg Asp Ser
130                 135                 140
Lys Gly Trp Trp Trp Lys Leu Pro Asp Ala Leu Lys Asp Met Gly Ile
145                 150                 155                 160
Phe Gly Glu Asn Met Tyr Tyr His Phe Leu Gly Arg Ser Gly Tyr Thr
                165                 170                 175
Val His Val Gln Cys Asn Ala Ser Lys Phe His Gln Gly Thr Leu Leu
            180                 185                 190
Ile Ala Met Val Pro Glu His Gln Leu Ala Ser Ala Asn Tyr Gly Asn
        195                 200                 205
Val Thr Ala Gly Tyr Asn Tyr Thr His Pro Gly Glu Ala Gly Arg Asp
    210                 215                 220
Val Gly Gln Gln Arg Ala Asn Asn Glu Lys Gln Pro Ser Asp Asp Asn
225                 230                 235                 240
Trp Leu Asn Phe Asp Gly Thr Leu Leu Gly Asn Leu Leu Ile Phe Pro
                245                 250                 255
His Gln Phe Ile Asn Leu Arg Ser Asn Asn Ser Ala Thr Ile Ile Val
            260                 265                 270
Pro Tyr Val Asn Ala Val Pro Met Asp Ser Met Leu Arg His Asn Asn
        275                 280                 285
```

```
Trp Ser Leu Leu Ile Ile Pro Val Ser Pro Leu Asp Ala Asp Thr Ser
            290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
            355                 360                 365

Phe Ile Pro Gly Gln Val Arg Asn Leu Ile Glu Met Cys Gln Val Asp
370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
            435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
            515                 520                 525

Thr Asn Phe Val Phe Pro Pro Asn Thr Pro Asn Asn Ala Asn Met Ile
            530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
            595                 600                 605

Ala Gly Thr Gly His Thr Ser Ser Ile Gln Pro Glu Asp Thr Ile Glu
610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Gln Asn Tyr Asn Gln His Asn Phe Val Asp Trp Lys Ile Thr
            660                 665                 670

Leu Gln Glu Met Ala Gln Val Arg Arg Lys Phe Glu Met Phe Thr Tyr
            675                 680                 685

Val Arg Phe Asp Ser Glu Ile Thr Leu Val Pro Cys Ile Ala Gly Arg
690                 695                 700
```

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
            725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
            755                 760                 765

Gly Tyr Asp Gly Asp Lys Ser Ser Arg Tyr Gly Val Ser Val Thr
            770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
            805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
            835                 840                 845

Lys Ser Arg Glu Asn Leu Thr Thr Ala Gly Pro Ser Asp Met Tyr
850                 855                 860

<210> SEQ ID NO 78
<211> LENGTH: 863
<212> TYPE: PRT
<213> ORGANISM: Human rhinovirus

<400> SEQUENCE: 78

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

```
Val Gly Gln Gln Arg Ala Asn Glu Lys Gln Pro Ser Asp Asp Asn
225                 230                 235                 240

Trp Leu Asn Phe Asp Gly Thr Leu Leu Gly Asn Leu Leu Ile Phe Pro
            245                 250                 255

His Gln Phe Ile Asn Leu Arg Ser Asn Ser Ala Thr Ile Ile Val
        260                 265                 270

Pro Tyr Val Asn Ala Val Pro Met Asp Ser Met Leu Arg His Asn Asn
    275                 280                 285

Trp Ser Leu Leu Ile Ile Pro Val Ser Pro Leu Asp Ala Asp Thr Ser
290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
            325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
            405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
            485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
        515                 520                 525

Thr Asn Phe Val Phe Pro Pro Asn Thr Pro Asn Asn Ala Asn Met Ile
        530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
            565                 570                 575

Asn Tyr Ile Asp Glu Val Leu Asn Glu Val Leu Val Pro Asn Ile
            580                 585                 590

Arg Glu Ser His Pro Thr Thr Ser Asn Ala Ala Thr Ala Leu Asp Ala
        595                 600                 605

Ala Gly Thr Gly His Thr Ser Ser Ile Gln Pro Glu Asp Thr Ile Glu
        610                 615                 620

Thr Arg Tyr Val Gln Thr Ser His Thr Arg Asp Glu Met Ser Val Glu
625                 630                 635                 640
```

-continued

```
Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
    770                 775                 780

Asn Asp Met Gly Thr Leu Cys Thr Arg Ile Val Thr Asn Gln Gln Ala
785                 790                 795                 800

His Leu Val Gln Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
        835                 840                 845

Lys Ser Arg Glu Asn Leu Thr Thr Ala Gly Pro Ser Asp Met Tyr
    850                 855                 860

<210> SEQ ID NO 79
<211> LENGTH: 863
<212> TYPE: PRT
<213> ORGANISM: Human rhinovirus

<400> SEQUENCE: 79

Met Gly Ala Gln Val Ser Arg Gln Asn Val Gly Thr His Ser Thr Gln
1               5                   10                  15

Asn Ser Val Ser Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160
```

```
Phe Gly Glu Asn Met Tyr Tyr His Phe Leu Gly Arg Ser Gly Tyr Thr
                165                 170                 175
Val His Val Gln Cys Asn Ala Ser Lys Phe His Gln Gly Thr Leu Leu
            180                 185                 190
Ile Ala Met Val Pro Glu His Gln Leu Ala Ser Ala Asn Tyr Gly Asn
        195                 200                 205
Val Thr Ala Gly Tyr Asn Tyr Thr His Pro Gly Glu Ala Gly Arg Asp
    210                 215                 220
Val Gly Gln Gln Arg Ala Asn Asn Glu Lys Gln Pro Ser Asp Asp Asn
225                 230                 235                 240
Trp Leu Asn Phe Asp Gly Thr Leu Leu Gly Asn Leu Leu Ile Phe Pro
                245                 250                 255
His Gln Phe Ile Asn Leu Arg Ser Asn Asn Ser Ala Thr Ile Ile Val
            260                 265                 270
Pro Tyr Val Asn Ala Val Pro Met Asp Ser Met Leu Arg His Asn Asn
        275                 280                 285
Trp Ser Leu Leu Ile Ile Pro Val Ser Pro Leu Asp Ala Asp Thr Ser
    290                 295                 300
Ala Thr Ala Ile Val Pro Ile Thr Val Ser Ile Ser Pro Met Phe Ser
305                 310                 315                 320
Glu Phe Ser Gly Ala Arg Ala Arg Pro Ala Ala Thr Gln Gly Leu
                325                 330                 335
Pro Val Tyr Met Thr Pro Gly Ser Gly Gln Phe Leu Thr Thr Asp Asp
            340                 345                 350
Leu Gln Ser Pro Ser Ala Leu Pro Trp Tyr His Pro Thr Lys Glu Ile
        355                 360                 365
Phe Ile Pro Gly Gln Val Arg Asn Leu Ile Glu Met Cys Gln Val Asp
    370                 375                 380
Thr Met Ile Pro Ile Asn Asn Thr Asn Glu Arg Ile Gly Asn Val Asn
385                 390                 395                 400
Met Tyr Thr Val Ser Leu Thr Ser Gln Thr Asn Thr Ala Glu Gln Ile
                405                 410                 415
Phe Ala Ile Lys Val Asp Ile Ala Ser Gln Pro Leu Ser Ser Thr Leu
            420                 425                 430
Ile Gly Glu Ile Ala Ser Tyr Tyr Thr His Trp Thr Gly Ser Leu Arg
        435                 440                 445
Phe Ser Phe Met Phe Cys Gly Thr Ala Asn Thr Thr Leu Lys Leu Leu
    450                 455                 460
Leu Ala Tyr Thr Pro Pro Gly Ile Asp Lys Pro Thr Thr Arg Lys Gln
465                 470                 475                 480
Ala Met Leu Gly Thr His Ile Val Trp Asp Ile Gly Leu Gln Ser Thr
                485                 490                 495
Val Ser Leu Val Val Pro Trp Val Ser Ala Ser His Phe Arg Tyr Thr
            500                 505                 510
Thr Pro Asp Thr Tyr Ser Met Ala Gly Tyr Ile Thr Cys Trp Tyr Gln
        515                 520                 525
Thr Asn Phe Val Phe Pro Pro Asn Thr Pro Asn Asn Ala Asn Met Ile
    530                 535                 540
Cys Phe Val Ser Gly Cys Lys Asp Phe Cys Leu Arg Met Ala Arg Asp
545                 550                 555                 560
Thr Asp Met His Val Gln Asn Val Pro Ile Thr Gln Asn Pro Val Glu
                565                 570                 575
```

```
Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
        595                 600                 605

Ala Gly Thr Gly His Thr Ser Ser Ile Gln Pro Glu Asp Thr Ile Glu
    610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp Ala Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
    770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
        835                 840                 845

Lys Ser Arg Glu Asn Leu Thr Thr Ala Gly Pro Ser Asp Met Tyr
    850                 855                 860

<210> SEQ ID NO 80
<211> LENGTH: 863
<212> TYPE: PRT
<213> ORGANISM: Human rhinovirus

<400> SEQUENCE: 80

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95
```

```
Val Ala Asn Ala Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
            115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
            195                 200                 205

Val Thr Ala Gly Tyr Asn Tyr Thr His Pro Gly Glu Ala Gly Arg Asp
            210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
            275                 280                 285

Trp Ser Leu Leu Ile Ile Pro Val Ser Pro Leu Asp Ala Asp Thr Ser
            290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
            355                 360                 365

Phe Ile Pro Gly Gln Val Arg Asn Leu Ile Glu Met Cys Gln Val Asp
    370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
            435                 440                 445

Phe Ser Phe Met Phe Cys Gly Thr Ala Asn Thr Thr Leu Lys Leu Leu
    450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
            500                 505                 510
```

Thr Pro Asp Thr Tyr Ser Met Ala Gly Tyr Ile Thr Cys Trp Tyr Gln
             515                 520                 525

Thr Asn Phe Val Phe Pro Pro Asn Thr Pro Asn Asn Ala Asn Met Ile
        530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
        595                 600                 605

Ala Gly Thr Gly His Thr Ser Ser Ile Gln Pro Glu Asp Thr Ile Glu
610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp Ala Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Ser Arg Tyr Gly Val Ser Val Thr
770                 775                 780

Asn Asp Met Gly Thr Leu Cys Thr Arg Ile Val Thr Asn Gln Gln Ala
785                 790                 795                 800

His Leu Val Gln Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
        835                 840                 845

Lys Ser Arg Glu Asn Leu Thr Thr Ala Gly Pro Ser Asp Met Tyr
850                 855                 860

<210> SEQ ID NO 81
<211> LENGTH: 863
<212> TYPE: PRT
<213> ORGANISM: Human rhinovirus

<400> SEQUENCE: 81

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

-continued

Phe Lys Asp Ala Ala Ser Ser Gly Ala Ser Lys Leu Glu Phe Ser Gln
          35                  40                  45

Asp Pro Ser Lys Phe Thr Asp Pro Val Lys Asp Val Leu Glu Lys Gly
 50                  55                  60

Ile Pro Thr Leu Gln Ser Pro Thr Val Glu Ala Cys Gly Tyr Ser Asp
 65                  70                  75                  80

Arg Ile Ile Gln Ile Thr Arg Gly Asp Ser Thr Ile Thr Ser Gln Asp
                 85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
            115                 120                 125

Ser Asn Arg Phe Tyr Thr Leu Glu Ser Lys Val Trp Lys Arg Asp Ser
        130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
        210                 215                 220

Val Gly Gln Gln Arg Ala Leu Ile Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
    370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

```
Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
                500                 505                 510

Thr Pro Asp Thr Tyr Ser Met Ala Gly Tyr Ile Thr Cys Trp Tyr Gln
                515                 520                 525

Thr Asn Phe Val Phe Pro Pro Asn Thr Pro Asn Asn Ala Asn Met Ile
530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Pro Asn Ile
                580                 585                 590

Arg Glu Ser His Pro Thr Thr Ser Asn Ala Ala Thr Ala Leu Asp Ala
                595                 600                 605

Ala Gly Thr Gly His Thr Ser Ser Ile Gln Pro Glu Asp Thr Ile Glu
610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
                660                 665                 670

Leu Gln Glu Met Ala Gln Val Arg Arg Lys Phe Glu Met Phe Thr Tyr
                675                 680                 685

Val Arg Phe Asp Ser Glu Ile Thr Leu Val Pro Cys Ile Ala Gly Arg
                690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
                740                 745                 750

Ser Leu Pro Phe Leu Ser Ile Ala Ser Ala Tyr Tyr Met Phe Tyr Asp
                755                 760                 765

Gly Tyr Asp Gly Asp Lys Ser Ser Ser Arg Tyr Gly Val Ser Val Thr
770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
                820                 825                 830

Asn Val Thr Asn Tyr Lys Val Arg Asp Gly Glu Pro Thr Leu Phe Ile
                835                 840                 845

Lys Ser Arg Glu Asn Leu Thr Thr Ala Gly Pro Ser Asp Met Tyr
850                 855                 860
```

-continued

```
<210> SEQ ID NO 82
<211> LENGTH: 863
<212> TYPE: PRT
<213> ORGANISM: Human rhinovirus

<400> SEQUENCE: 82
```

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
            115                 120                 125

Ser Asn Arg Phe Tyr Thr Leu Glu Ser Lys Val Trp Lys Arg Asp Ser
        130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
            195                 200                 205

Val Thr Ala Gly Tyr Asn Tyr Thr His Pro Gly Glu Ala Gly Arg Asp
        210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
            275                 280                 285

Trp Ser Leu Leu Ile Ile Pro Val Ser Pro Leu Asp Ala Asp Thr Ser
        290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
    370                 375                 380

```
Thr Met Ile Pro Ile Asn Asn Thr Ala Glu Arg Ile Gly Asn Val Asn
385                 390                 395                 400

Met Tyr Thr Val Ser Leu Thr Ser Gln Thr Asn Thr Ala Glu Gln Ile
            405                 410                 415

Phe Ala Ile Lys Val Asp Ile Ala Ser Gln Pro Leu Ser Ser Thr Leu
        420                 425                 430

Ile Gly Glu Ile Ala Ser Tyr Tyr Thr His Trp Thr Gly Ser Leu Arg
    435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
                500                 505                 510

Thr Pro Asp Thr Tyr Ser Met Ala Gly Tyr Ile Thr Cys Trp Tyr Gln
            515                 520                 525

Thr Asn Phe Val Phe Pro Pro Asn Thr Pro Asn Asn Ala Asn Met Ile
530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
                595                 600                 605

Ala Gly Thr Gly His Thr Ser Ser Ile Gln Pro Glu Asp Thr Ile Glu
            610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
                755                 760                 765

Gly Tyr Asp Gly Asp Lys Ser Ser Arg Tyr Gly Val Ser Val Thr
            770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
```

805                 810                 815
Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
            835                 840                 845

Lys Ser Arg Gln Asn Leu Thr Thr Ala Gly Pro Ser Asp Met Tyr
            850                 855                 860

<210> SEQ ID NO 83
<211> LENGTH: 863
<212> TYPE: PRT
<213> ORGANISM: Human rhinovirus

<400> SEQUENCE: 83

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
            115                 120                 125

Ser Asn Arg Phe Tyr Thr Leu Glu Ser Lys Val Trp Lys Arg Asp Ser
        130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
            195                 200                 205

Val Thr Ala Gly Tyr Asn Tyr Thr His Pro Gly Glu Ala Gly Arg Asp
        210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
            275                 280                 285

Trp Ser Leu Leu Ile Ile Pro Val Ser Pro Leu Asp Ala Asp Thr Ser
        290                 295                 300

Ala Thr Ala Ile Val Pro Ile Thr Val Ser Ile Ser Pro Met Phe Ser
305                 310                 315                 320

-continued

```
Glu Phe Ser Gly Ala Arg Ala Arg Pro Ala Ala Thr Gln Gly Leu
            325                 330                 335

Pro Val Tyr Met Thr Pro Gly Ser Gly Gln Phe Leu Thr Asp Asp
            340                 345                 350

Leu Gln Ser Pro Ser Ala Leu Pro Trp Tyr His Pro Thr Lys Glu Ile
            355                 360                 365

Phe Ile Pro Gly Gln Val Arg Asn Leu Ile Glu Met Cys Gln Val Asp
        370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
            435                 440                 445

Phe Ser Phe Met Phe Cys Gly Thr Ala Asn Thr Thr Leu Lys Leu Leu
        450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
            515                 520                 525

Thr Asn Phe Val Phe Pro Pro Asn Thr Pro Asn Asn Ala Asn Met Ile
        530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
            595                 600                 605

Ala Gly Thr Gly His Thr Ser Ser Ile Gln Pro Glu Asp Thr Ile Glu
        610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
            675                 680                 685

Val Arg Phe Asp Ser Glu Ile Thr Leu Val Pro Cys Ile Ala Gly Arg
        690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
```

-continued

```
                740                 745                 750
Ser Leu Pro Phe Leu Ser Ile Ala Ser Ala Tyr Tyr Met Phe Tyr Asp
            755                 760                 765

Gly Tyr Asp Gly Asp Lys Ser Ser Arg Tyr Gly Val Ser Val Thr
        770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Ala Val Arg Asp Gly Glu Pro Thr Leu Phe Ile
        835                 840                 845

Lys Ser Arg Glu Asn Leu Thr Thr Ala Gly Pro Ser Asp Met Tyr
    850                 855                 860

<210> SEQ ID NO 84
<211> LENGTH: 863
<212> TYPE: PRT
<213> ORGANISM: Human rhinovirus

<400> SEQUENCE: 84

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Ile Thr Asn Asn Gln Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255
```

-continued

```
His Gln Phe Ile Asn Leu Arg Ser Asn Ser Ala Thr Ile Ile Val
                260                 265                 270

Pro Tyr Val Asn Ala Val Pro Met Asp Ser Met Leu Arg His Asn Asn
            275                 280                 285

Trp Ser Leu Leu Ile Ile Pro Val Ser Pro Leu Asp Ala Asp Thr Ser
    290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
370                 375                 380

Thr Met Ile Pro Ile Asn Asn Thr Asn Glu Ala Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
        515                 520                 525

Thr Asn Phe Val Phe Pro Pro Asn Thr Pro Asn Asn Ala Asn Met Ile
530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
        595                 600                 605

Ala Gly Thr Gly His Thr Ser Ser Ile Gln Pro Glu Asp Thr Ile Glu
610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
```

```
                675                 680                 685
Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
    770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
        835                 840                 845

Lys Ser Arg Glu Asn Leu Thr Thr Ala Gly Pro Ser Asp Met Tyr
    850                 855                 860

<210> SEQ ID NO 85
<211> LENGTH: 863
<212> TYPE: PRT
<213> ORGANISM: Human rhinovirus

<400> SEQUENCE: 85

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190
```

```
Ile Ala Met Val Pro Glu His Gln Leu Ala Ser Ala Asn Tyr Gly Asn
            195                 200                 205

Val Thr Ala Gly Tyr Asn Tyr Thr His Pro Gly Glu Ala Gly Arg Asp
        210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
        290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
                340                 345                 350

Leu Gln Ser Pro Ser Ala Leu Pro Trp Tyr His Pro Thr Lys Glu Ile
            355                 360                 365

Phe Ile Pro Gly Gln Val Arg Asn Leu Ile Glu Met Cys Gln Val Asp
            370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
                420                 425                 430

Ile Gly Glu Ile Ala Ser Tyr Tyr Thr His Trp Thr Gly Ser Leu Arg
            435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
        500                 505                 510

Thr Pro Asp Thr Tyr Ser Met Ala Gly Tyr Ile Thr Cys Trp Tyr Gln
        515                 520                 525

Thr Asn Phe Val Phe Pro Pro Asn Thr Pro Asn Asn Ala Asn Met Ile
        530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Pro Asn Ile
            580                 585                 590

Arg Glu Ser His Pro Thr Thr Ser Asn Ala Ala Thr Ala Leu Asp Ala
            595                 600                 605

Ala Gly Thr Gly His Thr Ser Ser Ile Gln Pro Glu Asp Thr Ile Glu
```

```
                610               615                620
Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
                660                 665                 670

Leu Gln Glu Met Ala Gln Val Arg Arg Lys Phe Glu Met Phe Thr Tyr
                675                 680                 685

Val Arg Phe Asp Ser Glu Ile Thr Leu Val Pro Cys Ile Ala Gly Arg
690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
                740                 745                 750

Ser Leu Pro Phe Leu Ser Ile Ala Ser Ala Tyr Tyr Met Phe Tyr Asp
                755                 760                 765

Gly Tyr Asp Gly Asp Lys Ser Ser Arg Tyr Gly Val Ser Val Thr
770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
                820                 825                 830

Asn Val Thr Asn Tyr Lys Val Ile Asp Gly Glu Pro Thr Leu Phe Ile
                835                 840                 845

Lys Ser Arg Ile Asn Leu Thr Thr Ala Gly Pro Ser Asp Met Tyr
850                 855                 860

<210> SEQ ID NO 86
<211> LENGTH: 863
<212> TYPE: PRT
<213> ORGANISM: Human rhinovirus

<400> SEQUENCE: 86

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
                20                  25                  30

Phe Lys Asp Ala Ala Ser Ser Gly Ala Ser Lys Leu Glu Phe Ser Gln
                35                  40                  45

Asp Pro Ser Lys Phe Thr Asp Pro Val Lys Asp Val Leu Glu Lys Gly
50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
                100                 105                 110

Ala Asp Asp Ala Ser Ala Ile Asp Lys Pro Thr Gln Pro Asp Thr Ser
                115                 120                 125
```

```
Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Ala Leu Ile Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
    370                 375                 380

Thr Met Ile Pro Ile Asn Asn Thr Ala Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
    450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
        515                 520                 525

Thr Asn Phe Val Phe Pro Pro Asn Thr Pro Asn Asn Ala Asn Met Ile
    530                 535                 540

Cys Phe Val Ser Gly Cys Lys Asp Phe Cys Leu Arg Met Ala Arg Asp
```

```
                545                 550                 555                 560
Thr Asp Met His Val Gln Asn Val Pro Ile Thr Gln Asn Pro Val Glu
                    565                 570                 575
Asn Tyr Ile Asp Glu Val Leu Asn Glu Val Leu Val Pro Asn Ile
                580                 585                 590
Arg Glu Ser His Pro Thr Thr Ser Asn Ala Ala Thr Ala Leu Asp Ala
                    595                 600                 605
Ala Gly Thr Gly His Thr Ser Ser Ile Gln Pro Glu Asp Thr Ile Glu
                610                 615                 620
Thr Arg Tyr Val Gln Thr Ser His Thr Arg Asp Glu Met Ser Val Glu
625                 630                 635                 640
Ser Phe Leu Gly Arg Ser Gly Cys Ile His Ile Ser Thr Ile Thr Met
                    645                 650                 655
Lys Lys Glu Asn Tyr Asn Asp His Asn Phe Val Asp Trp Lys Ile Thr
                660                 665                 670
Leu Gln Glu Met Ala Gln Val Arg Arg Lys Phe Glu Met Phe Thr Tyr
                    675                 680                 685
Val Arg Phe Asp Ser Glu Ile Thr Leu Val Pro Cys Ile Ala Gly Arg
                690                 695                 700
Gly Glu Asp Ile Gly His Ile Val Met Gln Tyr Met Tyr Val Pro Pro
705                 710                 715                 720
Gly Ala Pro Val Pro Lys Lys Arg Asp Asp Tyr Thr Trp Gln Ser Gly
                    725                 730                 735
Thr Asn Ala Ser Val Phe Trp Gln His Gly Gln Pro Tyr Pro Arg Phe
                740                 745                 750
Ser Leu Pro Phe Leu Ser Ile Ala Ser Ala Tyr Tyr Met Phe Tyr Asp
                    755                 760                 765
Gly Tyr Asp Gly Asp Lys Ser Ser Arg Tyr Gly Val Ser Val Thr
                    770                 775                 780
Asn Asp Met Gly Thr Leu Cys Thr Arg Ile Val Thr Asn Gln Gln Glu
785                 790                 795                 800
His Leu Val Glu Val Thr Thr Arg Val Tyr His Lys Ala Lys His Val
                    805                 810                 815
Lys Ala Trp Cys Pro Arg Ala Pro Arg Ala Val Pro Tyr Thr His Ser
                820                 825                 830
Asn Val Thr Asn Tyr Lys Val Arg Asp Gly Glu Ala Thr Leu Phe Ile
                    835                 840                 845
Lys Ser Arg Gln Asn Leu Thr Thr Ala Gly Pro Ser Asp Met Tyr
850                 855                 860

<210> SEQ ID NO 87
<211> LENGTH: 863
<212> TYPE: PRT
<213> ORGANISM: Human rhinovirus

<400> SEQUENCE: 87

Met Gly Ala Gln Val Ser Arg Gln Asn Val Gly Thr His Ser Thr Gln
1               5                   10                  15
Asn Ser Val Ser Gly Gly Ser Ser Leu Asn Tyr Phe Asn Ile Asn Tyr
                20                  25                  30
Phe Lys Asp Ala Ala Ser Ser Gly Ala Ser Lys Leu Glu Phe Ser Gln
                    35                  40                  45
Asp Pro Ser Lys Phe Thr Asp Pro Val Lys Asp Val Leu Glu Lys Gly
                50                  55                  60
```

```
Ile Pro Thr Leu Gln Ser Pro Thr Val Glu Ala Cys Gly Tyr Ser Asp
 65                  70                  75                  80

Arg Ile Ile Gln Ile Thr Arg Gly Asp Ser Thr Ile Thr Ser Gln Asp
                 85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
210                 215                 220

Val Gly Gln Gln Ile Ala Asn Asn Gln Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
370                 375                 380

Thr Met Ile Pro Ile Asn Asn Thr Asn Glu Ala Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
```

-continued

```
                485                 490                 495
Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
        515                 520                 525

Thr Asn Phe Val Phe Pro Pro Asn Thr Pro Asn Asn Ala Asn Met Ile
    530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
            580                 585                 590

Arg Glu Ser His Pro Thr Thr Ser Asn Ala Ala Thr Ala Leu Asp Ala
        595                 600                 605

Ala Gly Thr Gly His Thr Ser Ser Ile Gln Pro Glu Asp Thr Ile Glu
    610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
    770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Ile Asp Gly Glu Pro Thr Leu Phe Ile
        835                 840                 845

Lys Leu Arg Ile Asn Leu Thr Thr Ala Gly Pro Ser Asp Met Tyr
    850                 855                 860
```

<210> SEQ ID NO 88
<211> LENGTH: 863
<212> TYPE: PRT
<213> ORGANISM: Human rhinovirus

<400> SEQUENCE: 88

```
Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
                20                  25                  30

Phe Lys Asp Ala Ala Ser Ser Gly Ala Ser Lys Leu Glu Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
    290                 295                 300

Ala Thr Leu Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
    370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
```

```
                420             425             430
Ile Gly Glu Ile Ala Ser Tyr Tyr Thr His Trp Thr Gly Ser Leu Arg
            435             440             445
Phe Ser Phe Met Phe Cys Gly Thr Ala Asn Thr Thr Leu Lys Leu Leu
450             455             460
Leu Ala Tyr Thr Pro Gly Ile Asp Lys Pro Thr Arg Lys Gln
465             470             475             480
Ala Met Leu Gly Thr His Ile Val Trp Asp Ile Gly Leu Gln Ser Thr
            485             490             495
Val Ser Leu Val Val Pro Trp Val Ser Ala Ser His Phe Arg Tyr Thr
            500             505             510
Thr Pro Asp Thr Tyr Ser Met Ala Gly Tyr Ile Thr Cys Trp Tyr Gln
            515             520             525
Thr Asn Phe Val Phe Pro Pro Asn Thr Pro Asn Asn Ala Asn Met Ile
            530             535             540
Cys Phe Val Ser Gly Cys Lys Asp Phe Cys Leu Arg Met Ala Arg Asp
545             550             555             560
Thr Asp Met His Val Gln Asn Val Pro Ile Thr Gln Asn Pro Val Glu
            565             570             575
Asn Tyr Ile Asp Glu Val Leu Asn Glu Val Leu Val Pro Asn Ile
            580             585             590
Arg Glu Ser His Pro Thr Thr Ser Asn Ala Ala Thr Ala Leu Asp Ala
            595             600             605
Ala Gly Thr Gly His Thr Ser Ser Ile Gln Pro Glu Asp Thr Ile Glu
            610             615             620
Thr Arg Tyr Val Gln Thr Ser His Thr Arg Asp Glu Met Ser Val Glu
625             630             635             640
Ser Phe Leu Gly Arg Ser Gly Cys Ile His Ile Ser Thr Ile Thr Met
            645             650             655
Lys Lys Glu Asn Tyr Asn Asp His Asn Phe Val Asp Trp Lys Ile Thr
            660             665             670
Leu Gln Glu Met Ala Gln Val Arg Arg Lys Phe Glu Met Phe Thr Tyr
            675             680             685
Val Arg Phe Asp Ser Glu Ile Thr Leu Val Pro Cys Ile Ala Gly Arg
            690             695             700
Gly Glu Asp Ile Gly His Ile Val Met Gln Tyr Met Tyr Val Pro Pro
705             710             715             720
Gly Ala Pro Val Pro Lys Lys Arg Asp Asp Tyr Thr Trp Gln Ser Gly
            725             730             735
Thr Asn Ala Ser Val Phe Trp Gln His Gly Gln Pro Tyr Pro Arg Phe
            740             745             750
Ser Leu Pro Phe Leu Ser Ile Ala Ser Ala Tyr Tyr Met Phe Tyr Asp
            755             760             765
Gly Tyr Asp Gly Asp Lys Ser Ser Ser Arg Tyr Gly Val Ser Val Thr
            770             775             780
Asn Asp Met Gly Thr Leu Cys Thr Arg Ile Val Thr Asn Gln Gln Glu
785             790             795             800
His Leu Val Glu Val Thr Thr Arg Val Tyr His Lys Ala Lys His Val
            805             810             815
Lys Ala Trp Cys Pro Arg Ala Pro Arg Ala Val Pro Tyr Thr His Ser
            820             825             830
Asn Val Thr Asn Tyr Lys Val Arg Asp Gly Glu Pro Thr Leu Phe Ile
            835             840             845
```

Lys Ser Arg Glu Asn Leu Thr Thr Ala Gly Pro Ser Asp Met Tyr
850                 855                 860

<210> SEQ ID NO 89
<211> LENGTH: 863
<212> TYPE: PRT
<213> ORGANISM: Human rhinovirus

<400> SEQUENCE: 89

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
                20                  25                  30

Phe Lys Asp Ala Ala Ser Ser Gly Ala Ser Lys Leu Glu Phe Ser Gln
            35                  40                  45

Asp Pro Ser Lys Phe Thr Asp Pro Val Lys Asp Val Leu Glu Lys Gly
        50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Ala Gly Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
    290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile

```
              355                 360                 365
Phe Ile Pro Gly Gln Val Arg Asn Leu Ile Glu Met Cys Gln Val Asp
        370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Ala Glu Gln Ile
                    405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
        450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                    485                 490                 495

Val Ser Leu Val Val Pro Trp Val Ser Ala Ser His Phe Arg Tyr Thr
                500                 505                 510

Thr Pro Asp Thr Tyr Ser Met Ala Gly Tyr Ile Thr Cys Trp Tyr Gln
            515                 520                 525

Thr Asn Phe Val Phe Pro Pro Asn Thr Pro Asn Asn Ala Asn Met Ile
        530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
                580                 585                 590

Arg Glu Ser His Pro Thr Thr Ser Asn Ala Ala Thr Ala Leu Asp Ala
            595                 600                 605

Ala Gly Thr Gly His Thr Ser Ser Ile Gln Pro Glu Asp Thr Ile Glu
        610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                    645                 650                 655

Lys Lys Glu Asn Tyr Asn Asp His Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
        690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                    725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
        770                 775                 780
```

```
Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
            805                 810                 815

Lys Ala Trp Cys Pro Arg Ala Pro Arg Ala Val Pro Tyr Thr His Ser
        820                 825                 830

Asn Val Thr Asn Tyr Lys Val Arg Asp Gly Glu Pro Thr Leu Phe Ile
            835                 840                 845

Lys Ser Arg Glu Asn Leu Thr Thr Ala Gly Pro Ser Asp Met Tyr
        850                 855                 860

<210> SEQ ID NO 90
<211> LENGTH: 863
<212> TYPE: PRT
<213> ORGANISM: Human rhinovirus

<400> SEQUENCE: 90

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Ala Gly Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Ala Asn Asn Glu Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Asp Ala Asp Thr Ser
```

-continued

```
            290                 295                 300
Gly Thr Leu Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                325                 330                 335

Pro Val Tyr Met Thr Pro Gly Ser Gly Gln Phe Leu Thr Thr Asp Asp
                340                 345                 350

Leu Gln Ser Pro Ser Ala Leu Pro Trp Tyr His Pro Thr Lys Glu Ile
                355                 360                 365

Phe Ile Pro Gly Gln Val Arg Asn Leu Ile Glu Met Cys Gln Val Asp
370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
                420                 425                 430

Ile Gly Glu Ile Ala Ser Tyr Tyr Thr His Trp Thr Gly Ser Leu Arg
                435                 440                 445

Phe Ser Phe Met Phe Cys Gly Thr Ala Asn Thr Thr Leu Lys Leu Leu
                450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                485                 490                 495

Val Ser Leu Val Val Pro Trp Val Ser Ala Ser His Phe Arg Tyr Thr
                500                 505                 510

Thr Pro Asp Thr Tyr Ser Met Ala Gly Tyr Ile Thr Cys Trp Tyr Gln
                515                 520                 525

Thr Asn Phe Val Phe Pro Pro Asn Thr Pro Asn Asn Ala Asn Met Ile
                530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Val Pro Asn Ile
                580                 585                 590

Arg Glu Ser His Pro Thr Thr Ser Asn Ala Ala Thr Ala Leu Asp Ala
                595                 600                 605

Ala Gly Thr Gly His Thr Ser Ser Ile Gln Pro Glu Asp Thr Ile Glu
610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Asp His Asn Phe Val Asp Trp Lys Ile Thr
                660                 665                 670

Leu Gln Glu Met Ala Gln Val Arg Arg Lys Phe Glu Met Phe Thr Tyr
                675                 680                 685

Val Arg Phe Asp Ser Glu Ile Thr Leu Val Pro Cys Ile Ala Gly Arg
                690                 695                 700

Gly Glu Asp Ile Gly His Ile Val Met Gln Tyr Met Tyr Val Pro Pro
705                 710                 715                 720
```

-continued

Gly Ala Pro Val Pro Lys Lys Arg Asp Asp Tyr Thr Trp Gln Ser Gly
            725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
            755                 760                 765

Gly Tyr Asp Gly Asp Lys Ser Ser Ser Arg Tyr Gly Val Ser Val Thr
        770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
            835                 840                 845

Lys Ser Arg Glu Asn Leu Thr Thr Ala Gly Pro Ser Asp Met Tyr
    850                 855                 860

<210> SEQ ID NO 91
<211> LENGTH: 863
<212> TYPE: PRT
<213> ORGANISM: Human rhinovirus

<400> SEQUENCE: 91

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Arg Asp Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Ala Leu Ile Glu Lys Gln Pro Ser Asp Asp Asn

```
                225                 230                 235                 240
        Trp Leu Asn Phe Asp Gly Thr Leu Leu Gly Asn Leu Leu Ile Phe Pro
                            245                 250                 255

His Gln Phe Ile Asn Leu Arg Ser Asn Asn Ser Ala Thr Ile Ile Val
                            260                 265                 270

Pro Tyr Val Asn Ala Val Pro Met Asp Ser Met Leu Arg His Asn Asn
                            275                 280                 285

Trp Ser Leu Leu Ile Ile Pro Val Ser Pro Leu Asp Ala Asp Thr Ser
                290                 295                 300

Ala Thr Leu Ile Val Pro Ile Thr Val Ser Ile Ser Pro Met Phe Ser
        305                 310                 315                 320

Glu Phe Ser Gly Ala Arg Ala Arg Pro Ala Ala Thr Gln Gly Leu
                            325                 330                 335

Pro Val Tyr Met Thr Pro Gly Ser Gly Gln Phe Leu Thr Asp Asp
                            340                 345                 350

Leu Gln Ser Pro Ser Ala Leu Pro Trp Tyr His Pro Thr Lys Glu Ile
                            355                 360                 365

Phe Ile Pro Gly Gln Val Arg Asn Leu Ile Glu Met Cys Gln Val Asp
                370                 375                 380

Thr Met Ile Pro Ile Asn Asn Thr Ala Glu Arg Ile Gly Asn Val Asn
        385                 390                 395                 400

Met Tyr Thr Val Ser Leu Thr Ser Gln Thr Asn Thr Ala Glu Gln Ile
                            405                 410                 415

Phe Ala Ile Lys Val Asp Ile Ala Ser Gln Pro Leu Ser Ser Thr Leu
                            420                 425                 430

Ile Gly Glu Ile Ala Ser Tyr Tyr Thr His Trp Thr Gly Ser Leu Arg
                            435                 440                 445

Phe Ser Phe Met Phe Cys Gly Thr Ala Asn Thr Thr Leu Lys Leu Leu
                            450                 455                 460

Leu Ala Tyr Thr Pro Pro Gly Ile Asp Lys Pro Thr Thr Arg Lys Gln
        465                 470                 475                 480

Ala Met Leu Gly Thr His Ile Val Trp Asp Ile Gly Leu Gln Ser Thr
                            485                 490                 495

Val Ser Leu Val Val Pro Trp Val Ser Ala Ser His Phe Arg Tyr Thr
                            500                 505                 510

Thr Pro Asp Thr Tyr Ser Met Ala Gly Tyr Ile Thr Cys Trp Tyr Gln
                            515                 520                 525

Thr Asn Phe Val Phe Pro Pro Asn Thr Pro Asn Asn Ala Asn Met Ile
                            530                 535                 540

Cys Phe Val Ser Gly Cys Lys Asp Phe Cys Leu Arg Met Ala Arg Asp
        545                 550                 555                 560

Thr Asp Met His Val Gln Asn Val Pro Ile Thr Gln Asn Pro Val Glu
                            565                 570                 575

Asn Tyr Ile Asp Glu Val Leu Asn Glu Val Leu Val Pro Asn Ile
                            580                 585                 590

Arg Glu Ser His Pro Thr Thr Ser Asn Ala Ala Thr Ala Leu Asp Ala
                            595                 600                 605

Ala Gly Thr Gly His Thr Ser Ser Ile Gln Pro Glu Asp Thr Ile Glu
                            610                 615                 620

Thr Arg Tyr Val Gln Thr Ser His Thr Arg Asp Glu Met Ser Val Glu
        625                 630                 635                 640

Ser Phe Leu Gly Arg Ser Gly Cys Ile His Ile Ser Thr Ile Thr Met
                            645                 650                 655
```

-continued

```
Leu Ile Glu Asn Tyr Asn Asp Ala Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
    770                 775                 780

Asn Asp Met Gly Thr Leu Cys Thr Arg Ile Val Thr Asn Gln Gln Glu
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Ala Thr Leu Phe Ile
        835                 840                 845

Lys Ser Arg Gln Asn Leu Thr Thr Ala Gly Pro Ser Asp Met Tyr
    850                 855                 860

<210> SEQ ID NO 92
<211> LENGTH: 863
<212> TYPE: PRT
<213> ORGANISM: Human rhinovirus

<400> SEQUENCE: 92

Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Ala Asp Asp Ala Ser Ala Ile Asp Lys Pro Thr Gln Pro Asp Thr Ser
        115                 120                 125

Ser Asn Arg Phe Tyr Thr Leu Glu Ser Lys Val Trp Lys Ala Gly Ser
    130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
```

```
            165                 170                 175
Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
            195                 200                 205

Val Thr Ala Gly Tyr Asn Tyr Thr His Pro Gly Glu Ala Gly Arg Asp
            210                 215                 220

Val Gly Gln Gln Ile Ala Asn Asn Gln Lys Gln Pro Ser Asp Asp Asn
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Ile Ile Val
                260                 265                 270

Pro Tyr Val Asn Ala Val Pro Met Asp Ser Met Leu Arg His Asn Asn
                275                 280                 285

Trp Ser Leu Leu Ile Ile Pro Val Ser Pro Leu Asp Ala Asp Thr Ser
                290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Thr Gln Gly Leu
                    325                 330                 335

Pro Val Tyr Met Thr Pro Gly Ser Gly Gln Phe Leu Thr Thr Asp Asp
                340                 345                 350

Leu Gln Ser Pro Ser Ala Leu Pro Trp Tyr His Pro Thr Lys Glu Ile
                355                 360                 365

Phe Ile Pro Gly Gln Val Arg Asn Leu Ile Glu Met Cys Gln Val Asp
                370                 375                 380

Thr Met Ile Pro Ile Asn Asn Thr Asn Glu Ala Ile Gly Asn Val Asn
385                 390                 395                 400

Met Tyr Thr Val Ser Leu Thr Ser Gln Thr Asn Thr Ala Glu Gln Ile
                    405                 410                 415

Phe Ala Ile Lys Val Asp Ile Ala Ser Gln Pro Leu Ser Ser Thr Leu
                420                 425                 430

Ile Gly Glu Ile Ala Ser Tyr Tyr Thr His Trp Thr Gly Ser Leu Arg
                435                 440                 445

Phe Ser Phe Met Phe Cys Gly Thr Ala Asn Thr Thr Leu Lys Leu Leu
                450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Ile Gly Leu Gln Ser Thr
                    485                 490                 495

Val Ser Leu Val Val Pro Trp Val Ser Ala Ser His Phe Arg Tyr Thr
                500                 505                 510

Thr Pro Asp Thr Tyr Ser Met Ala Gly Tyr Ile Thr Cys Trp Tyr Gln
                515                 520                 525

Thr Asn Phe Val Phe Pro Pro Asn Thr Pro Asn Asn Ala Asn Met Ile
                530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                    565                 570                 575

Asn Tyr Ile Asp Glu Val Leu Asn Glu Val Leu Val Val Pro Asn Ile
                580                 585                 590
```

-continued

```
Arg Glu Ser His Pro Thr Thr Ser Asn Ala Ala Thr Ala Leu Asp Ala
        595                 600                 605

Ala Gly Thr Gly His Thr Ser Ser Ile Gln Pro Glu Asp Thr Ile Glu
    610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Leu Ile Glu Asn Tyr Asn Asp Ala Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Ser Arg Tyr Gly Val Ser Val Thr
    770                 775                 780

Asn Asp Met Gly Thr Leu Cys Thr Arg Ile Val Thr Asn Gln Gln Ala
785                 790                 795                 800

His Leu Val Gln Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Ile Asp Gly Glu Pro Thr Leu Phe Ile
        835                 840                 845

Lys Leu Arg Ile Asn Leu Thr Thr Ala Gly Pro Ser Asp Met Tyr
    850                 855                 860
```

IMMUNOGENIC HUMAN RHINOVIRUS (HRV) COMPOSITIONS

SEQUENCE LISTING

The instant application contains a Sequence Listing which has been submitted electronically in ASCII format and hereby is incorporated by reference in entirety. Said ASCII copy, created on 14 Mar. 2014, is named BMISL.txt and is 236,175 bytes in size.

BACKGROUND

The current stable of licensed vaccines in the human and veterinary arenas is generally successful against what are termed "Class One pathogens." Class One pathogens (such as poliovirus, smallpox, measles, mumps and rubella viruses) are those pathogens, which, in general: (1) infect or cause the most serious disease in children/young adults, (2) carry a relatively stable microbial genome, (3) have a natural history of disease which results in spontaneous recovery; and (4) induce durable memory, associated with polyclonal and multi-epitope antigen recognition.

In contrast, Class Two pathogens, such as, human rhinovirus (HRV), Foot-and-Mouth-Disease Virus (FMDV), viral influenza, HIV-1, malaria, tuberculosis, trypanosomes, schistosomes, leishmania, anaplasma, enterovirus, astrovirus, Norwalk viruses, toxigenic/pathogenic E. coli, Neisseria, Streptomyces, nontypeable haemophilus influenza, hepatitis C, cancer cells etc. are characterized by quite opposite features. For example, Class Two pathogens: (1) tend to infect and are transmitted in a significantly extended host age range, with infections occurring and reoccurring from childhood through the geriatric period; (2) exhibit microbial genetic instability in defined regions of their genome (a hallmark of the successful evolution of such pathogens); (3) in some cases, include spontaneous recovery of disease that frequently still leaves the host vulnerable to multiple repeated annual infections and/or the establishment of either a chronic/active or chronic/latent infectious state; (4) induce oligoclonal, early immune responses that are directed to a very limited set of immunodominant epitopes which provide either narrow strain-specific protection, no protection and/or enhanced infection; and (5) cause immune dysregulation following infection or vaccination, e.g. epitope blocking antibody, atypical primary immune response Ig subclasses, anamnestic cross reactive recall and inappropriate TH1 and/or TH2 cytokine metabolism.

At the immunologic level, infection with HRV may stimulate strain-specific immunity, but the host remains susceptible to re-infection by other serotypes of the virus. Characterization of immune responses against HRV suggests that the immune system recognizes and reacts to only a small number of immunodominant epitopes. Because the immunodominant epitopes are in highly variable sites that distinguish the various HRV serotypes, the immune response is highly strain-specific. Thus, an effective cross-protective vaccine against HRV must stimulate immune responses that are directed against more highly conserved regions of the virus, some of which may have previously been subdominant. In the case of HRV, a successful vaccine must overcome strain-specific immune responses to stimulate cross-protective immunity against 1) multiple serotypes and 2) evolving antigenic determinants.

Although some advances with regard to antigen delivery and expression have improved the immunogenicity of some Class Two microbial pathogens, current vaccine technologies have not readily translated into new, broadly effective and safe licensed vaccines for use in humans or animals. That may be due, in large part, to a poor understanding of the fundamental laws governing the vertebrate host defense system origin, repertoire development, maintenance, activation, senescence and co-evolution in similar and dissimilar environments.

Antigenic variation is an evolved mechanism to ensure rapid sequence variation of specific pathogen gene(s) encoding homologues of an individual protein antigen, usually involving multiple, related gene copies, resulting in a change in the structure of an antigen on the surface of the pathogen. Thus, the host immune system during infection or re-infection is less capable of recognizing the pathogen and must make new antibodies to recognize the changed antigens before the host can continue to combat the disease. As a result, the host cannot stay completely immune to the viral disease. That phenomenon stands as one of the more, if not, most formidable problem challenging modern vaccine development today.

Thus, it is not surprising that natural infection and vaccination fail to yield a more functional cross-reactive primary and anamnestic immunity as the repertoire development against those less immunogenic epitopes, which may be more conserved and capable of generating cross-strain immunity, are lower on the antigenic hierarchy.

The immunologic phenomenon whereby immunodominant epitopes misdirect the immune response away from more conserved and less immunogenic regions on an antigen was initially termed "clonal dominance"60 (Kohler et al., J Acquir Immune Defic Syndr 1992; 6:1158-68), which later was renamed as "Deceptive Imprinting" (Köhler et al., Immunol Today 1994 (10):475-8).

The immunologic mechanisms for immunodominance behind deceptive imprinting are not fully understood, and no one mechanism yet fully explains how or why certain epitopes have evolved to be immunoregulatory and immunodominant. The range of immune responses observed in the phenomena include: the induction of highly strain/isolate-specific neutralizing antibody capable of inducing passive protection in experimental animal model-viral challenge systems all the way to the induction of a binding non-protective/non-neutralizing, blocking and even pathogen-enhancing antibody that in some cases prevents the host immune system from recognizing the nearly adjacent epitopes, to interfering with CD4 T-cell help. The same decoying of the immune response through immunodominance resulting in a more narrowly focused set of epitopes is observed with T cells of the host in the development of helper and cytotoxic cell-mediated immunity. (Gzyl et al., Virology 2004; 318(2):493-506; Kiszka et al., J Virol. 2002 76(9):4222-32; and Goulder et al., J Virol. 2000; 74(12): 5679-90).

Human Rhinoviruses (HRVs) are among the most common of human pathogens. It is estimated that each year the common cold is responsible for about 20 million missed work days, 22 million missed school days, and 27 million physician visits in the United States alone (Adams, Hendershot et al. 1999; Turner 2001; Mackay 2008). In addition, tens of billions of dollars per year are spent on prescription and over-the-counter medicines associated with treatments for the common cold (Bertino 2002). The estimated overall economic impact of colds in the U.S. in 2008 was nearly $40 billion a year composed of $17 billion from direct medical costs and $22.5 billion in indirect costs.

HRV is a highly contagious human pathogen that causes respiratory tract symptoms related to "the common cold"

and exacerbates asthma and chronic pulmonary diseases. HRV is an unenveloped virus of the family Picornaviridae and is composed of 60 copies each of the viral capsid proteins VP-1, VP-2, VP-3, and VP4 and one copy of positive-sense RNA. The capsid proteins are translated in a genome-length polyprotein and cleaved to mature proteins by the viral protease-3C. The capsid proteins mediate binding to the cell receptor to facilitate virus entry and contain the primary virus neutralizing epitopes for immune targeting. HRV exists as a large number of serotypes dually classified based on 1) cell receptor usage and 2) antigenic relatedness. Viruses in the major group utilize the ICAM-1 receptor and those in the minor group use several members of the low density lipoprotein receptor that are almost ubiquitously expressed on many cell types. The serotypes are arranged with at least 3 clades (HRV-A, HRV-B, and HRV-C) based on genetic relationships.

To develop a strategy to overcome strain-specific immunity, it is necessary to understand the nature of native immune responses against HRV and other related members of the picornaviridae family. Within 2-3 weeks of infection or immunization with HRV virions, the immune system responds by developing humoral responses containing high titers of neutralizing antibody that are thought to help clear virus infections. However, the antibodies are directed against a small number of immune dominant epitopes that are located with genetically variable regions of the capsid proteins. Thus, infection or immunization with a virus or vaccine derived from one strain does not stimulate protective immunity against others. Because of the ubiquity of numerous HRV strains, vaccines that stimulate protection against one or a few serotypes are not effective.

Immune Refocusing Technology (IRT) was developed to over strain-specific immunity by reducing the antigenicity of immunodominant epitopes responsible for the strain-specific immune reactions. Using IRT, immunodominant epitopes are altered by site-specific mutagenesis to allow the immune system to develop responses to previously subdominant epitopes that participate in the development of more broadly protective immune responses.

Figure 1:
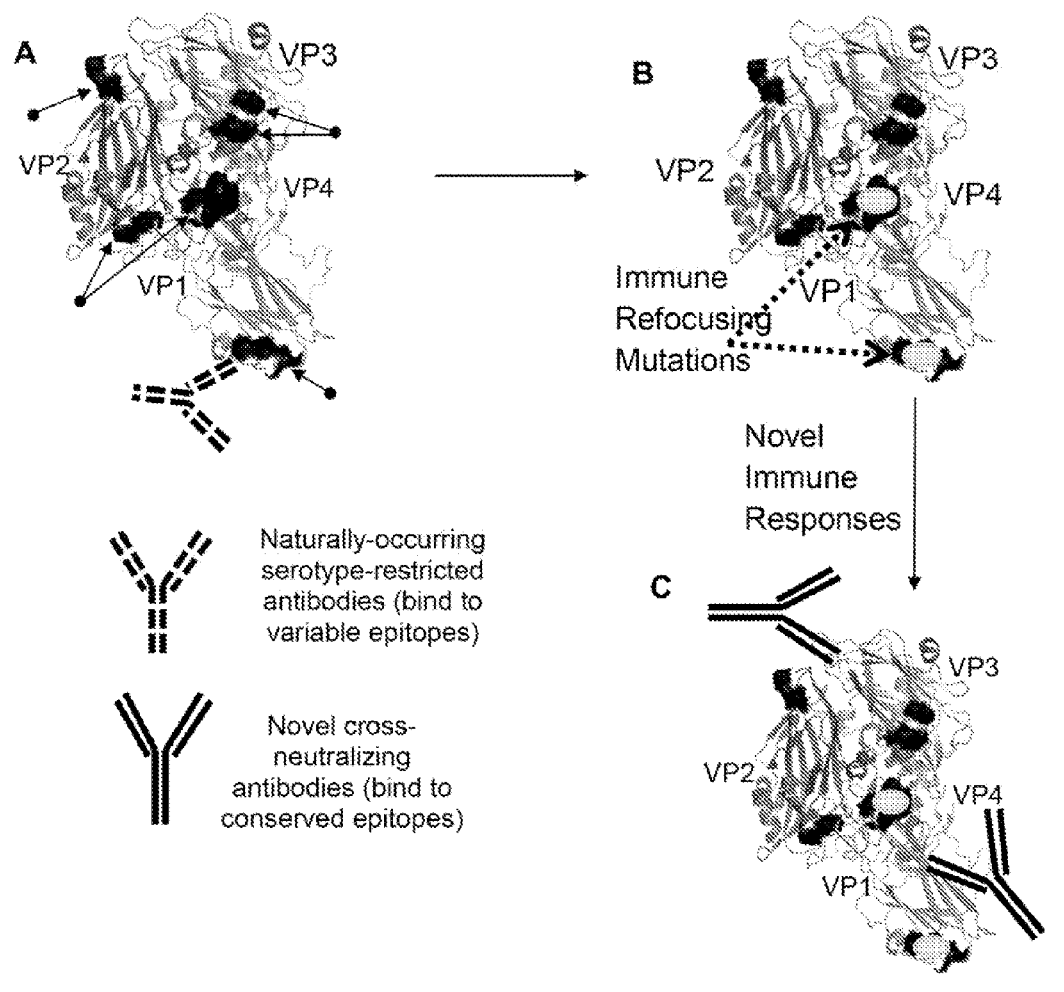

FIG. 1 shows a diagram that described IRT using a model representing the trimeric influenza A/Aichi/68 hemagglutinin (HA) structure. In the molecule in Panel A, strain-specific antibodies (identified as naturally-occurring antibodies) are produced against highly variable immunodominant epitopes (shown as the blackened residues and identified with arrows). Using IRT, specific amino acid residues in the immunodominant epitopes are altered to reduce the antigenicity of the epitopes (depicted as light gray ovals). The rationally designed IIA molecule stimulates the production of antibodies to previously subdominant epitopes. The newly refocused antibodies (shown as novel cross-neutralizing antibodies) have enhanced cross-protective antiviral activities against heterologous viruses. In addition, the rationally designed antigen can be used to derive novel therapeutic antibodies with enhanced cross-protective properties.

The IRT can be applied to derive improved HRV vaccines that stimulate enhanced cross-protective immunity against multiple strains. Rationally designed immunogens can be engineered with mutations in the immunodominant epitopes such that the immune system responds against more broadly protective subdominant epitopes. The novel immunogens can be incorporated into whole virus particles or expressed as recombinant subunit antigens for vaccine production.

SUMMARY OF THE INVENTION

The invention relates, in part, to novel HRV antigens with enhanced or novel immunogenicity. An HRV composition of interest can serve as an improved vaccine, resulting from modifications providing the virus or viral antigen with a different array of and/or newly recognizable epitopes. In addition, the novel HRV composition can serve as an antigen for the purpose of developing improved antibodies for therapeutic, diagnostic, or research reagent uses.

The more efficient and rapid use of recombinant technology coupled to a novel immune refocusing technology results in subunit compositions that greatly change the current practice of vaccine development by generating an HRV vaccine with improved effectiveness and an enhanced ability to stimulate increased cross-protective immune responses.

The invention relates, in part, to the rational design of improved antigens and is independent of vector or delivery systems. Recombinant proteins produced in bacteria, yeast, insect cells, or mammalian cells can incorporate the novel HRV antigens. In addition, recombinant viruses, such as reverse engineered HRV virions, can serve as vehicles for production and delivery of the novel antigens.

Additional features and advantages are described herein, and will be apparent from, the following Detailed Description.

BRIEF DESCRIPTION OF THE DRAWINGS

FIG. 1. Diagram of immune refocusing technology using HRV2 as an example. Cartoon depicting immune refocusing technology as applied to HRV. A. Structural cartoon of HRV2 with capsid antigens VP1, VP2, VP3, and VP4 shows in ribbon form. Amino acid residues in immunodominant epitopes that stimulate serotype-restricted antibodies are shown in surface smoothing black and identified with arrows. B. Structural cartoon with immune refocusing mutations introduced into immunodominant epitope(s) in VP1 shown as gray ovals. C. Immune refocused HRV2 antigen shown with novel broadly cross-neutralizing antibodies attached to conserved domains. Structure shown in adapted from structure IFPN.pdb from Verdaguer et al., 2000.

FIG. 4 Alignment of portions of the HRV39 and HRV2 capsid sequences with identification of antibody contact points (bold typeface) and amino acid residues adjacent to contact points (underlined). Identification of capsid epitopes A, B, and C is indicated above the lines. Amino acid numbering refers to the start of the mature capsid polyprotein. In SEQ NOs:1 and 2, the numbers in the parentheses indicate the number of amino acids deleted from the figure.

FIG. 5 Examples of first generation HRV39 immune refocused mutations. Changed residues indicated by amino acid letters, unchanged residues represented by dashes. Sequences above can be localized in the polyprotein using residue numbers provided in FIG. 4.

FIG. 7 provides a listing of the serotypes of HRV analyzed for cross-neutralization.

FIG. 8. List of HRV serotypes neutralized by sera from rabbits immunized with HRV39 immune refocused subunit antigens. The sera from rabbits immunized with IRT antigens were incubated 1 h with 1000 TCID50 of each virus at a final dilution of 1:8 in PBS. Sera from non-immune rabbits were used as negative controls for neutralization and incubated with virus at a final dilution of 1:2. The virus-serum mix was placed onto duplicate wells in a 48-well plate for 1 h. The monolayers were washed with media, overlaid with media, incubated for 2-4 days at 35 C, and examined microscopically for signs of virus infection. Wells were scored for cytopathic effects of the virus on a scale of 0 to 10. After at least three sessions of analysis, the scores were analyzed for difference from the scores obtained from non-immune sera using the Student's T test. HRV serotypes neutralized by the sea at a confidence level of 95% are listed.

FIG. 9 Examples of immune refocused derivatives of HRV16. The upper line of each sequence presents the unmodified (WT) amino acid sequences in and around the major defined epitopes. The lower line shows examples of the IRT mutations with substituted residues.

FIG. 10 List of HRV serotypes neutralized by sera from rabbits immunized with HRV16 immune refocused virions. The sera from rabbits immunized with IRT antigens were incubated 1 h with 1000 TCID50 of each virus at a final dilution of 1:8 in PBS. Sera from non-immune rabbits were used as negative controls for neutralization and incubated with virus at a final dilution of 1:2. The virus-serum mix was placed onto duplicate wells in a 48-well plate for 1 h. The monolayers were washed with media, overlaid with media, incubated for 2-4 days at 35 C, and examined microscopically for signs of virus infection. Wells were scored for cytopathic effects of the virus on a scale of 0 to 10. After at least three sessions of analysis, the scores were analyzed for difference from the scores obtained from non-immune sera using the Student's T test. HRV serotypes neutralized by the sera at a confidence level of 95% are listed.

FIG. 11 Use of antibody escape mutants to identify epitopes for immune refocusing and to design immune refocused antigens. HRV14 was pre-incubated with either polyclonal anti-HRV sera raised in rabbits against purified HRV14 or monoclonal antibody (MoAb-17) directed to the immunodominant epitope (B Sherry, A G Mosser, R J Colonno, R R Rueckert. User of monoclonal antibodies to identify four neutralization immunogens on a common cold picornavirus, human rhinovirus 14 J Virol. 1986 January; 57(1): 246-257; B Sherry, R Rueckert. Evidence for at least two dominant neutralization antigens on human rhinovirus 14. J Virol. 1985 January; 53(1): 137-143.) After 3 or 6 days, virus progeny were harvested from the monolayers, plaque purified, and sequenced in the capsid gene region. The panels report the sequence divergences observed in comparison to the parental HRV14 capsid sequences. Numbering of amino acids is from the start of each capsid protein. Dashes or blank cells indicate no change from the parental sequence. Panel A: 3 passages with incubation of HRV14 with MoAb-17. Panel B: 6 passages with incubation of HRV14 with MoAb-17. Panel C: 3 passages with incubation of HRV14 with polyclonal anti-HRV14. The results identify amino acids that can be targeted for immune refocusing.

DETAILED DESCRIPTION OF THE INVENTION

Figure 2:
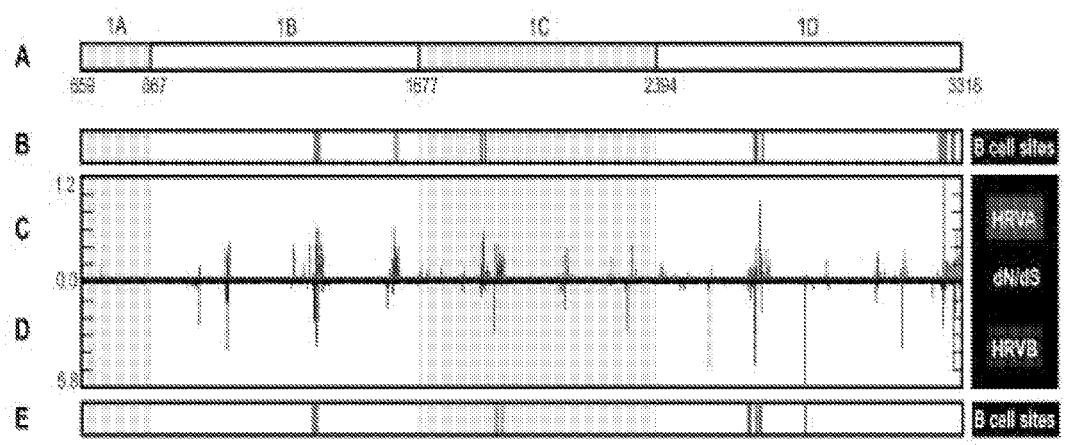
FIG. 2. Location of selective pressure and known immunogenic sites in capsid genes. A. Capsid region of HRV genome. B. Location of HRV-A B-cell antigenic sites are shown as lines in the rectangle representing the capsid precursor protein based on studies of HRV2 (Appleyard et al., 1990; Hastings et al., 1990; Speller et al., 1993; Hewat and Blaas, 996; Hewat et al., 1998). C, D. dN/dS plot for capsid genes of HRV-A and HRV-B, respectively. E. Location of HRV-B antigenic sites NimIA, NimIB, NimII and NimIII are show as lines in the rectangle representing the capsid precursor protein based on studies of HRV14 (Sherry and Rueckert, 1985; Sherry et al., 1986). Figure from Xiang et al., 2008.

"Wild type" refers to a naturally occurring organism. The term also relates to nucleic acids and proteins found in a natural occurring organism of a naturally occurring population arising form natural processes, such as seen in polymorphisms arising from natural mutation and maintained by genetic drift, natural selection and so on, and does not include a nucleic acid or protein with a sequence obtained by, for example, purposeful modification of the sequence either through a biologically or chemically selective process or through molecular mutagenesis methods.

"Immunogen" and "antigen" are used interchangeably herein as a molecule that elicits a specific immune response, for example, containing an antibody that binds to that molecule or eliciting T cells capable of destroying or recognizing an HRV-infected cell. That molecule can contain one or more sites to which a specific antibody binds. As known in the art, such sites are known as apitopes or determinants. An antigen can be polypeptide, polynucleotide, polysaccharide, a lipid and so on, as well; as a combination thereof, such as a glycoprotein or a lipoprotein. An immunogenic compound or product, or an antigenic compound or product is one which elicits a specific immune response, which can be a humoral, cellular or both.

A vaccine is an immunogen or antigen used to generate an immunoprotective response, that is, the antibody reduces the negative impact of the immunogen or antigen found on an infectious virus, or entity expressing same, in a host. The dosage is derived, extrapolated and/or determined from preclinical and clinical studies, as known in the art. Multiple doses can be administered as known in the art, and as needed to ensure a prolonged prophylactic or anamestic (memory) state. The successful endpoint of the utility of a vaccine for the purpose of this invention is the resulting presence of an induced immune response (e.g. humoral and/or cell-mediated) resulting, for example, in the production of serum antibody, or antibody made by the host in any tissue or organ, that binds the antigen or immunogen of interest or a cellular response that recognizes the intended antigen. In some embodiments, the induced antibody in some way combines with a compound, molecule and the like carrying the cognate antigen or immunogen or directs the host to neutralize, reduce or present and/or eliminate a viral pathogen from infecting and causing serious clinical disease. Immunoprotection for the purposes of the instant invention is the surrogate marker of inducing presence of such circulating anti-viral antibody that binds the immunogen. That can be determined using any known immunoassay, such as an ELISA. Alternatively, one can use a viral neutralization assay to ascertain presence of circulating anti-viral antibody. For the purposes of the instant invention, observing immunoprotection, that is, presence of circulating anti-HRV antibody, of at least thirty days is evidence of efficacy of a vaccine of interest. The time of immunoprotection can be at least 45 days, at least 60 days, at least 3 months, at least 4 months, at least 5 months, at least 6 months, at least 1 year, at least 2 years or longer. Preferably the immunoprotection is observed in outbred populations, different geographic populations, clades and so on. Successful measurements of vaccine outcomes may include, but are not exclusively confined to, immunity that either protects against infection or reduces disease or infectivity upon infection.

"Immunodominant epitope" is an epitope that selectively provokes an immune response in a host organism to the effective or functional exclusion, which may be partial or complete, of other epitopes on that antigen. A "subdominant epitope," is one which is not immunodominant and often is not immunogenic because the host preferentially reacts solely to the immunodominant epitope(s).

"To immunodampen and epitope" or "to immune dampen an epitope" is to modify an epitope to substantially prevent the immune system of the host organism from producing antibodies, helper or cytotoxic T cells against the dampened epitope. However, immunodampen does not necessarily result in the complete removal of said epitope. Immunodampening can exert influence on epitopes located away from the site of dampening.

Immunodampening of an immunodominant epitope of an antigen can result in the production in a host organism of high titer antibodies or T cell responses against non-dominant epitopes on that antigen and/or new titters of antibodies or T cell responses to otherwise relatively immune silent epitopes. Such immunodampened antigens can serve as effective vaccines against organisms that have an antigen with a moderately or highly variable and/or conserved immunodominant epitope(s) or as antigens for the development of novel antibodies with broadened specificities and/or therapeutic or diagnostic uses.

An immunodominant epitope can be identified by examining serum or T-cell reactivity from a host organism infected with the pathogenic organism. The serum is evaluated for content of antibodies that bind to the identified antigens, usually either as pre-existing antibodies (naive human or animal) or occurring with a short amount of time after exposure or immunization that are likely to cause an immune response in a host organism. If an immunodominant epitope is present, substantially many antibodies in the serum will bind to and/or T cells will recognize the immunodominant epitope(s), with reduced to no binding/recognition to other epitopes present in the antigen.

After an immunodominant epitope has been identified, the immunodominant epitope is immunodampened as taught herein using the materials and methods taught herein and as known in the art as a design choice. The process of immunodampening can be performed through a variety of methods including, but not limited to, site-specific mutagenesis, antibody-induced evolution, or other in vitro or in vivo selection methods using native or recombinant reagents.

A particular amino acid of the immunodominant epitope can be replaced, substituted or deleted to dampen immunogenicity. Immunodampening can occur by replacing, substituting or eliminating one amino acid, two amino acids, three amino acids or more of the immunodominant epitope, for example, by site directed mutagenesis of the nucleic acid encoding the antigen with another amino acid(s) which are less immunogenic or which changes the pattern or hierarchy of immunogenicity. Methods for altering nucleic acids and/ or polypeptides are provided herein, and are known in the art.

Alternatively, a sequence that leads to a post-translational modification of an amino acid such as glycosylation, acetylation, or other modification can be introduced or eliminated to immunodampen an immunodominant epitope. Methods for altering nucleic acids to introduce or remove post-translational modifications are provided herein, and are known in the art.

The phrases and terms, as well as combinations thereof, "functional fragment, portion, variant, derivative or analog" and the like, as well as forms thereof, of an HRV antigen, component, subunit, VP-1, VP-2, VP-3, VP-4, protease, capsomer, virus-like particle, and the like thereof relate to an element having qualitative biological activity in common with the wild-type or parental element from which the variant, derivative, analog and the like was derived. For example, a functional portion, fragment or analog of HRV is one which stimulates an immune response as does native HRV, although the response may be to different epitopes on virus.

Thus, included within the scope of the invention are functional equivalents of a virus, or portion or derivative thereof, of interest. The term "functional equivalents" includes the virus and portions thereof with the ability to stimulate an immune response to HRV.

Parts of an HRV of interest, such as a whole virions or subunits carrying, for example, capsid proteins, as well as preparations of any other HRV antigens can be obtained practicing methods known in the art. The parts can be produced through purification of materials from either native virus infections or from recombinant methods using a variety of nucleic acid expression vectors or recombinant virus vectors known in the art. When one or more immunodominant, strain specific epitopes are removed or dampened, for example, by intramolecular modifications (e.g. deletions, charge changes, altering post-translational modifications and so on) and given as an antigen to a naive animal, the novel immunogen can induce a new hierarchy of immune responses at either or both the B and T cell levels (Garrity et al., J Immunol. (1997) 159(1):279-89) against subdominant or previously silent epitopes. That technology as described herein is known the "Immune Refocusing" method of rational antigen design.

Thus, a vaccine derived from a recombinant HRV capsid subunit protein, an engineered virus-like particle, a recombinant virus vector or vehicle (e.g., adenovirus, vaccinia virus, bacteriophage or other virus-derived system) can be sufficient to protect against challenge from plural strains of HRV.

Immunodampening can be affected by any of a variety of techniques such as, altering or deleting specific amino acids of the epitope, or adding or removing, for example, a glycosylation site at or near the epitope. The changes can be effected at the level of the polypeptide or at the level of the polynucleotide, practicing methods known in the art. Immunodampening can also be affected by genetic methods such as selection of naturally occurring or experimentally induced mutations from nucleic acid or protein libraries.

Once a change is made, one then determines whether the change alters, such as, reduced the reactivity of the immunodominant epitope now modified, the "dampened epitope, antigen and so on." That can be tested in vitro by determining the reactivity of the dampened antigen with defined antisera known to react with the dominant epitope, such as by an ELISA or Western blot, for example. Candidates demonstrating reduced reactivity with those defined antisera are chosen for testing in vivo to determine wither those dampened antigens are immunogenic and the host generates an immune response thereto. Hence, for example, a mouse or other animal is immunized to the dampened antigen as known in the art, serum obtained and tested in an in vitro assay for reactivity therewith. That antiserum then can be tested on wild-type virus to determine if the antibody still recognizes the wild type epitope or the wild type antigen. That can be done, for example, in an ELISA or a Western blot. The latter can be informative, revealing whether the particular immunodominant epitope is bound, and if the antiserum remains reactive with HRV, the size and possibly, the identity of the molecule carrying the epitope reactive with the mouse antiserum.

Those candidate immunodampened antigens less or no longer reactive with known antisera that bind to the parent immunodominant antigen, yet remain immunogenic is hosts, are selected as candidate vaccines for further testing. For example, if the altered molecule is administered to a mouse, the mouse antiserum thereto can be tested for reactivity with a number of HRV strains in standardized anti-viral-based assays to determine how generic that antibody is, that is, whether the newly recognized epitopes on the dampened antigen are generic to a wide range of HRV strains and if the antibody has antiviral activity.

Many techniques are available to one of ordinary skill in the art to permit manipulation of immunogenic structures. The techniques can involve substitution of various amino acid residues at a site of interest, followed by a screening analysis of binding of the mutein to defined, known antibody that binds to one or more immunodominant epitopes of HRV. For example, a polypeptide can be synthesized to contain one or more changes to the primary amino acid sequence of the immunodominant epitope. Alternatively, the nucleic acid sequence of the immunodominant epitope can be modified to express an immunodampened epitope. Hence, the nucleic acid sequence can be modified by, for example, site directed mutagenesis to express amino acid substitutions, insertions, additions, deletions and the like, some of which may introduce further modification at or near the immunodominant epitope, such as, altering sites that lead to post-translational modifications such as addition or subtraction of carbohydrate, fatty acids and so on. Mutations to the nucleotide, and resulting polypeptide, sequences can also be made through in vitro or in vivo selection processes, also known in the art.

One procedure for obtaining epitope mutants (a mutant epitope that varies from wildtype) and the like is "alanine scanning mutagenesis" (Cunningham & Wells, Science 244: 1081-1085 (1989); and Cunningham & Wells, Proc Nat. Acad Sci USA 84:6434-6437 (1991)). One or more residues are replaced by alanine or polyalanine residue(s). Those residues demonstrating functional sensitivity to the substitutions then can be refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues.

A more systematic method for identifying amino acid residues to modify comprises identifying residues involved in immune system stimulation or immunodominant antibody recognition and those residues with little or no involvement with immune system stimulation or immunodominant antibody recognition. An alanine scan of the involved residues is performed, with each ala mutant tested for reducing immune system stimulation to an immunodominant epitope or immunodominant antibody recognition. In another embodiment, those residues with little or no involvement in immune system stimulation are selected to be modified. Modification can involve deletion of a residue or insertion of one or more residues adjacent to a residue of interest. However, normally the modification involves substitution of the residue by another amino acid. A conservative substitution can be a first substitution. If such a s substitution results in reduction of immune system stimulation or reduced reactivity with known immunodominant antibody, then another conservative substitution can be made to determine if more substantial changes are obtained.

Even more substantial modification in the ability to alter the immune system response away from the immunodominant epitope can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

A more rational design strategy, used by immune refocusing, takes into account the key residues in the epitopes that are most responsible for the immune responses and for antibody-antigen binding. Substitution of these key residues enables a more efficient analysis as the mutational strategy focuses on the most important elements of an epitope rather than inserting random substitutions in random sites. Immune refocusing mutations typically focus on these key residues with substitutions of amino acids of similar nature, such as a substitution of glutamine (Gln, Q) for glutamic acid (Glu, E), and the like.

For example, the naturally occurring amino acids can be divided into groups based on common side chain properties:
(1) hydrophobic: methionine (M or met), alanine (A or ala), valine (V or val), leucine (L or leu) and isoleucine (I or ile);
(2) neutral, hydrophilic: cysteine (C or cys), serine (S or ser), threonine (T or thr), asparagine (N or asn) and glutamine (Q or gln);
(3) acidic: aspartic acid (D or asp) and glutamine acid (E or glu);
(4) basic: histidine (H or his), lysine (K or lys) and arginine (R or arg);
(5) residues that influence chain orientation: glucine (G or gly) and proline (P or pro), and
(6) aromatic: tryptophan (W or trp), tyrosine (Y or tyr) and phenylalanine (F or phe).

Non-conservative substitutions can entail exchanging an amino acid with an amino acid from another group. Conservative substitutions can entail exchange of one amino acid for another with a group.

Preferred amino acid substitutions are those which dampen an immunodominant epitope, but can also include those which: (1) reduce susceptibility to proteolysis, (2) reduce susceptibility to oxidation, (3) alter immune system stimulating activity and/or (4) confer or modify other physico-chemical or functional properties of such analogs. Analogs can include various muteins of a sequence other than the naturally occurring peptide sequence. For example, single or multiple amino acid substitutions (preferably conservative amino acid substitutions) may be made in the naturally-occurring sequence. A conservative amino acid substitution generally should not substantially change the structural characteristics of the parent sequence (e.g., a replacement amino acid should not tend to break a helix that occurs in the parent sequence, or disrupt other types of secondary structure that characterizes the parent sequence)

unless of a change in the bulk or conformation of the R group or side chain (Proteins, Structures and Molecular Principles (Creighton, ed., W.H. Freeman and Company, New York (1984); Introduction to Protein Structure, Branden & Tooze, eds., Garland Publishing, New York, N.Y. (1991); and Thornton et al. Nature 354:105 (1991)).

Ordinarily, the epitope mutant with altered biological properties will have an amino acid sequence having at least 75% amino acid sequence identity or similarity with the amino acid sequence of the parent molecule, at least 80%, at least 85%, at least 90% and often at least 95% identity. Identity or similarity with respect to parent amino acid sequence is defined herein as the percentage of amino acid residues in the candidate sequence that are identical (i.e., same residue) or similar (i.e., amino acid residue from the same group based on common side-chain properties, supra) with the parent molecule residues, after aligning the sequences and introducing gaps, if necessary, to achieve the maximum percent sequence identity.

Covalent modifications of the molecules of interest are included within the scope of the invention. Such may be made by chemical synthesis or by enzymatic or chemical cleavage of the molecule, if applicable. Other types of covalent modifications of the molecule can be introduced into the molecule by reacting targeted amino acid residues of the molecule with an organic derivatizing agent that is capable of reacting with selected side chains or with the N-terminal or C-terminal residue.

Cysteinyl residues can be reacted with α-haloacetates (and corresponding amines), such as chloroacetic acid or chloroacetamide, to yield carboxylmethyl or carboxyamidomethyl derivatives. Cysteinyl residues also can be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercura-4-nitrophenol or chloro-7-nitrobenzo-2-oxa-1,3-diazole, for example.

Histidyl residues can be derivatized by reaction with diethylpyrocarbonate at pH 5.5-7.0. p-bromophenacyl bromide also can be used, the reaction is preferably performed in 0.1 M sodium cacodylate at pH 6.0.

Lysinyl and α terminal residues can be reacted with succinic or other carboxylic acid anhydrides to reverse the charge of the residues. Other suitable reagents for derivatizing α-amino-containing residues include imidoesters, such as, methyl picolinimidate, pyridoxal phosphate, pyridoxal, chloroborohydride, trinitrobenzenesulfonic acid, O-methylisourea and 2,4-pentanedione, and the amino acid can be transaminase-catalyzed with glyoxylate.

Arginyl residues can be modified by reaction with one or several conventional reagents, such as, pheylglyoxal, 2,3-butanedione, 1,2-cyclohexanedione and ninhydrin. Derivatization of arginine residues often requires alkaline reaction conditions. Furthermore, the reagents may react with lysine as well as the arginine ε-amino group.

The specific modification of tyrosyl residues can be made with aromatic diazonium compounds or tetranitromethane. For example, N-acetylimidizole and tetranitromethane can be used to form O-acetyl tyrosyl species and 3-nitro derivatives, respectively. Tyrosyl residues can be iodinated using $^{125}I$ or $^{131}I$ to prepare labeled proteins for use in a radioimmunoassay or with other radionuclides to serve as an imaging means.

Carboxyl side groups (aspartyl or glutamyl) can be modified by reaction with carbodiimides (R—N=C=C—R'), where R and R' can be different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonium ions.

Glutaminyl and asparaginyl residues are frequently deamidated to the corresponding glutamyl and aspartyl residues, respectively, under neutral or basic conditions. The deamidated form of those residues falls within the scope of this invention.

Other modifications include hydroxylation of proline and lysine, phosphorylation of hydroxyl groups of serinyl or threonyl residues, methylation of the α-amino groups of lysine, arginine, and histidine side chains (Creighton, Proteins: Structure and Molecular Properties, W.H. Freeman & Co., San Francisco, pp. 79-86 (1983)), and acetylation of the N-terminal amine and amidation of any C-terminal carboxyl group.

Another type of covalent modification involved chemically or enzymatically coupling glycosides to the molecules of interest. Depending on the coupling mode used, the sugar(s) may be attached to: (a) arginine and histidine; (b) free carboxyl groups; (c) free sulfhydryl groups, such as those of cystine; (d) free hdyroxyl groups, such as those of serine, threonine or hydroxyproline; (e) aromatic residues such as those of pheylalanine, tyrosine or tryptophan; or (f) the amide group of glutamine. Such methods are described in WO 87/05330 and in Aplin & Wriston, CRC Crit Rev Biochem, pp. 259-306 (1981).

Removal of any carbohydrate moieties present on the molecule of interest may be accomplished chemically or enzymatically. Chemical deglycosylation, for example, can require exposure of the molecule to the compound, trifluoromethanesulfonic acid, or an equivalent compound, resulting in the cleavage of most or all sugars except the linking sugar (N-acetylglucosamine or N-acetylgalactosamine), while leaving the remainder of the molecule intact. Chemical deglycosylation is described, for example, in Hakimuddin et al., Arch Biochem Biophys 259:52 (1987) and in Edge et al., Anal Biochem 118:131 (1981). Enzymatic cleavage of carbohydrate moieties on molecules can be achieved by any of a variety of endoglycosidases and exoglycosidases as described, for example, in Thotakura et al., Meth Enzymol 138:350(1987).

RNA or DNA encoding the VP-1, VP-2, VP-3, VP-4, protease, and the like of HRV is readily isolated and sequenced using conventional procedures (e.g., by using oligonucleotide probes that are capable of binding specifically to the relevant genes, Innis et al. in PCR Protocols. A Guide to Methods and Applications, Academic (1990), and Sanger et al., Proc Natl Acad Sci 74:5463 (1977)). Once isolated, the DNA may be placed into expression vectors, which are then transfected into host cells, including but not restricted to E. coli cells, NS0 cells, COS cells, Chinese hamster ovary (CHO) cells or myeloma cells, to obtain synthesis of the protein of interest in the recombinant host cells. The RNA or DNA also may be modified, for example, by substituting bases to optimize for codon usage in a particular host or by covalently joining to the coding sequence of a heterologous polypeptide. Such as approach would be the basis for developing a subunit vaccine.

Thus, in one embodiment, the capsid proteins of HRV39 were selected as a target for refocusing the host immune response to other non-dominant sites on the virus particle as novel targets for an immunoprotective response, preferably one of broad scope and spectrum active on a wide variety of strains and so on.

The above alterations to immunodominant sites can be obtained by cloning, site directed mutagenesis, amplification, immune or drug selection, and so on, using a molecular method, a biological method or both, as known in the art.

To streamline approval from regulatory agencies, such as the US Food and Drug Administration or European Medicines Agency for human products and the US Department of Agriculture for veterinary products, biological pharmaceutics must meet purity, safety and potency standards defined by the pertinent regulatory agency. To produce a vaccine that meets those standards, the recombinant organisms can be maintained in culture media that is, for example, certified free of transmissible spongiform encephalopathies (herein referred to as "TSE").

Preferably, plasmids harboring the vaccine-encoding sequence carry a non-antibiotic selection marker, since it is not always ideal to use antibiotic resistance markers for selection and maintenance of plasmids in mycobacteria that are designed for use in humans and veterinary pharmaceutics, although a preferred embodiment relates to use of a recombinant subunit vaccine. In one embodiment, therefore, the present invention provides a selection strategy in which, for example, a catabolic enzyme is utilized as a selection marker by enabling the growth of bacteria in medium containing a substrate of said catabolic enzyme as a carbon source. An example of such a catabolic enzyme includes, but it not restricted to, lacYZ encoding lactose uptake and β-galactosidase (Genbank Nos. J01636, J01637, K01483 or K01793). Other selection markers that provide a metabolic advantage in defined media include, but are not restricted to, galTK (GenBank No. X02306) for galactose utilization, sacPA (GenBank No. J03006) for sucrose utilization, trePAR (GenBank No. Z54245) for trehalose utilization, xylAB (GenBank No. CAB13644 and AAB41094) for xylose utilization etc. Alternatively, the selection can involve the use of antisense mRNA to inhibit a toxic allele, such as the sacB allele (GenBank No. NP_391325).

The immunogen of the present invention may be used to treat a human. In one embodiment, the immunogen of interest is administered to a nonhuman mammal for the purpose of obtaining preclinical data, for example. Exemplary nonhuman mammals include nonhuman primates, dogs, cats, rodents and other mammals. Such mammals may be established animal models for a disease to be treated with the formulation, or may be used to study toxicity of the immunogen of interest. In each of those embodiment, dose escalation studies may be performed in the mammal. A product of the invention of interest can be used to treat same.

The specific method used to formulate the novel vaccines and formulations described herein is not critical to the present invention and can be selected from or can include a physiological buffer (Felgner et al., U.S. Pat. No. 5,589,466 (1996)); aluminum phosphate or aluminum hydroxyphosphate (e.g. Ulmer et al., Vaccine, 18:18 (2000)), monophosphoryl-lipid A (also referred to as MPL or MPLA; Schneerson et al. J. Immunol., 147:2136-2140 (1991); e.g. Sasaki et al. Inf. Immunol., 65:3520-3528 (1997); and Lodmell et al., Vaccine, 18:1059-1066 (2000)), QS-21 saponin (e.g. Sasaki et al., J. Virol., 72:4931 (1998)); dexamethasone (e.g., Malone et al., J. Biol. Chem. 269:29903 (1994)); CpG DNA sequences (Davis et al., J. Immunol., 15:870 (1998)); interferon-α (Mohanty et al., J. Chemother. 14(2):194-197, (2002)), lipopolysaccharide (LPS) antagonist (Hone et al., J. Human Virol., 1: 251-256 (1998)) and so on.

The formulation herein also may contain more than one active compound as necessary for the particular indication being treated, preferably those with complementary activities that do not adversely impact each other. For example, it may be desirable to further provide an adjuvant. Such molecules suitably are present in combination in amounts that are effective for the purpose intended. The adjuvant can be administered sequentially, before or after antigen administration. Adjuvants are known and examples include aluminum salts, salts of calcium, salts of iron, salts of zinc, insoluble suspensions of acylated tyrosine, acetylated sugars, cationically or anionically derived polysaccharides and polyphosphazenes.

The immunogen of interest can be used with a second component, such as a therapeutic moiety conjugated to or mixed with same, administered as a conjugate, separately in combination, mixed prior to use and so on as a therapeutic, see, for example, Levine et al., eds., New Generation Vaccines, $2^{nd}$ Marcel Dekker, Inc., New York, N.Y., 1997). The therapeutic agent can be any drug, vaccine and the like used for an intended purpose. Thus, the therapeutic agent can be a biological, a small molecule and so on. The immunogen of interest can be administered concurrently or sequentially with a second HRV immunogenic composition, immunodampened or not, for example. thus, an immunodampened antigen of interest can be combined with an existing vaccine, although that approach would minimize the use thereof it the existing vaccine is made in eggs.

The term "small molecule" and analogous terms include, but are not limited to, peptides, peptidomimetics, amino acids, amino acid analogues, polynucleotides, polynucleotide analogues, carbohydrates, lipids, nucleotides, nucleotide analogues, organic or inorganic compounds (i.e., including heterorganic and/organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, combinations thereof and other pharmaceutically acceptable forms of such compounds which stimulate an immune response or are immunogenic, or have a desired pharmacologic activity.

Thus, the immunogen of the invention may be administered alone or in combination with other types of treatments, including a second immunogen or a treatment for the disease being treated. The second component can be an immunostimulant.

In addition, the immunogen of the instant invention may be conjugated to various effector molecules such as heterologous polypeptides, drugs, radionucleotides and so on, see, e.g., WO 92/08495; WO 91/14438; WO 89/12624; U.S. Pat. No. 5,314,995; and EPO 396,387. An immunogen may be conjugated to a therapeutic moiety such as an antibiotic (e.g., a therapeutic agent or a radioactive metal ion (e.g., α emitters such as, for example, $^{213}Bi$)) or an adjuvant.

Therapeutic compounds of the invention alleviate at least one symptom associated with a target disease, disorder, or condition amenable for treatment with an immunogen of interest. The products of the invention may be provided in pharmaceutically acceptable compositions as known the art or as described herein. The terms "physiologically acceptable," "pharmacologically acceptable" and so on mean approved by a regulatory agency of the Federal or a state government or listed in the U.S. Pharmacopeia or other generally recognized pharmacopeia for use in animals and more particularly in humans.

The products of interest can be administered to a mammal in any acceptable manner. Methods of introduction include, but are not limited to, parenteral, subcutaneous, intraperitoneal, intrapulmonary, intranasal, epidural, inhalation and oral routes, and if desired for immunosuppressive treatment, intralesional administration. Parenteral infusions include intramuscular, intradermal, intravenous, intraarterial or intraperitoneal administration. The products or compositions may be administered by any convenient route, for example, by infusion or bolus injection, by absorption through epithelial or mucocutaneous linings (e.g., oral mucosa, rectal and intestinal mucosa etc.) and may be administered together with other biologically active agents. Administration can be systemic or local. In addition, it may be desirable to introduce the therapeutic products or compositions of the invention into the central nervous system by any suitable route, including intraventricular and intrathecal injection; intraventricular injection may be facilitated by an intraventricular catheter, for example, attached to a reservoir, such as an Ommaya reservoir. In addition, the product can be suitable administered by pulse infusion, particularly with declining doses of the products of interest. Preferably the dosing is given by injection, preferably intravenous or subcutaneous injections, depending, in part, on whether the administration is brief or chronic.

Various other delivery systems are known and can be used to administer a product of the present invention, including, e.g., encapsulation in liposomes, microparticles or microcapsules (see Langer, Science 249:1527 (1990); Liposomes in the Therapy of Infectious Disease and Cancer, Lopez-Berestein et al., eds., (1989)).

The active ingredients may be entrapped in a microcapsule prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, A. Osal, Ed. (1980).

Respiratory tract or pulmonary administration can also be employed, e.g., by use of an inhaler or nebulizer, and formulation with an aerosolizing agent. The composition of interest may also be administered into the upper respiratory tract lungs of a patient in the form of a dry powder composition, see e.g., U.S. Pat. No. 6,514,496.

It may be desirable to administer the therapeutic products or compositions of the invention locally to the area in need of treatment; that may be achieved by, for example, and not by way of limitation, local infusion, topical application, by injection, by means of a catheter, by means of a suppository or by means of an implant, said implant being of a porous, non-porous or gelatinous material, including hydrogels or membrane, such as sialastic membranes or fibers. Preferably, when administering a product of the invention, care is taken to use materials to which the protein does not absorb or adsorb.

In yet another embodiment, the product can be delivered in a controlled release system. In one embodiment, a pump may be used (see Langer, Science 249:1527 (1990); Sefton, CRC Crit Ref Biomed Eng 14:201 (1987); Buchwald et al., Surgery 88:507 (1980); and Saudek et al., N Engl J Med 321:574 (1989)). In another embodiment, polymeric materials can be used (see Medical Applications of Controlled Release, Langer et al., eds., CRC Press (1974); Controlled Drug Bioavailability, Drug Product Design and Performance, Smolen et al., eds., Wiley (1984); Ranger et al., J Macromol Sci Rev Macromol Chem 23:61 (1983); see also Levy et al., Science 228:190 (1985); During et al., Ann Neurol 25:351 (1989); and Howard et al., J Neurosurg 71:105 (1989)). In yet another embodiment, a controlled release system can be placed in proximity of the therapeutic target.

The compositions can take the form of solutions, suspensions, emulsion, tablets, pills, capsules, powders, sustained-release formulations, depots and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate etc. Examples of suitable carriers are described in "Remington's Pharmaceutical Sciences," Martin. Such compositions will contain an effective amount of the immunogen preferably in purified form, together with a suitable amount of carrier so as to provide the form for proper administration to the patient. As known in the art, the formulation will be constructed to suit the mode of administration.

Sustained release preparations may be prepared for use with the products of interest. Suitable examples of sustained release preparations include semi-permeable matrices of solid hydrophobic polymers containing the immunogen, which matrices are in the form of shaped articles, e.g., films or matrices. Suitable examples of such sustained release matrices include polyesters, hydrogels (for example, poly (2-hydroxyethylmethacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers (such as injectable microspheres composed of lactic acid-glycolic acid copolymer) and poly-D-(−)-3-hydroxyburyric acid. While polymers such as ethylene-vinyl acetate and lactic acid-glycolic acid enable release of molecules for over 100 days, certain hydrogels release cells, proteins and products for and during shorter time periods. Rational strategies can be devised for stabilization depending on the mechanism involved.

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

An "isolated" or "purified" immunogen is substantially free of contaminating proteins from the medium from which the immunogen is obtained, or substantially free of chemical precursors or other chemicals in the medium used which contains components that are chemically synthesized. The language "substantially free of subcellular material" includes preparations of a cell in which the cell is disrupted to form components which can be separated from subcellular components of the cells, including dead cells, and portions of cells, such as cell membranes, ghosts and the like, from which the immunogen is isolated or recombinantly produced. Thus, an immunogen that is substantially free of subcellular material includes preparations of the immunogen having less than about 30%, 20%, 25%, 20%, 10%, 5%, 2.5% or 1%, (by dry weight) of subcellular contaminants.

As used herein, the terms "stability" and "stable" in the context of a liquid formulation comprising an immunogen refer to the resistance of the immunogen in a formulation to thermal and chemical aggregation, degradation or fragmentation under given manufacture, preparation, transportation and storage conditions, such as, for one month, for two months, for three months, for four months, for five months, for six months or more. The "stable" formulations of the invention retain biological activity equal to or more than 80%, 85%, 90%, 95%, 98%, 99% or 99.5% under given manufacture, preparation, transportation and storage conditions. The stability of said immunogen preparation can be assessed by degrees of aggregation, degradation or fragmentation by methods known to those skilled in the art, including, but not limited to, physical observation, such as, with a microscope, particle size and count determination and so on, compared to a reference.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixtures, citric acid-monosodium citrate mixture etc.), succinate buffers (e.g., succinic acid-monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, glyconic acid-sodium hydroxide mixture, gluconic acid-potassium gluconate mixture etc.), oxalate buffers (e.g., oxalic acid-sodium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyalconium halides (e.g., chloride, bromide and iodide), hexamethonium chloride, alkyl parabens, such as methyl or propyl paraben, catechol, resorcinol, cyclohexanol and 3-pentanol.

Isotonicifiers are present to ensure physiological isotonicity of liquid compositions of the instant invention and include polyhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, sylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thiogycerol, α-monothioglycerol and sodium thiosulfate; low molecular weight polypeptides (i.e., <10 residues); protein, such as human serum albumin, bovine serum albumin, gelatin or immunoglubulins; hydrophilic polymers, such as polyvinylpyrrolidone, saccharides, monosaccharides, such as xylose, mannose, fructose or glycose; disaccharides, such as lactose, maltose and sucrose; trisaccharides, such as raffinose, polysaccharides, such as, dextran and so on. Stabilizers can be present in the range from 0.1 to 10,000 w/w per part of immunogen.

Additional miscellaneous excipients include bulking agents, (e.g., starch), chelating agents (e.g., EDTA), antioxidants (e.g., ascorbic acid, methionine or vitamin E) and cosolvents.

As used herein, the term "surfactant" refers to organic substances having amphiphatic structures, namely, are composed of groups of opposing solubility tendencies, typically an oil-soluble hydrocarbon chain and a water-soluble ionic group. Surfactants can be classified, depending on the charge of the surface-active moiety, into anionic, cationic and nonionic surfactants. Surfactants often are used as wetting, emulsifying, solubilizing and dispersing agents for various pharmaceutical compositions and preparations of biological materials.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

As used herein, the term, "inorganic salt," refers to any compound, containing no carbon, that results from replacement of part or all of the acid hydrogen or an acid by a metal or a group acting like a metal, and often is used as a tonicity adjusting compound in pharmaceutical compositions and preparations of biological materials. The most common inorganic salts are NaCl, KCl, $NaH_2PO_4$ etc.

The present invention can provide liquid formulations of an immunogen having a pH ranging from about 5.0 to about 7.0, or about 5.5 to about 6.5, or about 5.8 to about 6.2, or about 6.0, or about 6.0 to about 7.5, or about 6.5 to about 7.0.

The instant invention encompasses formulations, such as, liquid formulations having stability at temperatures found in a commercial refrigerator and freezer found in the office of a physician or laboratory, such as from about −20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10% (w/v).

The formulations to be used for in vivo administration must be sterile. That can be accomplished, for example, by filtration through sterile filtration membranes. For example, the subcellular formulations of the present invention may be sterilized by filtration.

The immunogen composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the immunogen thereof to be administered will be governed by such considerations, and can be the minimum amount necessary to prevent, ameliorate or treat a targeted disease, condition or disorder.

The amount of antigen is not critical to the present invention but is typically an amount sufficient to induce the desired humoral and cell mediated immune response in the target host. The amount of immunogen of the present invention to be administered will vary depending on the species of the subject, as well as the disease or condition that is being treated. Generally, the dosage employed can be about 10-1500 µg/dose.

As used herein, the term "effective amount" refers to the amount of a therapy (e.g., a prophylactic or therapeutic agent), which is sufficient to reduce the severity and/or duration of a targeted disease, ameliorate one or more symptoms thereof, prevent the advancement of a targeted disease or cause regression of a targeted disease, or which is sufficient to result in the prevention of the development, recurrence, onset, or progression of a targeted disease or one or more symptoms thereof. For example, a treatment of interest can increase survivability of the host, based on baseline or a normal level, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another embodiment, an effective amount of a therapeutic or a prophylactic agent reduces the symptoms of a targeted disease, such as a symptom of HRV by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Also used herein as an equivalent is the term, "therapeutically effective amount."

Where necessary, the composition may also include a solubilizing agent and a local anesthetic such as lidocaine or other "caine" anesthetic to ease pain at the site of the injection.

Generally, the ingredients are supplied either separately or mixed together in unit dosage form, for example, as a dry lyophilized powder or water-free concentration in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorder described above is provided. The article of manufacture can comprise a container and a label. Suitable containers include, for example, bottles, vials, syringes and test tubes. The containers may be formed from a variety of materials such as glass or plastic. The container holds a composition which is effective for preventing or treating a targeted condition or disease and may have a sterile access port (for example, the container may be an intravenous solution bag or a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

The instant invention also includes kits, e.g., comprising an immunogenic composition of interest, homolog, derivative thereof and so on, for use, for example, as a vaccine, and instructions for the use of same and so on. The instructions may include directions for using the composition, derivative and so on. The composition can be in liquid form or presented as a solid form, generally, desiccated or lyophilized. The kit can contain suitable other reagents, such as a buffer, a reconstituting solution and other necessary ingredients for the intended use. A packaged combination of reagents in predetermined amounts with instruction for use thereof, such as for a therapeutic use is contemplated. In addition, other additives may be included, such as, stabilizers, buffers and the like. The relative amounts of the various reagents may be varied to provide for concentrations of a solution of a reagent, which provides user flexibility, economy of space, economy of reagents and so on.

Citation of any of the references discussed hereinabove shall not be construed as an admission that any such reference is prior art to the present invention. All references cited herein are herein incorporated by reference in entirety.

The invention now will be exemplified by the following non-limiting examples.

Example 1

Cross-protective HRV antigens can be designed and developed using an immune refocusing strategy. Strain-specific epitopes of HRV can be deduced through analysis of sequence variation, serology, and structural characterizations.

A significant body of published information is available on the structure, antigenic sites, and sequence of picornaviruses including rhinoviruses.

FIG. 2 presents an analysis of variation and antigenic sites based on a global alignment of all HRV-A and HRV-B serotypes (Xiang et al. 2008). Line A shows a linear representation of the P1 region which encodes the fragment of the polyprotein which is processed into VP4, VP2, VP3, and VP1 capsid proteins. Line B identifies the B cell epitopes in HRV-A strains which stimulate the dominant antibodies. C and D graphically present diversity between the serotypes in A and B strains, respectively. Line E shows he epitopes of HRV-B serotype viruses. Although the viruses differ greatly in primary amino acid sequence, the areas of diversity and B cell epitopes align.

Structural data aid in understanding the mechanisms of virus attachment to cell receptors, antibodies, and antiviral molecules. These data can also be utilized to identify immunodominant epitopes in an effort to localize the likely position of immunodominant antigenic sites within the HRV39 capsid sequence. This algorithm weights various parameters such as sequence alignments, hydrophilicity, hydrophobicity, free energy of hydrophilic side chains, mobility, and charge.

Figure 3:
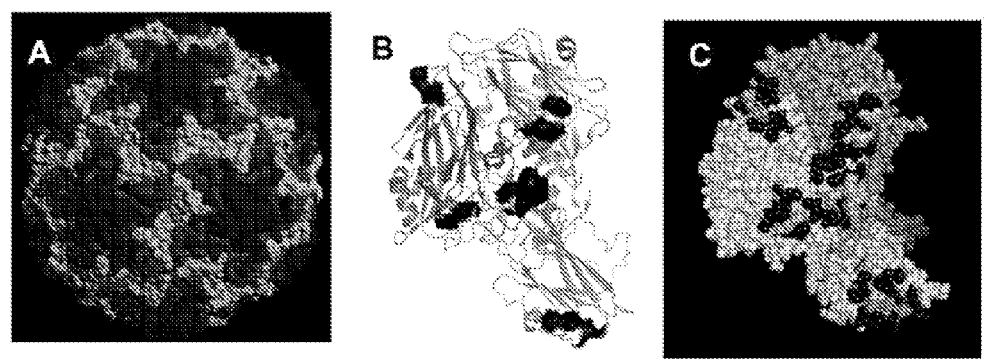
FIG. 3. Structure of HRV. A) Space-filled model showing arrangements of VP1, VP2, and VP3 forming a viral capsid. B and C) are crystal structure diagrams of capsids with the major antigenic sites accentuated using darker gray (IFPN-.pdb). HRV39 has not been crystallized but is very closely related to HRV2 shown above. B is a ribbon structure with surface-filled contouring of the minimal immunodominant strain-specific antibody contact points. C is a ball model with exposed adjacent residues (dark gray) to the epitopes identified in B. Analysis of the structure along with comparison of HRV39 sequence assists in identifying residues for immune refocusing.

Identification of immunodominant, strain-specific sites on the HRV capsid proteins can be facilitated by analysis of structural data. Although the structural analysis for each serotype has not been completed, sufficient conservation of structure between serotypes permits identification of variable regions, epitopes, and other sites. For example, structural models of HRV2 and other serotypes can be used to predict the epitopes of other serotypes such as HRV39. In FIG. 3, the antigenic sites of HRV2 have been modeled using published structures and antigenic data for all available serotypes. Although HRV2 uses the LDL receptor, it is genetically close to HRV39 (Palmenberg et al., 2009), shared 75.4% similarity with HRV39 capsids (compared to 50.4% for HRV14) and can serve as a model for identifying HRV39 antigenic sites. Panel A shows the general arrangement of the capsid proteins on HRV2 virus particle. Panel B presents a ribbon diagram of VP1, VP2, VP3, and VP4 with the position of the antibody binding residues. Panel C presents the capsids in a space-filled, ball, model. In Panel C, the residues adjacent to the antibody binding sites have been distinguished to identify amino acids that may contribute to the antigenicity of the epitopes.

Once the amino acid residues participating in epitope are identified in HRV2, they can be used to predict similar residues in other HRV-A strains after aligning the sequences. Amino acid alignments of the capsid regions of all HRV-A and HRV-B serotypes reveal that the sites of the highest degree of variability co-localize with immunodominant epitopes discovered through antibody-binding and antibody-escape studies. FIG. 4 shows a linear representation of portions of the capsid region of the HRV2 and HRV39 polyproteins. FIG. 4 identifies the most highly variable regions and the underlined residues are located within the known epitopes. Residues shown in enlarged and bold typeface indicate the most variable residues within the epitopes. In FIG. 4, the number system starts at the N-terminal residue of the P1 polyprotein. Additional structural and antigenic site analysis of HRV39 was done using HRV A and B homologues (e.g., 16, 14, 2, 2a, 2b, and 3) and has led to the identification of three major immunodominant B cell epitopes in the capsid proteins (Verdaguer, Blaas et al. 2000).

Sites identified for engineering immune refocused mutations are presented in FIG. 4. The minimal epitope residues are indicated by enlarged and bold type and the adjacent amino acids are underlined. The preponderance of charged residues in epitopes is noted. The alignment with HRV2 is used to identify amino acid residues of HRV39 that are likely components of immunodominant epitopes. In FIG. 4, the bold, underlined residues correspond to the surface smoothed amino acids in FIG. 3B and the underlined (but not bold) letters correspond to flanking residues shown as gray balls in FIG. 3C.

Examples of immune refocusing mutations are shown in FIG. 5. Several of the mutations target specific residues in the minimal epitopes as defined by antibody footprints. Thus, M1, M2, M7, M8, M9, and M14 are designed to assess immune dampening at sites thought to be most important in antibody binding in antigenic sites corresponding to HRV2 sites A, B, and C. Additional mutations are presented to assess the additive or multiplicative effects of combining the mutations within epitopes to derive M5, M12, and M16. Because it is possible that mutations to one or more of these sites may not have the most optimum effect of stimulating broadened immunity or may be essential for protein folding and capsid assembly, a second set of mutations are shown that target the flanking residues (dark gray balls in FIG. 3C, mutants, M3, M4, M10, M11, and M15).

Using similar logical strategies, mutations that target additional sites within the HRV-39 capsid molecules or those that target immunodominant sites in other HRV serotypes can be designed.

IRT mutations can be introduced into the capsid gene fragment of HRV39 for the purposes of analyzing cross-neutralizing immune responses using site-directed mutagenesis methods known to the art. The capsid genes can be expressed using a variety of systems known for the expression of recombinant proteins such as bacteria, yeast, mammalian, and insect cell vectors. In the present example, the IRT mutations were introduced into HRV39 capsid genes that were co-expressed with the viral protease protein, 3C, using recombinant baculoviruses. Alternative strategies to produce VLPs of HRV include the use of a single polyprotein containing both the capsid and 3C proteins, separate baculoviruses expressing the capsid and 3C fragments, and other methods known to the art. Further, VLPs of HRV and other rhinoviruses can be stabilized by substituting amino acids that are proximal to the interface between capsid proteins that form capsomers and assemble into virions or virus-like particles. Such amino acid residue can be substituted with cysteine residues to permit disulfide bonds to form between the two proteins and thereby strengthen or stabilize the capsid structure.

Figure 6:
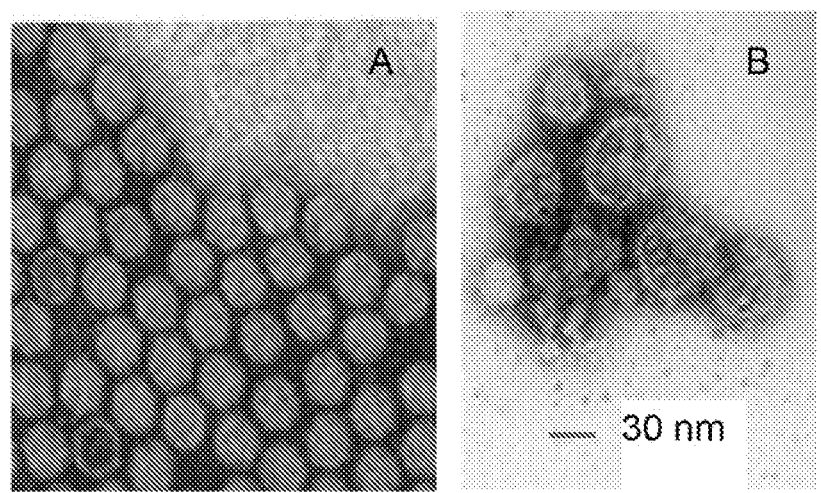
FIG. 6. Transmission electron microscopic analysis of HRV39 virus-like particles expressed in insect larvae using recombinant baculoviruses. Panel A shows native HRV as produced by HeLa cells. Panel B shows HRV39 VLPS. The two micrographs were taken at approximately equal magnification. The micrographs show structures consistent in size and appearance to VLPs.

Insect cells and insect larva were infected with the recombinant baculoviruses for the purpose of producing the IRT antigens as virus-like particles (VLPs). FIG. 6 shows electron micrographs comparing the structure of the HRV39 VLPs (right panel) with the HeLa cell-produced HRV virions (left panel). The VLPs are consistent in size and appearance with empty particles.

Rabbits were immunized with HRV39 IRT VLP antigens. After two boosts, sera were collected for analysis of immune responses.

Virus neutralization assays were performed to assess stimulation of cross-protective immunity conveyed by the IRT antigens. Sixty-one serotypes of HRV were propagated to derive reagent stocks that were standardized to 100-1,000 tissue culture infectious dose-50 (TCID50) of each virus per microliter, for example, depending on the CPE and the replication time of a serotype. FIG. 7 lists the viruses prepared for the cross-neutralization tests. Standard neutralization assays were done to identify serotypes of viruses that were neutralized by sera from IRT antigens as compared to non-immune sera. Briefly, between 100 and 1,000 TCID50 doses of virus were incubated with test sera. In general, higher doses, such as, 1000 TCID50 were used for serotypes that produce visually recognized cytopathic effects within two or three days and lower doses, such as, 100 TCID50, were used for serotypes of HRV that take longer to develop cytopathic effects. To ensure that IRT sera could be distinguished from non-immune rabbit sera on the basis of neutralizing heterologous, final concentrations of IRT sera at 1:8 were compared to 1:2 dilutions of non-immune sera. IRT sera (1:8) were incubated with each heterologous virus at a suitable dose for 1 h and then placed onto MRC-5 cells for 1 h at room temperature using duplicate wells. The monolayers were rinsed with media to remove unattached virus, overlaid with standard growth media, and incubated for 2-4 days at 35° C. The monolayers were observed microscopically until cytopathic effects (CPE) due to virus infection were visible in the negative control wells in which the virus had been incubated with non-immune sera. The intensity of the CPE in each well was scored at least three times over the next 48 hours to assess virus propagation. Scoring was based on a scale of 0 to 10 in which wells showing no, slight, moderate, strong, or complete CPE were assigned a values of 0, 1-2, 3-4, 5-9, or 10, respectively. The scores of the duplicate wells were aggregated as a set and analyzed to determine whether they were statistically higher than the scores assigned to the wells in which the virus had been incubated with non-immune sera instead of sera from rabbits immunized with IRT antigens. The Student's T test was used to determine which HRV serotypes were neutralized better by sera from IRT antigens as compared with non-immune sera. FIG. 8 presents the serotypes that were neutralized by HRV39 IRT sera with a confidence level equal to or greater than 95% for each serum. The column under the heading "39WT"60 lists the HRV serotypes neutralized by serum from rabbits immunized with unmodified (WT) HRV39 antigen. It is important to note that the sera from WT antigen neutralize only the homologous HRV39 antigen and the sera from the IRT antigens neutralize multiple serotypes of HRV. The right-most column presents an aggregate of all tested HRV serotypes that were shown to be neutralized.

Example 2

In addition to separate mutations, immune refocused immunogens may be composed of combinations of mutations at different sites. Thus, immune refocused antigens may contain multiple mutations to epitopes A, B, or C (see FIG. 4) or other antigenic, structural, or functional sites located in other parts of the virus. HRV39 IRT mutants M12, 13, 17, and 18 are examples of antigens containing IRT mutations at multiple epitopes. After engineering the combination sites into the antigen, the second-generation antigens are tested for stimulation of enhanced cross-protective immune responses as described in Example 2.

Example 3

Reverse genetics systems have been developed for HRV and other viruses for the purpose of introducing site-specific mutations into the genomes of the viruses (Lee and Wang, 2003). Immune refocusing mutations can be engineered into recombinant, replication-competent HRV virions. FIG. 9 presents examples of IRT modifications made in the context of the HRV-16 virus sequence. After introduction of the IRT mutations into the proviral plasmid clones, viral RNA transcripts were synthesized from the plasmids using RNA-dependent RNA polymerase and transfected into HeLa cells to derive novel strains of HRV16. The recombinant viruses were propagated in HeLa cells and purified using standard HRV purification methods. Rabbits were immunized with the HRV16 IRT variants and serum samples tested for cross-neutralization of the panel of HRV serotypes shown previously in FIG. 7. Using a similar neutralization assay as in Example 1, sera from rabbits immunized with immune refocused HRV16 virions were compared to non-immune sera to identify heterologous serotypes of virus that could be cross-neutralized by the IRT sera. FIG. 10 lists the viruses that were neutralized by the five HRV16 IRT sera at a confidence level equal to or greater than 95%. The column under the heading "16WT" shows that sera from unmodified HRV16 neutralized homologous virus (HRV16) but did not cross-neutralize heterologous serotypes of HRV. In contrast sera from IRT antigens demonstrated robust cross-neutralization of multiple serotypes of HRV.

Example 4

The above examples demonstrate that the immune refocusing technology is independent of vector or antigen format for stimulated improved cross-reactive immune responses.

IRT antigens of HRV can be incorporated into alternative expression platforms including recombinant viruses such as adenovirus or vaccinia viruses, bacterial or yeast expression systems, and DNA expression molecules.

Example 5

The immune refocusing mutations can be designed rationally using the algorithms described above which include but are not restricted to sequence alignments to identify variable and conserved regions; structural analyses to identify flexible loops, residues associated with functional requirements of the virus, and other features; biochemical analysis of charge, hydrophathy, physical size and other chemical features of amino acids; and the like. Alternatively, IRT mutations can be designed through the use of escape mutations.

In the present example, antibody escape mutations were derived from cultures infected with HRV14. The virus was pre-incubated with varying concentrations of monoclonal or polyclonal antibodies, placed onto cells for 1 h to allow attachment to occur, and washed off. The cells were overlaid with standard culture media and incubated for 1 day at 35° C. to permit replication of viruses that were not neutralized by the antibodies. The process was repeated with increasing concentrations of antibody to derive virus strains that were resistant to the antibody.

FIG. 11 shows an example of virus escape mutants derived using HRV14 and either polyclonal rabbit sera raised against HRV14 virions or monoclonal antibody MoAb17 directed against the NIM-1A epitope. Virus progeny were plaque purified and sequenced to identify amino acids in the virus that survived the antibody pressure. After 3 passages, four plagues were analyzed (Panel A). Two had no mutations in the capsid region, one had a mutation that lead to E94D in residue #94 of VP1, and one had a mutation that led to E90N. After 6 passages, six plagues were analyzed (Panel B). Again, mutations were observed in residues 90 and 94 of VP1. In addition, mutations were observed in residues 120, 124, 125, 126, and 127 of VP2. The result suggests that the antibody contacts the virus at or near these residues. A similar result was observed after 3 passages of virus following incubation with polyclonal rabbit antisera. Panel C shows the sequences in the capsid gene fragment found to contain mutations following pressure with polyclonal antibody. As can be seen, the predominant mutations were in VP2 and the sites overlapped those observed with MoAb #17 shown in Panel B. This result suggests that the polyclonal antibody response contains a low diversity of antibody species and that these species of antibody molecules primarily recognize one or two epitopes.

The results in antibody escape studies can be used to design ITT antigens having the mutations of the escape variants.

Similar studies can be performed using sera from human subjects experimentally infected with FDA-approved stocks of HRV16 and HRV39 or from natural infections.

Example 6

The above examples utilize HRV-A (HRV16 and HRV39) and HRV-B (HRV14) serotypes as examples of immune refocusing of HRV. HRV-C serotypes can also be used as the parental virus for immune refocusing.

HRV-C has been shown to cause disease and exacerbate asthma and chronic lung disease. Efforts to understand the biology and immunology of HRV-C viruses have been complicated by the difficulties encountered in propagating the HRV-C viruses in standard cell lines other than primary human tissue explants.

Fragments and complete genomes of HRV-C viruses have been cloned and nucleic acid and protein sequences determined. Alignments of the HRV-C capsid sequences in the P1 fragment are used to identify regions of variation and conservation. Like HRV-A and HRV-B viruses (and other Class II pathogens such as HIV-1 and influenza), the regions of maximum variation correlate with serotype-specific epitopes. Regions of diversity between the HRV-C viruses are targeted for immune refocusing to design and engineer antigens that stimulate antibodies that neutralize multiple serotypes of HRV-C viruses.

Immune refocusing mutations similar to those provided in the examples above are used. In general, charged amino acids can be substituted by uncharged residues to reduce the strain-restricted antigenicity without destroying structural features such as conformational epitopes. HRV-C viruses of known sequence, such as strain W10-C15, can be used as parental antigens to derive immune refocused antigens.

The resultant immune refocused HRV-C antigens can be used as vaccine components, diagnostic reagents, or to derive novel antibodies.

Example 7

Immune refocused HRV antigens can be used as vectors to deliver heterologous epitopes, or therapeutic or toxic molecules.

The structural models of HRV serotypes can be used to identify flexible loops that can accept the insertion of heterologous epitopes or other molecules. Epitopes from other viruses, such as but not limited to HRV-1 V3 loop peptides, influenza HA epitopes, and the like can be molecularly engineered to be expressed in recombinant virions or VLPs of immune refocused HRV antigens. Using a similar strategy, toxic or therapeutic molecules can be incorporated into the structures for the purpose of providing therapy for cancer or other diseases for which an HRV carrier vector may provide advantages.

The immune refocused HRV VLPs and viruses can also be used to encapsulate small molecules for therapeutic uses. If for example, HRV VLPs can be show to preferentially attach to and enter specific target cells such as cancer cells, the antigens can be used as carrier vectors for delivery of small therapeutic molecules or toxins. The VLP can be readily disrupted in various denaturants known in the art such as but not limited to 5M urea, 6M guanidine-HCL and others. After denaturation, additional small molecules can be added to the solution and the denaturant removed by dialysis or other method. Upon removal of the denaturant, the VLPs and virus particles re-associate into virus-like structures. Because the small molecules were included in the solution, they can be incorporated within the virion or VLP. When the virion or VLP is introduced into a human, it can attach to a cell bearing a virus receptor. Upon entry into the cell, the virus will deliver the payload for therapeutic or toxic uses.

Example 8

The safety, toxicity and potency of recombinant immunogens are evaluated according to the guidelines in 21 CFR 610, which include: (i) general safety test; (ii) stringent safety test in immunocompetent mice; (iii) guinea pig safety test; and (iv) acute and chronic toxicity tests, as described below.

Groups of eight BALB/c mice were inoculated intraperitoneally with 100 µl of immunogen containing 300 µg of the immunogen of interest. Suitable negative and positive controls are used.

The animals are monitored for general health and body weight for 14 days post infection. Similar to animals that receive placebo, animals that receive the immunogen remain health, and do not lose weight or display overt signs of disease during the observation period.

For the more stringent safety test, groups of 15 health BALB/c mice were injected with 300 µg of the immunogen.

One day after inoculation, 3 mice in each group are euthanized and the spleen, lung and liver homogenates are analyzed for immunogen. At week 4, 8, 12, and 16 post infection, 3 mice in each group are euthanized and spleen, liver and lung homogenates are obtained and analyzed to assess presence of the immunogen.

The safety of immunogen is also assessed in the guinea pig model. First, the effect of the immunogen on the general health status of the animals is examined, including weight gain.

Groups of 8 guinea pigs are inoculated intramuscularly with 300 µg of the immunogen.

The general health and body weight of the animals are monitored for six weeks post inoculation. If any animals are euthanized before the six-week period concludes due to serious adverse effects, each euthanized animal will be subjected to a detailed post-mortem examination. All animals are euthanized at the end of six weeks post-inoculation and gross pathology is performed. The immunogen is deemed safe if no adverse health effects are observed and the animals gain weight at the normal rate compared to animals inoculated with placebo as an internal control.

To evaluate the acute and chronic toxicity of an immunogen, groups of 16 guinea pigs are inoculated intradermally with 300 µg of the immunogen at graded doses or saline.

Three days post-inoculation, 3 animals in each group are euthanized to assess the acute effects of the immunogen on the animals. At 28 days post-inoculation, the remaining 8 animals in each group are euthanized to evaluate any chronic effects on the animals. At both time points, the body weight of each animal is obtained. In addition, the gross pathology and appearance of the injection sites are examined. Blood is taken for blood chemistry, and the histopathology of the internal organs and injection sites are performed at each time point.

The mice are given a total of 3 doses of vaccine at 0, 14 and 60 days and the immune response to HRV is measured by ELISA using sera collected from individual mice at 10 day intervals, as described. The neutralization of HRV is measured in the collected sera 80 days after the first vaccination. The results of the study show that the vaccine of interest has the capacity to substantially increase the magnitude and potency of the humoral response to HRV and therefore possesses useful adjuvant properties.

Example 9

Immune refocused antigens can be used as immunogens to raise novel antibodies useful as diagnostics, laboratory reagents, and/or therapeutics. The novel antibodies can be derived as polyclonal antibodies, monoclonal antibodies, or recombinant antibodies derived from immune cells of immunized humans, animals, or in vitro immune systems.

Cross-neutralizing antibodies are rarely observed when an individual has been infected with an HRV serotype or when an animal has been immunized with a naturally-occurring HRV antigen. Because immune refocused antigens contain mutations to serotype-specific epitopes, immunization with immune refocused antigens can enrich the percentage of antibodies or monoclonal antibodies that contain cross-neutralizing activities.

In a similar manner, immune refocused antigens can be used to identify cross-neutralizing antibodies. Immune refocused antigens have mutations in the serotype-restricted epitopes. Antibodies in the population or monoclonal antibodies produced by any method known to the art that are specific to the serotype-restricted epitope that was altered in the immune refocused antigen will not be detected. In the event that the serotype-restricted antibodies are in the majority, the use of immune refocused antigens in the screening steps will improve the efficiency of identifying antibodies that bind the antigen at sites other than those that were altered.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be embraced by the appended claims.

All references cited herein, are incorporated herein by reference in entirety.

The sequences, including the Sequence Listing filed concurrently herewith, herein are incorporated by reference in entirety.

REFERENCES CITED

1. Kohler H, Goudsmit, J, Nara P. Clonal dominance: cause for a limited and failing immune response to HIV-1 infection and vaccination. J. Acquir Immune Defic Syndr. 1992; 5(11):1158-68.
2. Lee, W.-M., and Wang, W. (2003). Human rhinovirus type 16: mutant V1210A requires capsid-binding drug for assembly of pentamers to form virions during morphogenesis. J. Virology. 77, 6235-6244.
3. Kiszka, I., D. Kmieciak, J. Gzyl, T. Naito, E. Bolesta, A. Sieron, S. P. Singh, A. Srinivasan, G. Trinchierei, Y. Kaneko, and D. Kozbor. 2002. Effect of the V3 loop deletion of envelope glycoprotein on cellular responses and protection against challenge with recombinant vaccinia virus expressing gp160 of primary human immunodeficiency virus type I isolates. J Virol 76:4222-32.
4. Adams, P. F., G. E. Hendershot, et al. (1999). "Current estimates from the National Health Interview Survey, 1996." *Vital Health Stat* 10(200): 1-203.
5. Appleyard, G., S. M. Russell, et al. (1990). "Neutralization epitopes of human rhinovirus type 2." *J Gen Virol* 71 (Pt 6): 1275-82.
6. Bertino, J. S. (2002). "Cost burden of viral respiratory infections: issues for formulary decision makers." *Am J Med* 112 Suppl 6A: 42S-49S.
7. Garrity, R. R., G. Rimmelzwaan, et al. (1997). "Refocusing neutralizing antibody response by targeted dampening of an immunodominant epitope." *J Immunol* 159(1): 279-89.
8. Hastings, G. Z., S. A. Speller, et al. (1990). "Neutralizing antibodies to human rhinovirus produced in laboratory animals and humans that recognize a linear sequence from VP2." *J Gen Virol* 71 (Pt 12): 3055-9.
9. Hewat, E. A. and D. Blaas (1996). "Structure of a neutralizing antibody bound bivalently to human rhinovirus 2." *EMBO J* 15(7): 1515-23.
10. Hewat, E. A., T. C. Marlovits, et al. (1998). "Structure of a neutralizing antibody bound monovalently to human rhinovirus 2." *J Virol* 72(5): 4396-402.
11. Mackay, I. M. (2008). "Human rhinoviruses: the cold wars resume." *J Clin Virol* 42(4): 297-320.
12. Paranhos-Baccala, K. Shen, Q. Jin, and J. Wang Emerging Infectious Diseases•www.cedc.gov/eid•Vol. 14, No. 10, October 2008 pgs 1665-1667.
Palmenberg, A. C., D. Spiro, et al. (2009). "Sequencing and Analyses of All Known Human Rhinovirus Genomes Reveals Structure and Evolution." *Science*. 324(5923): 55-9.
14. Turner, R. B. (2001). "The treatment of rhinovirus infections: progress and potential." Antiviral Res 49(1): 1-14.
15. Verdaguer, N., D. Blaas, et al. (2000), "Structure of human rhinovirus serotype 2 (HRV2)." *J Mol Biol* 300(5): 1179-94.
16. Z. Xiang, R. Gonzalez, Z. Xie, Y. Xiao, L. Chen, Y. Li, C. Liu, Y. Hu, Y. Yao, S. Qian, R. Geng, G. Vernet, G. (2008) www.cdc.gov/eid, vol. 14, No. 10 pgs. 1665-1667.
17. Speller et al. (1993) "The nature and spatial distribution of amino acid substitutions conferring resistance to neutralizing monoclonal antibodies in human rhinovirus type 2." J Gen Virol 74(2)193-200.

HRV16 WT (SEQ ID NO: 64)

| | | | | | | | | | | | | | | |
|---|---|---|---|---|---|---|---|---|---|---|---|---|---|---|
|Met|Gly|Ala|Gln|Val|Ser|Arg|Gln|Asn|Val|Gly|Thr|His|Ser|Thr|15
|Gln|Asn|Ser|Val|Ser|Gly|Gly|Ser|Ser|Leu|Asn|Tyr|Phe|Asn|Ile|30
|Asn|Tyr|Phe|Lys|Asp|Ala|Ala|Ser|Ser|Gly|Ala|Ser|Lys|Leu|Glu|45
|Phe|Ser|Gln|Asp|Pro|Ser|Lys|Phe|Thr|Asp|Pro|Val|Lys|Asp|Val|60
|Leu|Glu|Lys|Gly|Ile|Pro|Thr|Leu|Gln|Ser|Pro|Thr|Val|Glu|Ala|75
|Cys|Gly|Tyr|Ser|Asp|Arg|Ile|Ile|Gln|Ile|Thr|Arg|Gly|Asp|Ser|90
|Thr|Ile|Thr|Ser|Gln|Asp|Val|Ala|Asn|Ala|Val|Val|Gly|Tyr|Gly|105
|Val|Trp|Pro|His|Tyr|Leu|Thr|Ala|Asp|Asp|Ala|Ser|Ala|Ile|Asp|120
|Lys|Pro|Thr|Gln|Pro|Asp|Thr|Ser|Ser|Asn|Arg|Phe|Tyr|Thr|Leu|135
|Asp|Ser|Lys|Met|Trp|Asn|Ser|Thr|Ser|Lys|Gly|Trp|Trp|Trp|Lys|150
|Leu|Pro|Asp|Ala|Leu|Lys|Asp|Met|Gly|Ile|Phe|Gly|Glu|Asn|Met|165
|Phe|Tyr|His|Phe|Leu|Gly|Arg|Ser|Gly|Tyr|Thr|Val|His|Val|Gln|180
|Cys|Asn|Ala|Ser|Lys|Phe|His|Gln|Gly|Thr|Leu|Leu|Val|Val|Met|195
|Ile|Pro|Glu|His|Gln|Leu|Ala|Thr|Val|Asn|Lys|Gly|Asn|Val|Asn|210
|Ala|Gly|Tyr|Lys|Lyr|Thr|His|Pro|Gly|Glu|Ala|Gly|Arg|Glu|Val|225
|Gly|Thr|Gln|Val|Glu|Asn|Glu|Lys|Gln|Pro|Ser|Asp|Asp|Asn|Trp|240
|Leu|Asn|Phe|Asp|Gly|Thr|Leu|Leu|Gly|Asn|Leu|Leu|Ile|Phe|Pro|255
|His|Gln|Phe|Ile|Asn|Leu|Arg|Ser|Asn|Asn|Ser|Ala|Thr|Leu|Ile|270
|Val|Pro|Tyr|Val|Asn|Ala|Val|Pro|Met|Asp|Ser|Met|Val|Arg|His|285
|Asn|Asn|Trp|Ser|Leu|Val|Ile|Ile|Pro|Val|Cys|Gln|Leu|Gln|Ser|300
|Asn|Asn|Ile|Ser|Asn|Ile|Val|Pro|Ile|Thr|Val|Ser|Ile|Ser|Pro|315
|Met|Cys|Ala|Glu|Phe|Ser|Gly|Ala|Arg|Ala|Lys|Thr|Val|Val|Gln|330
|Gly|Leu|Pro|Val|Tyr|Val|Thr|Pro|Gly|Ser|Gly|Gln|Phe|Met|Thr|345
|Thr|Asp|Asp|Met|Gln|Ser|Pro|Cys|Ala|Leu|Pro|Trp|Tyr|His|Pro|360
|Thr|Lys|Glu|Ile|Phe|Ile|Pro|Gly|Glu|Val|Lys|Asn|Leu|Ile|Glu|375
|Met|Cys|Gln|Val|Asp|Thr|Leu|Ile|Pro|Ile|Asn|Ser|Thr|Gln|Ser|390
|Asn|Ile|Gly|Asn|Val|Ser|Met|Tyr|Thr|Val|Thr|Leu|Ser|Pro|Gln|405
|Thr|Lys|Leu|Ala|Glu|Glu|Ile|Phe|Ala|Ile|Lys|Val|Asp|Ile|Ala|420
|Ser|His|Pro|Leu|Ala|Thr|Thr|Leu|Ile|Gly|Glu|Ile|Ala|Ser|Tyr|435
|Phe|Thr|His|Trp|Thr|Gly|Ser|Leu|Arg|Phe|Ser|Phe|Met|Phe|Cys|450
|Gly|Thr|Ala|Asn|Thr|Thr|Leu|Lys|Val|Leu|Leu|Ala|Tyr|Thr|Pro|465
|Pro|Gly|Ile|Gly|Lys|Pro|Arg|Ser|Arg|Lys|Glu|Ala|Met|Leu|Gly|480
|Thr|His|Val|Val|Trp|Asp|Val|Gly|Leu|Gln|Ser|Thr|Val|Ser|Leu|495
|Val|Val|Pro|Trp|Ile|Ser|Ala|Ser|Gln|Tyr|Arg|Phe|Thr|Thr|Pro|510
|Asp|Thr|Tyr|Ser|Ser|Ala|Gly|Tyr|Ile|Thr|Cys|Trp|Tyr|Gln|Thr|525
|Asn|Phe|Val|Val|Pro|Pro|Asn|Thr|Pro|Asn|Thr|Ala|Glu|Met|Leu|540
|Cys|Phe|Val|Ser|Gly|Cys|Asn|His|Phe|Cys|Leu|Arg|Met|Ala|Arg|555
|Asp|Thr|Asp|Leu|His|Lys|Gln|Thr|Gly|Pro|Ile|Thr|Gln|Asn|Pro|570
|Val|Glu|Arg|Tyr|Val|Asp|Glu|Val|Leu|Asn|Glu|Val|Leu|Val|Val|585
|Pro|Asn|Ile|Asn|Gln|Ser|His|Pro|Thr|Thr|Ser|Asn|Ala|Ala|Pro|600

-continued

```
Val Leu Asp Ala Ala Glu Thr Gly His Thr Asn Lys Ile Gln Pro    615
Glu Asp Thr Ile Glu Thr Arg Tyr Val Gln Ser Ser Gln Thr Leu    630
Asp Glu Met Ser Val Glu Ser Phe Leu Gly Arg Ser Gly Cys Ile    645
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Arg Thr Asn Leu Thr Thr Val Gly Pro    855
Ser Asp Met Tyr                                                859
HRV16 M1
                                                    (SEQ ID NO: 65)
Met Gly Ala Gln Val Ser Arg Gln Asn Val Gly Thr His Ser Thr     15
Gln Asn Ser Val Ser Gly Gly Ser Ser Leu Asn Tyr Phe Asn Ile     30
Asn Tyr Phe Lys Asp Ala Ala Ser Ser Gly Ala Ser Lys Leu Glu     45
Phe Ser Gln Asp Pro Ser Lys Phe Thr Asp Pro Val Lys Asp Val     60
Leu Glu Lys Gly Ile Pro Thr Leu Gln Ser Pro Thr Val Glu Ala     75
Cys Gly Tyr Ser Asp Arg Ile Ile Gln Ile Thr Arg Gly Asp Ser     90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Asp Ser Lys Met Trp Ala Gly Thr Ser Ala Gly Trp Trp Trp Lys    150
Leu Pro Asp Ala Leu Lys Asp Met Gly Ile Phe Gly Glu Asn Met    165
Phe Tyr His Phe Leu Gly Arg Ser Gly Tyr Thr Val His Val Gln    180
Cys Asn Ala Ser Lys Phe His Gln Gly Thr Leu Leu Val Val Met    195
Ile Pro Glu His Gln Leu Ala Thr Val Asn Lys Gly Asn Val Asn    210
Ala Gly Tyr Lys Lyr Thr His Pro Gly Glu Ala Gly Arg Glu Val    225
Gly Thr Gln Val Glu Asn Glu Lys Gln Pro Ser Asp Asp Asn Trp    240
Leu Asn Phe Asp Gly Thr Leu Leu Gly Asn Leu Leu Ile Phe Pro    255
His Gln Phe Ile Asn Leu Arg Ser Asn Asn Ser Ala Thr Leu Ile    270
Val Pro Tyr Val Asn Ala Val Pro Met Asp Ser Met Val Arg His    285
Asn Asn Trp Ser Leu Val Ile Ile Pro Val Cys Gln Leu Gln Ser    300
Asn Asn Ile Ser Asn Ile Val Pro Ile Thr Val Ser Ile Ser Pro    315
```

-continued

```
Met Cys Ala Glu Phe Ser Gly Ala Arg Ala Lys Thr Val Val Gln    330
Gly Leu Pro Val Tyr Val Thr Pro Gly Ser Gly Gln Phe Met Thr    345
Thr Asp Asp Met Gln Ser Pro Cys Ala Leu Pro Trp Tyr His Pro    360
Thr Lys Glu Ile Phe Ile Pro Gly Glu Val Lys Asn Leu Ile Glu    375
Met Cys Gln Val Asp Thr Leu Ile Pro Ile Asn Ser Thr Gln Ser    390
Asn Ile Gly Asn Val Ser Met Tyr Thr Val Thr Leu Ser Pro Gln    405
Thr Lys Leu Ala Glu Glu Ile Phe Ala Ile Lys Val Asp Ile Ala    420
Ser His Pro Leu Ala Thr Thr Leu Ile Gly Glu Ile Ala Ser Tyr    435
Phe Thr His Trp Thr Gly Ser Leu Arg Phe Ser Phe Met Phe Cys    450
Gly Thr Ala Asn Thr Thr Leu Lys Val Leu Leu Ala Tyr Thr Pro    465
Pro Gly Ile Gly Lys Pro Arg Ser Arg Lys Glu Ala Met Leu Gly    480
Thr His Val Val Trp Asp Val Gly Leu Gln Ser Thr Val Ser Leu    495
Val Val Pro Trp Ile Ser Ala Ser Gln Tyr Arg Phe Thr Thr Pro    510
Asp Thr Tyr Ser Ser Ala Gly Tyr Ile Thr Cys Trp Tyr Gln Thr    525
Asn Phe Val Val Pro Pro Asn Thr Pro Asn Thr Ala Glu Met Leu    540
Cys Phe Val Ser Gly Cys Asn His Phe Cys Leu Arg Met Ala Arg    555
Asp Thr Asp Leu His Lys Gln Thr Gly Pro Ile Thr Gln Asn Pro    570
Val Glu Arg Tyr Val Asp Glu Val Leu Asn Glu Val Leu Val Val    585
Pro Asn Ile Asn Gln Ser His Pro Thr Thr Ser Asn Ala Ala Pro    600
Val Leu Asp Ala Ala Glu Thr Gly His Thr Asn Lys Ile Gln Pro    615
Glu Asp Thr Ile Glu Thr Arg Tyr Val Gln Ser Ser Gln Thr Leu    630
Asp Glu Met Ser Val Glu Ser Phe Leu Gly Arg Ser Gly Cys Ile    645
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Arg Thr Asn Leu Thr Thr Val Gly Pro    855
Ser Asp Met Tyr                                                 859
```

HRV16 M2

(SEQ ID NO: 66)

```
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
```

-continued

```
Phe Ser Gln Asp Pro Ser Lys Phe Thr Asp Pro Val Lys Asp Val         60
Leu Glu Lys Gly Ile Pro Thr Leu Gln Ser Pro Thr Val Glu Ala         75
Cys Gly Tyr Ser Asp Arg Ile Ile Gln Ile Thr Arg Gly Asp Ser         90
Thr Ile Thr Ser Gln Asp Val Ala Asn Ala Val Val Gly Tyr Gly        105
Val Trp Pro His Tyr Leu Thr Ala Asp Asp Ala Ser Ala Ile Asp        120
Lys Pro Thr Gln Pro Asp Thr Ser Ser Asn Arg Phe Tyr Thr Leu        135
Asp Ser Lys Met Trp Asn Ser Thr Ser Lys Gly Trp Trp Trp Lys        150
Leu Pro Asp Ala Leu Lys Asp Met Gly Ile Phe Gly Glu Asn Met        165
Phe Tyr His Phe Leu Gly Arg Ser Gly Tyr Thr Val His Val Gln        180
Cys Asn Ala Ser Lys Phe His Gln Gly Thr Leu Leu Val Val Met        195
Ile Pro Glu His Gln Leu Ala Thr Val Asn Lys Gly Asn Val Asn        210
Ala Gly Tyr Lys Lyr Thr His Pro Gly Glu Ala Gly Ala Gln Val        225
Gly Thr Gln Val Gln Asn Gln Ala Gln Pro Ser Asp Asp Asn Trp        240
Leu Asn Phe Asp Gly Thr Leu Leu Gly Asn Leu Leu Ile Phe Pro        255
His Gln Phe Ile Asn Leu Arg Ser Asn Asn Ser Ala Thr Leu Ile        270
Val Pro Tyr Val Asn Ala Val Pro Met Asp Ser Met Val Arg His        285
Asn Asn Trp Ser Leu Val Ile Ile Pro Val Cys Gln Leu Gln Ser        300
Asn Asn Ile Ser Asn Ile Val Pro Ile Thr Val Ser Ile Ser Pro        315
Met Cys Ala Glu Phe Ser Gly Ala Arg Ala Lys Thr Val Val Gln        330
Gly Leu Pro Val Tyr Val Thr Pro Gly Ser Gly Gln Phe Met Thr        345
Thr Asp Asp Met Gln Ser Pro Cys Ala Leu Pro Trp Tyr His Pro        360
Thr Lys Glu Ile Phe Ile Pro Gly Glu Val Lys Asn Leu Ile Glu        375
Met Cys Gln Val Asp Thr Leu Ile Pro Ile Asn Ser Thr Gln Ser        390
Asn Ile Gly Asn Val Ser Met Tyr Thr Val Thr Leu Ser Pro Gln        405
Thr Lys Leu Ala Glu Glu Ile Phe Ala Ile Lys Val Asp Ile Ala        420
Ser His Pro Leu Ala Thr Thr Leu Ile Gly Glu Ile Ala Ser Tyr        435
Phe Thr His Trp Thr Gly Ser Leu Arg Phe Ser Phe Met Phe Cys        450
Gly Thr Ala Asn Thr Thr Leu Lys Val Leu Leu Ala Tyr Thr Pro        465
Pro Gly Ile Gly Lys Pro Arg Ser Arg Lys Glu Ala Met Leu Gly        480
Thr His Val Val Trp Asp Val Gly Leu Gln Ser Thr Val Ser Leu        495
Val Val Pro Trp Ile Ser Ala Ser Gln Tyr Arg Phe Thr Thr Pro        510
Asp Thr Tyr Ser Ser Ala Gly Tyr Ile Thr Cys Trp Tyr Gln Thr        525
Asn Phe Val Val Pro Pro Asn Thr Pro Asn Thr Ala Glu Met Leu        540
Cys Phe Val Ser Gly Cys Asn His Phe Cys Leu Arg Met Ala Arg        555
Asp Thr Asp Leu His Lys Gln Thr Gly Pro Ile Thr Gln Asn Pro        570
Val Glu Arg Tyr Val Asp Glu Val Leu Asn Glu Val Leu Val Val        585
Pro Asn Ile Asn Gln Ser His Pro Thr Thr Ser Asn Ala Ala Pro        600
Val Leu Asp Ala Ala Glu Thr Gly His Thr Asn Lys Ile Gln Pro        615
Glu Asp Thr Ile Glu Thr Arg Tyr Val Gln Ser Ser Gln Thr Leu        630
Asp Glu Met Ser Val Glu Ser Phe Leu Gly Arg Ser Gly Cys Ile        645
```

-continued

```
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Arg Thr Asn Leu Thr Thr Val Gly Pro    855
Ser Asp Met Tyr                                                859
```

HRV16 M3

(SEQ ID NO: 67)
```
Met Gly Ala Gln Val Ser Arg Gln Asn Val Gly Thr His Ser Thr     15
Gln Asn Ser Val Ser Gly Gly Ser Ser Leu Asn Tyr Phe Asn Ile     30
Asn Tyr Phe Lys Asp Ala Ala Ser Ser Gly Ala Ser Lys Leu Glu     45
Phe Ser Gln Asp Pro Ser Lys Phe Thr Asp Pro Val Lys Asp Val     60
Leu Glu Lys Gly Ile Pro Thr Leu Gln Ser Pro Thr Val Glu Ala     75
Cys Gly Tyr Ser Asp Arg Ile Ile Gln Ile Thr Arg Gly Asp Ser     90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Asp Ser Lys Met Trp Asn Ser Thr Ser Lys Gly Trp Trp Trp Lys    150
Leu Pro Asp Ala Leu Lys Asp Met Gly Ile Phe Gly Glu Asn Met    165
Phe Tyr His Phe Leu Gly Arg Ser Gly Tyr Thr Val His Val Gln    180
Cys Asn Ala Ser Lys Phe His Gln Gly Thr Leu Leu Val Val Met    195
Ile Pro Glu His Gln Leu Ala Thr Val Asn Lys Gly Asn Val Asn    210
Ala Gly Tyr Lys Lyr Thr His Pro Gly Glu Ala Gly Arg Glu Val    225
Gly Thr Gln Val Glu Asn Glu Lys Gln Pro Ser Asp Asp Asn Trp    240
Leu Asn Phe Asp Gly Thr Leu Leu Gly Asn Leu Leu Ile Phe Pro    255
His Gln Phe Ile Asn Leu Arg Ser Asn Asn Ser Ala Thr Leu Ile    270
Val Pro Tyr Val Asn Ala Val Pro Met Asp Ser Met Val Arg His    285
Asn Asn Trp Ser Leu Val Ile Ile Pro Val Cys Gln Leu Ala Ser    300
Asn Ala Ile Ser Ala Ile Val Pro Ile Thr Val Ser Ile Ser Pro    315
Met Cys Ala Glu Phe Ser Gly Ala Arg Ala Lys Thr Val Val Gln    330
Gly Leu Pro Val Tyr Val Thr Pro Gly Ser Gly Gln Phe Met Thr    345
Thr Asp Asp Met Gln Ser Pro Cys Ala Leu Pro Trp Tyr His Pro    360
Thr Lys Glu Ile Phe Ile Pro Gly Glu Val Lys Asn Leu Ile Glu    375
```

```
Met Cys Gln Val Asp Thr Leu Ile Pro Ile Asn Ser Thr Gln Ser    390
Asn Ile Gly Asn Val Ser Met Tyr Thr Val Thr Leu Ser Pro Gln    405
Thr Lys Leu Ala Glu Glu Ile Phe Ala Ile Lys Val Asp Ile Ala    420
Ser His Pro Leu Ala Thr Thr Leu Ile Gly Glu Ile Ala Ser Tyr    435
Phe Thr His Trp Thr Gly Ser Leu Arg Phe Ser Phe Met Phe Cys    450
Gly Thr Ala Asn Thr Thr Leu Lys Val Leu Leu Ala Tyr Thr Pro    465
Pro Gly Ile Gly Lys Pro Arg Ser Arg Lys Glu Ala Met Leu Gly    480
Thr His Val Val Trp Asp Val Gly Leu Gln Ser Thr Val Ser Leu    495
Val Val Pro Trp Ile Ser Ala Ser Gln Tyr Arg Phe Thr Thr Pro    510
Asp Thr Tyr Ser Ser Ala Gly Tyr Ile Thr Cys Trp Tyr Gln Thr    525
Asn Phe Val Val Pro Pro Asn Thr Pro Asn Thr Ala Glu Met Leu    540
Cys Phe Val Ser Gly Cys Asn His Phe Cys Leu Arg Met Ala Arg    555
Asp Thr Asp Leu His Lys Gln Thr Gly Pro Ile Thr Gln Asn Pro    570
Val Glu Arg Tyr Val Asp Glu Val Leu Asn Glu Val Leu Val Val    585
Pro Asn Ile Asn Gln Ser His Pro Thr Thr Ser Asn Ala Ala Pro    600
Val Leu Asp Ala Ala Glu Thr Gly His Thr Asn Lys Ile Gln Pro    615
Glu Asp Thr Ile Glu Thr Arg Tyr Val Gln Ser Ser Gln Thr Leu    630
Asp Glu Met Ser Val Glu Ser Phe Leu Gly Arg Ser Gly Cys Ile    645
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Arg Thr Asn Leu Thr Thr Val Gly Pro    855
Ser Asp Met Tyr                                                859

HRV16 M4
                                                    (SEQ ID NO: 68)
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
Cys Gly Tyr Ser Asp Arg Ile Ile Gln Ile Thr Arg Gly Asp Ser    90
```

-continued

```
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Asp Ser Lys Met Trp Asn Ser Thr Ser Lys Gly Trp Trp Trp Lys    150
Leu Pro Asp Ala Leu Lys Asp Met Gly Ile Phe Gly Glu Asn Met    165
Phe Tyr His Phe Leu Gly Arg Ser Gly Tyr Thr Val His Val Gln    180
Cys Asn Ala Ser Lys Phe His Gln Gly Thr Leu Leu Val Val Met    195
Ile Pro Glu His Gln Leu Ala Thr Val Asn Lys Gly Asn Val Asn    210
Ala Gly Tyr Lys Lyr Thr His Pro Gly Glu Ala Gly Arg Glu Val    225
Gly Thr Gln Val Glu Asn Glu Lys Gln Pro Ser Asp Asp Asn Trp    240
Leu Asn Phe Asp Gly Thr Leu Leu Gly Asn Leu Leu Ile Phe Pro    255
His Gln Phe Ile Asn Leu Arg Ser Asn Asn Ser Ala Thr Leu Ile    270
Val Pro Tyr Val Asn Ala Val Pro Met Asp Ser Met Val Arg His    285
Asn Asn Trp Ser Leu Val Ile Ile Pro Val Cys Gln Leu Gln Ser    300
Asn Asn Ile Ser Asn Ile Val Pro Ile Thr Val Ser Ile Ser Pro    315
Met Cys Ala Glu Phe Ser Gly Ala Val Ala Leu Thr Val Val Gln    330
Gly Leu Pro Val Tyr Val Thr Pro Gly Ser Gly Gln Phe Met Thr    345
Thr Asp Asp Met Gln Ser Pro Cys Ala Leu Pro Trp Tyr His Pro    360
Thr Lys Glu Ile Phe Ile Pro Gly Glu Val Lys Asn Leu Ile Glu    375
Met Cys Gln Val Asp Thr Leu Ile Pro Ile Asn Ser Thr Gln Ser    390
Asn Ile Gly Asn Val Ser Met Tyr Thr Val Thr Leu Ser Pro Gln    405
Thr Lys Leu Ala Glu Glu Ile Phe Ala Ile Lys Val Asp Ile Ala    420
Ser His Pro Leu Ala Thr Thr Leu Ile Gly Glu Ile Ala Ser Tyr    435
Phe Thr His Trp Thr Gly Ser Leu Arg Phe Ser Phe Met Phe Cys    450
Gly Thr Ala Asn Thr Thr Leu Lys Val Leu Leu Ala Tyr Thr Pro    465
Pro Gly Ile Gly Lys Pro Arg Ser Arg Lys Glu Ala Met Leu Gly    480
Thr His Val Val Trp Asp Val Gly Leu Gln Ser Thr Val Ser Leu    495
Val Val Pro Trp Ile Ser Ala Ser Gln Tyr Arg Phe Thr Thr Pro    510
Asp Thr Tyr Ser Ser Ala Gly Tyr Ile Thr Cys Trp Tyr Gln Thr    525
Asn Phe Val Val Pro Pro Asn Thr Pro Asn Thr Ala Glu Met Leu    540
Cys Phe Val Ser Gly Cys Asn His Phe Cys Leu Arg Met Ala Arg    555
Asp Thr Asp Leu His Lys Gln Thr Gly Pro Ile Thr Gln Asn Pro    570
Val Glu Arg Tyr Val Asp Glu Val Leu Asn Glu Val Leu Val Val    585
Pro Asn Ile Asn Gln Ser His Pro Thr Thr Ser Asn Ala Ala Pro    600
Val Leu Asp Ala Ala Glu Thr Gly His Thr Asn Lys Ile Gln Pro    615
Glu Asp Thr Ile Glu Thr Arg Tyr Val Gln Ser Ser Gln Thr Leu    630
Asp Glu Met Ser Val Glu Ser Phe Leu Gly Arg Ser Gly Cys Ile    645
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
```

-continued

```
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Arg Thr Asn Leu Thr Thr Val Gly Pro    855
Ser Asp Met Tyr                                                 859
```

HRV16 M5
(SEQ ID NO: 69)

```
Met Gly Ala Gln Val Ser Arg Gln Asn Val Gly Thr His Ser Thr    15
Gln Asn Met Val Ser Asn Gly Ser Ser Leu Asn Tyr Phe Asn Ile    30
Asn Tyr Phe Lys Asp Ala Ala Ser Ser Gly Ala Ser Arg Leu Asp    45
Phe Ser Gln Asp Pro Ser Lys Phe Thr Asp Pro Val Lys Asp Val    60
Leu Glu Lys Gly Ile Pro Thr Leu Gln Ser Pro Ser Val Glu Ala    75
Cys Gly Tyr Ser Asp Arg Ile Ile Gln Ile Thr Arg Gly Asp Ser    90
Thr Ile Thr Ser Gln Asp Val Ala Asn Ala Val Val Gly Tyr Gly    105
Val Trp Pro His Tyr Leu Thr Pro Gln Asp Ala Thr Ala Ile Asp    120
Lys Pro Thr Gln Pro Asp Thr Ser Ser Asn Arg Phe Tyr Thr Leu    135
Asp Ser Lys Met Trp Asn Ser Thr Ser Lys Gly Trp Trp Trp Lys    150
Leu Pro Asp Ala Leu Lys Asp Met Gly Ile Phe Gly Glu Asn Met    165
Phe Tyr His Phe Leu Gly Arg Ser Gly Tyr Thr Val His Val Gln    180
Cys Asn Ala Ser Lys Phe His Gln Gly Thr Leu Leu Val Val Met    195
Ile Pro Glu His Gln Leu Ala Thr Val Asn Lys Gly Asn Val Asn    210
Ala Gly Tyr Lys Tyr Thr His Pro Gly Glu Ala Gly Arg Glu Val    225
Gly Thr Gln Val Glu Asn Glu Lys Gln Pro Ser Asp Asp Asn Trp    240
Leu Asn Phe Asp Gly Thr Leu Leu Gly Asn Leu Leu Ile Phe Pro    255
His Gln Phe Ile Asn Leu Arg Ser Asn Asn Ser Ala Thr Leu Ile    270
Val Pro Tyr Val Asn Ala Val Pro Met Asp Ser Met Val Arg His    285
Asn Asn Trp Ser Leu Val Ile Ile Pro Val Cys Gln Leu Gln Ser    300
Asn Asn Ile Ser Asn Ile Val Pro Ile Thr Val Ser Ile Ser Pro    315
Met Cys Ala Glu Phe Ser Gly Ala Arg Ala Lys Thr Val Val Gln    330
Gly Leu Pro Val Tyr Val Thr Pro Gly Ser Gly Gln Phe Met Thr    345
Thr Asp Asp Met Gln Ser Pro Cys Ala Leu Pro Trp Tyr His Pro    360
Thr Lys Glu Ile Phe Ile Pro Gly Glu Val Lys Asn Leu Ile Glu    375
Met Cys Gln Val Asp Thr Leu Ile Pro Ile Asn Ser Thr Gln Ser    390
Asn Ile Gly Asn Val Ser Met Tyr Thr Val Thr Leu Ser Pro Gln    405
Thr Lys Leu Ala Glu Glu Ile Phe Ala Ile Lys Val Asp Ile Ala    420
```

-continued

```
Ser His Pro Leu Ala Thr Thr Leu Ile Gly Glu Ile Ala Ser Tyr    435
Phe Thr His Trp Thr Gly Ser Leu Arg Phe Ser Phe Met Phe Cys    450
Gly Thr Ala Asn Thr Thr Leu Lys Val Leu Leu Ala Tyr Thr Pro    465
Pro Gly Ile Gly Lys Pro Arg Ser Arg Lys Glu Ala Met Leu Gly    480
Thr His Val Val Trp Asp Val Gly Leu Gln Ser Thr Val Ser Leu    495
Val Val Pro Trp Ile Ser Ala Ser Gln Tyr Arg Phe Thr Thr Pro    510
Asp Thr Tyr Ser Ser Ala Gly Tyr Ile Thr Cys Trp Tyr Gln Thr    525
Asn Phe Val Val Pro Pro Asn Thr Pro Asn Thr Ala Glu Met Leu    540
Cys Phe Val Ser Gly Cys Asn His Phe Cys Leu Arg Met Ala Arg    555
Asp Thr Asp Leu His Lys Gln Thr Gly Pro Ile Thr Gln Asn Pro    570
Val Glu Arg Tyr Val Asp Glu Val Leu Asn Glu Val Leu Val Val    585
Pro Asn Ile Asn Gln Ser His Pro Thr Thr Ser Asn Ala Ala Pro    600
Val Leu Asp Ala Ala Glu Thr Gly His Thr Asn Lys Ile Gln Pro    615
Glu Asp Thr Ile Glu Thr Arg Tyr Val Gln Ser Ser Gln Thr Leu    630
Asp Glu Met Ser Val Glu Ser Phe Leu Gly Arg Ser Gly Cys Ile    645
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Arg Thr Asn Leu Thr Thr Val Gly Pro    855
Ser Asp Met Tyr                                                859

HRV16 M6
                                                  (SEQ ID NO: 70)
Met Gly Ala Gln Val Ser Arg Gln Asn Val Gly Thr His Ser Thr     15
Gln Asn Met Val Ser Asn Gly Ser Ser Leu Asn Tyr Phe Asn Ile     30
Asn Tyr Phe Lys Asp Ala Ala Ser Ser Gly Ala Ser Arg Leu Asp     45
Phe Ser Gln Asp Pro Ser Lys Phe Thr Asp Pro Val Lys Asp Val     60
Leu Glu Lys Gly Ile Pro Thr Leu Gln Ser Pro Ser Val Glu Ala     75
Cys Gly Tyr Ser Asp Arg Ile Ile Gln Ile Thr Arg Gly Asp Ser     90
Thr Ile Thr Ser Gln Asp Val Ala Asn Ala Val Val Gly Tyr Gly    105
Val Trp Pro His Tyr Leu Thr Pro Gln Asp Ala Thr Ala Ile Asp    120
Lys Pro Thr Gln Pro Asp Thr Ser Ser Asn Arg Phe Tyr Thr Leu    135
Asp Ser Lys Met Trp Asn Ser Thr Ser Lys Gly Trp Trp Trp Lys    150
```

-continued

```
Leu Pro Asp Ala Leu Lys Asp Met Gly Ile Phe Gly Glu Asn Met     165
Phe Tyr His Phe Leu Gly Arg Ser Gly Tyr Thr Val His Val Gln     180
Cys Asn Ala Ser Lys Phe His Gln Gly Thr Leu Leu Val Val Met     195
Ile Pro Glu His Gln Leu Ala Thr Val Asn Lys Gly Asn Val Asn     210
Ala Gly Tyr Lys Tyr Thr His Pro Gly Glu Ala Gly Arg Glu Val     225
Gly Thr Gln Val Glu Asn Glu Lys Gln Pro Ser Asp Asp Asn Trp     240
Leu Asn Phe Asp Gly Thr Leu Leu Gly Asn Leu Leu Ile Phe Pro     255
His Gln Phe Ile Asn Leu Arg Ser Asn Asn Ser Ala Thr Leu Ile     270
Val Pro Tyr Val Asn Ala Val Pro Met Asp Ser Met Val Arg His     285
Asn Asn Trp Ser Leu Val Ile Ile Pro Val Cys Gln Leu Gln Ser     300
Asn Asn Ile Ser Asn Ile Val Pro Ile Thr Val Ser Ile Ser Pro     315
Met Cys Ala Glu Phe Ser Gly Ala Arg Ala Lys Thr Val Val Gln     330
Gly Leu Pro Val Tyr Val Thr Pro Gly Ser Gly Gln Phe Met Thr     345
Thr Asp Asp Met Gln Ser Pro Cys Ala Leu Pro Trp Tyr His Pro     360
Thr Lys Glu Ile Phe Ile Pro Gly Glu Val Lys Asn Leu Ile Glu     375
Met Cys Gln Val Asp Thr Leu Ile Pro Ile Asn Ser Thr Gln Ser     390
Asn Ile Gly Asn Val Ser Met Tyr Thr Val Thr Leu Ser Pro Gln     405
Thr Lys Leu Ala Glu Glu Ile Phe Ala Ile Lys Val Asp Ile Ala     420
Ser His Pro Leu Ala Thr Thr Leu Ile Gly Glu Ile Ala Ser Tyr     435
Phe Thr His Trp Thr Gly Ser Leu Arg Phe Ser Phe Met Phe Cys     450
Gly Thr Ala Asn Thr Thr Leu Lys Val Leu Leu Ala Tyr Thr Pro     465
Pro Gly Ile Gly Lys Pro Arg Ser Arg Lys Glu Ala Met Leu Gly     480
Thr His Val Val Trp Asp Val Gly Leu Gln Ser Thr Val Ser Leu     495
Val Val Pro Trp Ile Ser Ala Ser Gln Tyr Arg Phe Thr Thr Pro     510
Asp Thr Tyr Ser Ser Ala Gly Tyr Ile Thr Cys Trp Tyr Gln Thr     525
Asn Phe Val Val Pro Pro Asn Thr Pro Asn Thr Ala Glu Met Leu     540
Cys Phe Val Ser Gly Cys Asn His Phe Cys Leu Arg Met Ala Arg     555
Asp Thr Asp Leu His Lys Gln Thr Gly Pro Ile Thr Gln Asn Pro     570
Val Glu Arg Tyr Val Asp Glu Val Leu Asn Glu Val Leu Val Val     585
Pro Asn Ile Asn Gln Ser His Pro Thr Thr Ser Asn Ala Ala Pro     600
Val Leu Asp Ala Ala Glu Thr Gly His Thr Asn Lys Ile Gln Pro     615
Glu Asp Thr Ile Glu Thr Arg Tyr Val Gln Ser Ser Gln Thr Leu     630
Asp Glu Met Ser Val Glu Ser Phe Leu Gly Arg Ser Gly Cys Ile     645
His Glu Ser Val Leu Asp Ile Val Asp Asn Tyr Asn Asp Gln Ser     660
Phe Thr Lys Trp Asn Ile Asn Leu Gln Glu Met Ala Gln Ile Arg     675
Arg Lys Phe Glu Met Phe Thr Tyr Ala Arg Phe Asp Ser Glu Ile     690
Thr Met Val Pro Ser Val Ala Ala Lys Asp Gly His Ile Gly His     705
Ile Val Met Gln Tyr Met Tyr Val Pro Pro Gly Ala Pro Ile Pro     720
Thr Thr Arg Asp Asp Tyr Ala Trp Gln Ser Gly Thr Asn Ala Ser     735
Val Phe Trp Gln His Gly Gln Pro Phe Pro Arg Phe Ser Leu Pro     750
```

-continued

```
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Arg Thr Asn Leu Thr Thr Val Gly Pro    855
Ser Asp Met Tyr                                                 859
```

HRV16 M7
(SEQ ID NO: 71)
```
Met Gly Ala Gln Val Ser Arg Gln Asn Val Gly Thr His Ser Thr     15
Gln Asn Met Val Ser Asn Gly Ser Ser Leu Asn Tyr Phe Asn Ile     30
Asn Tyr Phe Lys Asp Ala Ala Ser Ser Gly Ala Ser Arg Leu Asp     45
Phe Ser Gln Asp Pro Ser Lys Phe Thr Asp Pro Val Lys Asp Val     60
Leu Glu Lys Gly Ile Pro Thr Leu Gln Ser Pro Ser Val Glu Ala     75
Cys Gly Tyr Ser Asp Arg Ile Ile Gln Ile Thr Arg Gly Asp Ser     90
Thr Ile Thr Ser Gln Asp Val Ala Asn Ala Val Val Gly Tyr Gly    105
Val Trp Pro His Tyr Leu Thr Pro Gln Asp Ala Thr Ala Ile Asp    120
Lys Pro Thr Gln Pro Asp Thr Ser Ser Asn Arg Phe Tyr Thr Leu    135
Asp Ser Lys Met Trp Asn Ser Thr Ser Lys Gly Trp Trp Trp Lys    150
Leu Pro Asp Ala Leu Lys Asp Met Gly Ile Phe Gly Glu Asn Met    165
Phe Tyr His Phe Leu Gly Arg Ser Gly Tyr Thr Val His Val Gln    180
Cys Asn Ala Ser Lys Phe His Gln Gly Thr Leu Leu Val Val Met    195
Ile Pro Glu His Gln Leu Ala Thr Val Asn Lys Gly Asn Val Asn    210
Ala Gly Tyr Lys Tyr Thr His Pro Gly Glu Ala Gly Arg Glu Val    225
Gly Thr Gln Val Glu Asn Glu Lys Gln Pro Ser Asp Asp Asn Trp    240
Leu Asn Phe Asp Gly Thr Leu Leu Gly Asn Leu Leu Ile Phe Pro    255
His Gln Phe Ile Asn Leu Arg Ser Asn Asn Ser Ala Thr Leu Ile    270
Val Pro Tyr Val Asn Ala Val Pro Met Asp Ser Met Val Arg His    285
Asn Asn Trp Ser Leu Val Ile Ile Pro Val Cys Gln Leu Gln Ser    300
Asn Asn Ile Ser Asn Ile Val Pro Ile Thr Val Ser Ile Ser Pro    315
Met Cys Ala Glu Phe Ser Gly Ala Arg Ala Lys Thr Val Val Gln    330
Gly Leu Pro Val Tyr Val Thr Pro Gly Ser Gly Gln Phe Met Thr    345
Thr Asp Asp Met Gln Ser Pro Cys Ala Leu Pro Trp Tyr His Pro    360
Thr Lys Glu Ile Phe Ile Pro Gly Glu Val Lys Asn Leu Ile Glu    375
Met Cys Gln Val Asp Thr Leu Ile Pro Ile Asn Ser Thr Gln Ser    390
Asn Ile Gly Asn Val Ser Met Tyr Thr Val Thr Leu Ser Pro Gln    405
Thr Lys Leu Ala Glu Glu Ile Phe Ala Ile Lys Val Asp Ile Ala    420
Ser His Pro Leu Ala Thr Thr Leu Ile Gly Glu Ile Ala Ser Tyr    435
Phe Thr His Trp Thr Gly Ser Leu Arg Phe Ser Phe Met Phe Cys    450
Gly Thr Ala Asn Thr Thr Leu Lys Val Leu Leu Ala Tyr Thr Pro    465
Pro Gly Ile Gly Lys Pro Arg Ser Arg Lys Glu Ala Met Leu Gly    480
```

```
Thr His Val Val Trp Asp Val Gly Leu Gln Ser Thr Val Ser Leu      495
Val Val Pro Trp Ile Ser Ala Ser Gln Tyr Arg Phe Thr Thr Pro      510
Asp Thr Tyr Ser Ser Ala Gly Tyr Ile Thr Cys Trp Tyr Gln Thr      525
Asn Phe Val Val Pro Pro Asn Thr Pro Asn Thr Ala Glu Met Leu      540
Cys Phe Val Ser Gly Cys Asn His Phe Cys Leu Arg Met Ala Arg      555
Asp Thr Asp Leu His Lys Gln Thr Gly Pro Ile Thr Gln Asn Pro      570
Val Glu Arg Tyr Val Asp Glu Val Leu Asn Glu Val Leu Val Val      585
Pro Asn Ile Asn Gln Ser His Pro Thr Thr Ser Asn Ala Ala Pro      600
Val Leu Asp Ala Ala Glu Thr Gly His Thr Asn Lys Ile Gln Pro      615
Glu Asp Thr Ile Glu Thr Arg Tyr Val Gln Ser Ser Gln Thr Leu      630
Asp Glu Met Ser Val Glu Ser Phe Leu Gly Arg Ser Gly Cys Ile      645
His Glu Ser Val Leu Asp Ile Val Asp Asn Tyr Asn Asp Gln Ser      660
Phe Thr Lys Trp Asn Ile Asn Leu Gln Glu Met Ala Gln Ile Arg      675
Arg Lys Phe Glu Met Phe Thr Tyr Ala Arg Phe Asp Ser Glu Ile      690
Thr Met Val Pro Ser Val Ala Ala Lys Asp Gly His Ile Gly His      705
Ile Val Met Gln Tyr Met Tyr Val Pro Pro Gly Ala Pro Ile Pro      720
Thr Thr Arg Asp Asp Tyr Ala Trp Gln Ser Gly Thr Asn Ala Ser      735
Val Phe Trp Gln His Gly Gln Pro Phe Pro Arg Phe Ser Leu Pro      750
Phe Leu Ser Ile Ala Ser Ala Tyr Tyr Met Phe Tyr Asp Gly Tyr      765
Asp Gly Asp Thr Tyr Lys Ser Arg Tyr Gly Thr Val Val Thr Asn      780
Asp Met Gly Thr Leu Cys Ser Arg Ile Val Thr Ala Gly Ala Leu      795
His Ala Val Ala Val Val Thr Arg Ile Tyr His Lys Ala Lys His      810
Thr Lys Ala Trp Cys Pro Arg Pro Pro Arg Ala Val Gln Tyr Ser      825
His Thr His Thr Thr Asn Tyr Lys Leu Ser Ser Glu Val His Asn      840
Asp Val Ala Ile Arg Pro Arg Thr Asn Leu Thr Thr Val Gly Pro      855
Ser Asp Met Tyr                                                  859
HRV16 M8
                                                   (SEQ ID NO: 72)
Met Gly Ala Gln Val Ser Arg Gln Asn Val Gly Thr His Ser Thr       15
Gln Asn Met Val Ser Asn Gly Ser Ser Leu Asn Tyr Phe Asn Ile       30
Asn Tyr Phe Lys Asp Ala Ala Ser Ser Gly Ala Ser Arg Leu Asp       45
Phe Ser Gln Asp Pro Ser Lys Phe Thr Asp Pro Val Lys Asp Val       60
Leu Glu Lys Gly Ile Pro Thr Leu Gln Ser Pro Ser Val Glu Ala       75
Cys Gly Tyr Ser Asp Arg Ile Ile Gln Ile Thr Arg Gly Asp Ser       90
Thr Ile Thr Ser Gln Asp Val Ala Asn Ala Val Val Gly Tyr Gly      105
Val Trp Pro His Tyr Leu Thr Pro Gln Asp Ala Thr Ala Ile Asp      120
Lys Pro Thr Gln Pro Asp Thr Ser Ser Asn Arg Phe Tyr Thr Leu      135
Asp Ser Lys Met Trp Asn Ser Thr Ser Lys Gly Trp Trp Trp Lys      150
Leu Pro Asp Ala Leu Lys Asp Met Gly Ile Phe Gly Glu Asn Met      165
Phe Tyr His Phe Leu Gly Arg Ser Gly Tyr Thr Val His Val Gln      180
Cys Asn Ala Ser Lys Phe His Gln Gly Thr Leu Leu Val Val Met      195
```

-continued

```
Ile Pro Glu His Gln Leu Ala Thr Val Asn Lys Gly Asn Val Asn    210
Ala Gly Tyr Lys Tyr Thr His Pro Gly Glu Ala Gly Arg Glu Val    225
Gly Thr Gln Val Glu Asn Glu Lys Gln Pro Ser Asp Asp Asn Trp    240
Leu Asn Phe Asp Gly Thr Leu Leu Gly Asn Leu Leu Ile Phe Pro    255
His Gln Phe Ile Asn Leu Arg Ser Asn Asn Ser Ala Thr Leu Ile    270
Val Pro Tyr Val Asn Ala Val Pro Met Asp Ser Met Val Arg His    285
Asn Asn Trp Ser Leu Val Ile Ile Pro Val Cys Gln Leu Gln Ser    300
Asn Asn Ile Ser Asn Ile Val Pro Ile Thr Val Ser Ile Ser Pro    315
Met Cys Ala Glu Phe Ser Gly Ala Arg Ala Lys Thr Val Val Gln    330
Gly Leu Pro Val Tyr Val Thr Pro Gly Ser Gly Gln Phe Met Thr    345
Thr Asp Asp Met Gln Ser Pro Cys Ala Leu Pro Trp Tyr His Pro    360
Thr Lys Glu Ile Phe Ile Pro Gly Glu Val Lys Asn Leu Ile Glu    375
Met Cys Gln Val Asp Thr Leu Ile Pro Ile Asn Ser Thr Gln Ser    390
Asn Ile Gly Asn Val Ser Met Tyr Thr Val Thr Leu Ser Pro Gln    405
Thr Lys Leu Ala Glu Glu Ile Phe Ala Ile Lys Val Asp Ile Ala    420
Ser His Pro Leu Ala Thr Thr Leu Ile Gly Glu Ile Ala Ser Tyr    435
Phe Thr His Trp Thr Gly Ser Leu Arg Phe Ser Phe Met Phe Cys    450
Gly Thr Ala Asn Thr Thr Leu Lys Val Leu Leu Ala Tyr Thr Pro    465
Pro Gly Ile Gly Lys Pro Arg Ser Arg Lys Glu Ala Met Leu Gly    480
Thr His Val Val Trp Asp Val Gly Leu Gln Ser Thr Val Ser Leu    495
Val Val Pro Trp Ile Ser Ala Ser Gln Tyr Arg Phe Thr Thr Pro    510
Asp Thr Tyr Ser Ser Ala Gly Tyr Ile Thr Cys Trp Tyr Gln Thr    525
Asn Phe Val Val Pro Pro Asn Thr Pro Asn Thr Ala Glu Met Leu    540
Cys Phe Val Ser Gly Cys Asn His Phe Cys Leu Arg Met Ala Arg    555
Asp Thr Asp Leu His Lys Gln Thr Gly Pro Ile Thr Gln Asn Pro    570
Val Glu Arg Tyr Val Asp Glu Val Leu Asn Glu Val Leu Val Val    585
Pro Asn Ile Asn Gln Ser His Pro Thr Thr Ser Asn Ala Ala Pro    600
Val Leu Asp Ala Ala Glu Thr Gly His Thr Asn Lys Ile Gln Pro    615
Glu Asp Thr Ile Glu Thr Arg Tyr Val Gln Ser Ser Gln Thr Leu    630
Asp Glu Met Ser Val Glu Ser Phe Leu Gly Arg Ser Gly Cys Ile    645
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
```

-continued

```
Thr Lys Ala Trp Cys Pro Arg Pro Arg Ala Val Gln Tyr Ser    825
His Thr His Thr Thr Asn Tyr Ala Leu Ser val Gln Val His Asn 840
Asp Val Ala Ile Arg Pro Arg Thr Asn Leu Thr Thr Val Gly Pro 855
Ser Asp Met Tyr                                             859
```

HRV16 M9

(SEQ ID NO: 73)
```
Met Gly Ala Gln Val Ser Arg Gln Asn Val Gly Thr His Ser Thr  15
Gln Asn Met Val Ser Asn Gly Ser Ser Leu Asn Tyr Phe Asn Ile  30
Asn Tyr Phe Lys Asp Ala Ala Ser Ser Gly Ala Ser Arg Leu Asp  45
Phe Ser Gln Asp Pro Ser Lys Phe Thr Asp Pro Val Lys Asp Val  60
Leu Glu Lys Gly Ile Pro Thr Leu Gln Ser Pro Ser Val Glu Ala  75
Cys Gly Tyr Ser Asp Arg Ile Ile Gln Ile Thr Arg Gly Asp Ser  90
Thr Ile Thr Ser Gln Asp Val Ala Asn Ala Val Val Gly Tyr Gly 105
Val Trp Pro His Tyr Leu Thr Pro Gln Asp Ala Thr Ala Ile Asp 120
Lys Pro Thr Gln Pro Asp Thr Ser Ser Asn Arg Phe Tyr Thr Leu 135
Asp Ser Lys Met Trp Asn Ser Thr Ser Lys Gly Trp Trp Trp Lys 150
Leu Pro Asp Ala Leu Lys Asp Met Gly Ile Phe Gly Glu Asn Met 165
Phe Tyr His Phe Leu Gly Arg Ser Gly Tyr Thr Val His Val Gln 180
Cys Asn Ala Ser Lys Phe His Gln Gly Thr Leu Leu Val Val Met 195
Ile Pro Glu His Gln Leu Ala Thr Val Asn Lys Gly Asn Val Asn 210
Ala Gly Tyr Lys Tyr Thr His Pro Gly Glu Ala Gly Arg Glu Val 225
Gly Thr Gln Val Glu Asn Glu Lys Gln Pro Ser Asp Asp Asn Trp 240
Leu Asn Phe Asp Gly Thr Leu Leu Gly Asn Leu Leu Ile Phe Pro 255
His Gln Phe Ile Asn Leu Arg Ser Asn Asn Ser Ala Thr Leu Ile 270
Val Pro Tyr Val Asn Ala Val Pro Met Asp Ser Met Val Arg His 285
Asn Asn Trp Ser Leu Val Ile Ile Pro Val Cys Gln Leu Gln Ser 300
Asn Asn Ile Ser Asn Ile Val Pro Ile Thr Val Ser Ile Ser Pro 315
Met Cys Ala Glu Phe Ser Gly Ala Arg Ala Lys Thr Val Val Gln 330
Gly Leu Pro Val Tyr Val Thr Pro Gly Ser Gly Gln Phe Met Thr 345
Thr Asp Asp Met Gln Ser Pro Cys Ala Leu Pro Trp Tyr His Pro 360
Thr Lys Glu Ile Phe Ile Pro Gly Glu Val Lys Asn Leu Ile Glu 375
Met Cys Gln Val Asp Thr Leu Ile Pro Ile Asn Ser Thr Gln Ser 390
Asn Ile Gly Asn Val Ser Met Tyr Thr Val Thr Leu Ser Pro Gln 405
Thr Lys Leu Ala Glu Glu Ile Phe Ala Ile Lys Val Asp Ile Ala 420
Ser His Pro Leu Ala Thr Thr Leu Ile Gly Glu Ile Ala Ser Tyr 435
Phe Thr His Trp Thr Gly Ser Leu Arg Phe Ser Phe Met Phe Cys 450
Gly Thr Ala Asn Thr Thr Leu Lys Val Leu Leu Ala Tyr Thr Pro 465
Pro Gly Ile Gly Lys Pro Arg Ser Arg Lys Glu Ala Met Leu Gly 480
Thr His Val Val Trp Asp Val Gly Leu Gln Ser Thr Val Ser Leu 495
Val Val Pro Trp Ile Ser Ala Ser Gln Tyr Arg Phe Thr Thr Pro 510
Asp Thr Tyr Ser Ser Ala Gly Tyr Ile Thr Cys Trp Tyr Gln Thr 525
```

-continued

```
Asn Phe Val Val Pro Pro Asn Thr Pro Asn Thr Ala Glu Met Leu    540
Cys Phe Val Ser Gly Cys Asn His Phe Cys Leu Arg Met Ala Arg    555
Asp Thr Asp Leu His Lys Gln Thr Gly Pro Ile Thr Gln Asn Pro    570
Val Glu Arg Tyr Val Asp Glu Val Leu Asn Glu Val Leu Val Val    585
Pro Asn Ile Asn Gln Ser His Pro Thr Thr Ser Asn Ala Ala Pro    600
Val Leu Asp Ala Ala Glu Thr Gly His Thr Asn Lys Ile Gln Pro    615
Glu Asp Thr Ile Glu Thr Arg Tyr Val Gln Ser Ser Gln Thr Leu    630
Asp Glu Met Ser Val Glu Ser Phe Leu Gly Arg Ser Gly Cys Ile    645
His Glu Ser Val Leu Asp Ile Val Asp Asn Tyr Asn Asp Gln Ser    660
Phe Thr Lys Trp Asn Ile Asn Leu Gln Glu Met Ala Gln Ile Arg    675
Arg Lys Phe Glu Met Phe Thr Tyr Ala Arg Phe Asp Ser Glu Ile    690
Thr Met Val Pro Ser Val Ala Ala Lys Asp Gly His Ile Gly His    705
Ile Val Met Gln Tyr Met Tyr Val Pro Pro Gly Ala Pro Ile Pro    720
Thr Thr Arg Asp Asp Tyr Ala Trp Gln Ser Gly Thr Asn Ala Ser    735
Val Phe Trp Gln His Gly Gln Pro Phe Pro Arg Phe Ser Leu Pro    750
Phe Leu Ser Ile Ala Ser Ala Tyr Tyr Met Phe Tyr Asp Gly Tyr    765
Asp Gly Asp Thr Tyr Lys Ser Arg Tyr Gly Thr Val Val Thr Asn    780
Asp Met Gly Thr Leu Cys Ser Arg Ile Val Thr Ser Glu Gln Leu    795
His Lys Val Lys Val Val Thr Arg Ile Tyr His Lys Ala Lys His    810
Thr Lys Ala Trp Cys Pro Arg Pro Pro Arg Ala Val Gln Tyr Ser    825
His Thr His Thr Thr Asn Tyr Lys Leu Ser Ser Glu Val His Asn    840
Asp Val Ala Ile Arg Pro Ala Thr Asn Leu Thr Thr Val Gly Pro    855
Ser Asp Met Tyr                                                 859
HRV39 Attn WT
                                                 (SEQ ID NO: 74)
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
Cys Gly Tyr Ser Asp Arg Ile Ile Gln Ile Thr Arg Gly Asp Ser    90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Glu Ser Lys Val Trp Lys Arg Asp Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Arg Ala Asn Asn Glu Lys Gln Pro Ser Asp Asp Asn    240
Trp Leu Asn Phe Asp Gly Thr Leu Leu Gly Asn Leu Leu Ile Phe    255
```

-continued

```
Pro His Gln Phe Ile Asn Leu Arg Ser Asn Asn Ser Ala Thr Ile      270
Ile Val Pro Tyr Val Asn Ala Val Pro Met Asp Ser Met Leu Arg      285
His Asn Asn Trp Ser Leu Leu Ile Ile Pro Val Ser Pro Leu Asp      300
Ala Asp Thr Ser Ala Thr Ala Ile Val Pro Ile Thr Val Ser Ile      315
Ser Pro Met Phe Ser Glu Phe Ser Gly Ala Arg Ala Arg Pro Ala      330
Ala Ala Thr Gln Gly Leu Pro Val Tyr Met Thr Pro Gly Ser Gly      345
Gln Phe Leu Thr Thr Asp Asp Leu Gln Ser Pro Ser Ala Leu Pro      360
Trp Tyr His Pro Thr Lys Glu Ile Phe Ile Pro Gly Gln Val Arg      375
Asn Leu Ile Glu Met Cys Gln Val Asp Thr Met Ile Pro Ile Asn      390
Asn Thr Asn Glu Arg Ile Gly Asn Val Asn Met Tyr Thr Val Ser      405
Leu Thr Ser Gln Thr Asn Thr Ala Glu Gln Ile Phe Ala Ile Lys      420
Val Asp Ile Ala Ser Gln Pro Leu Ser Ser Thr Leu Ile Gly Glu      435
Ile Ala Ser Tyr Tyr Thr His Trp Thr Gly Ser Leu Arg Phe Ser      450
Phe Met Phe Cys Gly Thr Ala Asn Thr Thr Leu Lys Leu Leu Leu      465
Ala Tyr Thr Pro Pro Gly Ile Asp Lys Pro Thr Thr Arg Lys Gln      480
Ala Met Leu Gly Thr His Ile Val Trp Asp Ile Gly Leu Gln Ser      495
Thr Val Ser Leu Val Val Pro Trp Val Ser Ala Ser His Phe Arg      510
Tyr Thr Thr Pro Asp Thr Tyr Ser Met Ala Gly Tyr Ile Thr Cys      525
Trp Tyr Gln Thr Asn Phe Val Phe Pro Pro Asn Thr Pro Asn Asn      540
Ala Asn Met Ile Cys Phe Val Ser Gly Cys Lys Asp Phe Cys Leu      555
Arg Met Ala Arg Asp Thr Asp Met His Val Gln Asn Val Pro Ile      570
Thr Gln Asn Pro Val Glu Asn Tyr Ile Asp Glu Val Leu Asn Glu      585
Val Leu Val Val Pro Asn Ile Arg Glu Ser His Pro Thr Thr Ser      600
Asn Ala Ala Thr Ala Leu Asp Ala Ala Gly Thr Gly His Thr Ser      615
Ser Ile Gln Pro Glu Asp Thr Ile Glu Thr Arg Tyr Val Gln Thr      630
Ser His Thr Arg Asp Glu Met Ser Val Glu Ser Phe Leu Gly Arg      645
Ser Gly Cys Ile His Ile Ser Thr Ile Thr Met Lys Lys Glu Asn      660
Tyr Asn Asp His Asn Phe Val Asp Trp Lys Ile Thr Leu Gln Glu      675
Met Ala Gln Val Arg Arg Lys Phe Glu Met Phe Thr Tyr Val Arg      690
Phe Asp Ser Glu Ile Thr Leu Val Pro Cys Ile Ala Gly Arg Gly      705
Glu Asp Ile Gly His Ile Val Met Gln Tyr Met Tyr Val Pro Pro      720
Gly Ala Pro Val Pro Lys Lys Arg Asp Asp Tyr Thr Trp Gln Ser      735
Gly Thr Asn Ala Ser Val Phe Trp Gln His Gly Gln Pro Tyr Pro      750
Arg Phe Ser Leu Pro Phe Leu Ser Ile Ala Ser Ala Tyr Tyr Met      765
Phe Tyr Asp Gly Tyr Asp Gly Asp Lys Ser Ser Ser Arg Tyr Gly      780
Val Ser Val Thr Asn Asp Met Gly Thr Leu Cys Thr Arg Ile Val      795
Thr Asn Gln Gln Glu His leu Val Glu Val Thr Thr Arg Val Tyr      810
His Lys Ala Lys His Val Lys Ala Trp Cys Pro Arg Ala Pro Arg      825
Ala Val Pro Tyr Thr His Ser Asn Val Thr Asn Tyr Lys Val Arg      840
Asp Gly Glu Pro Thr Leu Phe Ile Lys Ser Arg Glu Asn Leu Thr      855
```

-continued

Thr Ala Gly Pro Ser Asp Met Tyr          863

HRV39 Attn M1
(SEQ ID NO: 75)
Met Gly Ala Gln Val Ser Arg Gln Asn Val Gly Thr His Ser Thr   15
Gln Asn Ser Val Ser Gly Gly Ser Ser Leu Asn Tyr Phe Asn Ile   30
Asn Tyr Phe Lys Asp Ala Ala Ser Ser Gly Ala Ser Lys Leu Glu   45
Phe Ser Gln Asp Pro Ser Lys Phe Thr Asp Pro Val Lys Asp Val   60
Leu Glu Lys Gly Ile Pro Thr Leu Gln Ser Pro Thr Val Glu Ala   75
Cys Gly Tyr Ser Asp Arg Ile Ile Gln Ile Thr Arg Gly Asp Ser   90
Thr Ile Thr Ser Gln Asp Val Ala Asn Ala Val Val Gly Tyr Gly  105
Val Trp Pro His Tyr Leu Thr Ala Asp Asp Ala Ser Ala Ile Asp  120
Lys Pro Thr Gln Pro Asp Thr Ser Ser Asn Arg Phe Tyr Thr Leu  135
Glu Ser Lys Val Trp Lys Arg Asp Ser Lys Gly Trp Trp Trp Lys  150
Leu Pro Asp Ala Leu Lys Asp Met Gly Ile Phe Gly Glu Asn Met  165
Tyr Tyr His Phe Leu Gly Arg Ser Gly Tyr Thr Val His Val Gln  180
Cys Asn Ala Ser Lys Phe His Gln Gly Thr Leu Leu Ile Ala Met  195
Val Pro Glu His Gln Leu Ala Ser Ala Asn Tyr Gly Asn Val Thr  210
Ala Gly Tyr Asn Tyr Thr His Pro Gly Glu Ala Gly Arg Asp Val  225
Gly Gln Gln Arg Ala Asn Asn Glu Lys Gln Pro Ser Asp Asp Asn  240
Trp Leu Asn Phe Asp Gly Thr Leu Leu Gly Asn Leu Leu Ile Phe  255
Pro His Gln Phe Ile Asn Leu Arg Ser Asn Asn Ser Ala Thr Ile  270
Ile Val Pro Tyr Val Asn Ala Val Pro Met Asp Ser Met Leu Arg  285
His Asn Asn Trp Ser Leu Leu Ile Ile Pro Val Ser Pro Leu Asp  300
Ala Asp Thr Ser Ala Thr Ala Ile Val Pro Ile Thr Val Ser Ile  315
Ser Pro Met Phe Ser Glu Phe Ser Gly Ala Arg Ala Arg Pro Ala  330
Ala Ala Thr Gln Gly Leu Pro Val Tyr Met Thr Pro Gly Ser Gly  345
Gln Phe Leu Thr Thr Asp Asp Leu Gln Ser Pro Ser Ala Leu Pro  360
Trp Tyr His Pro Thr Lys Glu Ile Phe Ile Pro Gly Gln Val Arg  375
Asn Leu Ile Glu Met Cys Gln Val Asp Thr Met Ile Pro Ile Asn  390
Asn Thr Asn Glu Arg Ile Gly Asn Val Asn Met Tyr Thr Val Ser  405
Leu Thr Ser Gln Thr Asn Thr Ala Glu Gln Ile Phe Ala Ile Lys  420
Val Asp Ile Ala Ser Gln Pro Leu Ser Ser Thr Leu Ile Gly Glu  435
Ile Ala Ser Tyr Tyr Thr His Trp Thr Gly Ser Leu Arg Phe Ser  450
Phe Met Phe Cys Gly Thr Ala Asn Thr Thr Leu Lys Leu Leu Leu  465
Ala Tyr Thr Pro Pro Gly Ile Asp Lys Pro Thr Thr Arg Lys Gln  480
Ala Met Leu Gly Thr His Ile Val Trp Asp Ile Gly Leu Gln Ser  495
Thr Val Ser Leu Val Val Pro Trp Val Ser Ala Ser His Phe Arg  510
Tyr Thr Thr Pro Asp Thr Tyr Ser Met Ala Gly Tyr Ile Thr Cys  525
Trp Tyr Gln Thr Asn Phe Val Phe Pro Pro Asn Thr Pro Asn Asn  540
Ala Asn Met Ile Cys Phe Val Ser Gly Cys Lys Asp Phe Cys Leu  555
Arg Met Ala Arg Asp Thr Asp Met His Val Gln Asn Val Pro Ile  570
Thr Gln Asn Pro Val Glu Asn Tyr Ile Asp Glu Val Leu Asn Glu  585

-continued

```
Val Leu Val Val Pro Asn Ile Arg Glu Ser His Pro Thr Thr Ser    600
Asn Ala Ala Thr Ala Leu Asp Ala Ala Gly Thr Gly His Thr Ser    615
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Lys Lys Glu Asn    660
Tyr Asn Asp Ala Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Glu His leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863
```

HRV39 Attn M2

(SEQ ID NO: 76)

```
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
Cys Gly Tyr Ser Asp Arg Ile Ile Gln Ile Thr Arg Gly Asp Ser    90
Thr Ile Thr Ser Gln Asp Val Ala Asn Ala Val Val Gly Tyr Gly    105
Val Trp Pro His Tyr Leu Thr Ala Asp Ala Ser Ala Ile Asp    120
Lys Pro Thr Gln Pro Asp Thr Ser Ser Asn Arg Phe Tyr Thr Leu    135
Glu Ser Lys Val Trp Lys Arg Asp Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Arg Ala Asn Asn Glu Lys Gln Pro Ser Asp Asp Asn    240
Trp Leu Asn Phe Asp Gly Thr Leu Leu Gly Asn Leu Leu Ile Phe    255
Pro His Gln Phe Ile Asn Leu Arg Ser Asn Asn Ser Ala Thr Ile    270
Ile Val Pro Tyr Val Asn Ala Val Pro Met Asp Ser Met Leu Arg    285
His Asn Asn Trp Ser Leu Leu Ile Ile Pro Val Ser Pro Leu Asp    300
```

-continued

```
Ala Asp Thr Ser Ala Thr Ala Ile Val Pro Ile Thr Val Ser Ile     315
Ser Pro Met Phe Ser Glu Phe Ser Gly Ala Arg Ala Arg Pro Ala     330
Ala Ala Thr Gln Gly Leu Pro Val Tyr Met Thr Pro Gly Ser Gly     345
Gln Phe Leu Thr Thr Asp Asp Leu Gln Ser Pro Ser Ala Leu Pro     360
Trp Tyr His Pro Thr Lys Glu Ile Phe Ile Pro Gly Gln Val Arg     375
Asn Leu Ile Glu Met Cys Gln Val Asp Thr Met Ile Pro Ile Asn     390
Asn Thr Asn Glu Arg Ile Gly Asn Val Asn Met Tyr Thr Val Ser     405
Leu Thr Ser Gln Thr Asn Thr Ala Glu Gln Ile Phe Ala Ile Lys     420
Val Asp Ile Ala Ser Gln Pro Leu Ser Ser Thr Leu Ile Gly Glu     435
Ile Ala Ser Tyr Tyr Thr His Trp Thr Gly Ser Leu Arg Phe Ser     450
Phe Met Phe Cys Gly Thr Ala Asn Thr Thr Leu Lys Leu Leu Leu     465
Ala Tyr Thr Pro Pro Gly Ile Asp Lys Pro Thr Thr Arg Lys Gln     480
Ala Met Leu Gly Thr His Ile Val Trp Asp Ile Gly Leu Gln Ser     495
Thr Val Ser Leu Val Val Pro Trp Val Ser Ala Ser His Phe Arg     510
Tyr Thr Thr Pro Asp Thr Tyr Ser Met Ala Gly Tyr Ile Thr Cys     525
Trp Tyr Gln Thr Asn Phe Val Phe Pro Pro Asn Thr Pro Asn Asn     540
Ala Asn Met Ile Cys Phe Val Ser Gly Cys Lys Asp Phe Cys Leu     555
Arg Met Ala Arg Asp Thr Asp Met His Val Gln Asn Val Pro Ile     570
Thr Gln Asn Pro Val Glu Asn Tyr Ile Asp Glu Val Leu Asn Glu     585
Val Leu Val Val Pro Asn Ile Arg Glu Ser His Pro Thr Thr Ser     600
Asn Ala Ala Thr Ala Leu Asp Ala Ala Gly Thr Gly His Thr Ser     615
Ser Ile Gln Pro Glu Asp Thr Ile Glu Thr Arg Tyr Val Gln Thr     630
Ser His Thr Arg Asp Glu Met Ser Val Glu Ser Phe Leu Gly Arg     645
Ser Gly Cys Ile His Ile Ser Thr Ile Thr Met Lys Lys Glu Asn     660
Tyr Asn Asp His Asn Phe Val Asp Trp Lys Ile Thr Leu Gln Glu     675
Met Ala Gln Val Arg Arg Lys Phe Glu Met Phe Thr Tyr Val Arg     690
Phe Asp Ser Glu Ile Thr Leu Val Pro Cys Ile Ala Gly Arg Gly     705
Glu Asp Ile Gly His Ile Val Met Gln Tyr Met Tyr Val Pro Pro     720
Gly Ala Pro Val Pro Lys Lys Arg Asp Asp Tyr Thr Trp Gln Ser     735
Gly Thr Asn Ala Ser Val Phe Trp Gln His Gly Gln Pro Tyr Pro     750
Arg Phe Ser Leu Pro Phe Leu Ser Ile Ala Ser Ala Tyr Tyr Met     765
Phe Tyr Asp Gly Tyr Asp Gly Asp Lys Ser Ser Ser Arg Tyr Gly     780
Val Ser Val Thr Asn Asp Met Gly Thr Leu Cys Thr Arg Ile Val     795
Thr Asn Gln Gln Glu His leu Val Glu Val Thr Thr Arg Val Tyr     810
His Lys Ala Lys His Val Lys Ala Trp Cys Pro Arg Ala Pro Arg     825
Ala Val Pro Tyr Thr His Ser Asn Val Thr Asn Tyr Lys Val Arg     840
Asp Gly Glu Pro Thr Leu Phe Ile Lys Ser Arg Glu Asn Leu Thr     855
Thr Ala Gly Pro Ser Asp Met Tyr                                 863
```

HRV39 Attn M3

(SEQ ID NO: 77)

```
Met Gly Ala Gln Val Ser Arg Gln Asn Val Gly Thr His Ser Thr     15
Gln Asn Ser Val Ser Gly Gly Ser Ser Leu Asn Tyr Phe Asn Ile     30
```

```
Asn Tyr Phe Lys Asp Ala Ala Ser Ser Gly Ala Ser Lys Leu Glu      45
Phe Ser Gln Asp Pro Ser Lys Phe Thr Asp Pro Val Lys Asp Val      60
Leu Glu Lys Gly Ile Pro Thr Leu Gln Ser Pro Thr Val Glu Ala      75
Cys Gly Tyr Ser Asp Arg Ile Ile Gln Ile Thr Arg Gly Asp Ser      90
Thr Ile Thr Ser Gln Asp Val Ala Asn Ala Val Val Gly Tyr Gly     105
Val Trp Pro His Tyr Leu Thr Ala Asp Ala Ser Ala Ile Asp         120
Lys Pro Thr Gln Pro Asp Thr Ser Ser Asn Arg Phe Tyr Thr Leu     135
Glu Ser Lys Val Trp Lys Arg Asp Ser Lys Gly Trp Trp Lys         150
Leu Pro Asp Ala Leu Lys Asp Met Gly Ile Phe Gly Glu Asn Met     165
Tyr Tyr His Phe Leu Gly Arg Ser Gly Tyr Thr Val His Val Gln     180
Cys Asn Ala Ser Lys Phe His Gln Gly Thr Leu Leu Ile Ala Met     195
Val Pro Glu His Gln Leu Ala Ser Ala Asn Tyr Gly Asn Val Thr     210
Ala Gly Tyr Asn Tyr Thr His Pro Gly Glu Ala Gly Arg Asp Val     225
Gly Gln Gln Arg Ala Asn Asn Glu Lys Gln Pro Ser Asp Asp Asn     240
Trp Leu Asn Phe Asp Gly Thr Leu Leu Gly Asn Leu Leu Ile Phe     255
Pro His Gln Phe Ile Asn Leu Arg Ser Asn Asn Ser Ala Thr Ile     270
Ile Val Pro Tyr Val Asn Ala Val Pro Met Asp Ser Met Leu Arg     285
His Asn Asn Trp Ser Leu Leu Ile Ile Pro Val Ser Pro Leu Asp     300
Ala Asp Thr Ser Ala Thr Ala Ile Val Pro Ile Thr Val Ser Ile     315
Ser Pro Met Phe Ser Glu Phe Ser Gly Ala Arg Ala Arg Pro Ala     330
Ala Ala Thr Gln Gly Leu Pro Val Tyr Met Thr Pro Gly Ser Gly     345
Gln Phe Leu Thr Thr Asp Asp Leu Gln Ser Pro Ser Ala Leu Pro     360
Trp Tyr His Pro Thr Lys Glu Ile Phe Ile Pro Gly Gln Val Arg     375
Asn Leu Ile Glu Met Cys Gln Val Asp Thr Met Ile Pro Ile Asn     390
Asn Thr Asn Glu Arg Ile Gly Asn Val Asn Met Tyr Thr Val Ser     405
Leu Thr Ser Gln Thr Asn Thr Ala Glu Gln Ile Phe Ala Ile Lys     420
Val Asp Ile Ala Ser Gln Pro Leu Ser Ser Thr Leu Ile Gly Glu     435
Ile Ala Ser Tyr Tyr Thr His Trp Thr Gly Ser Leu Arg Phe Ser     450
Phe Met Phe Cys Gly Thr Ala Asn Thr Thr Leu Lys Leu Leu Leu     465
Ala Tyr Thr Pro Pro Gly Ile Asp Lys Pro Thr Thr Arg Lys Gln     480
Ala Met Leu Gly Thr His Ile Val Trp Asp Ile Gly Leu Gln Ser     495
Thr Val Ser Leu Val Val Pro Trp Val Ser Ala Ser His Phe Arg     510
Tyr Thr Thr Pro Asp Thr Tyr Ser Met Ala Gly Tyr Ile Thr Cys     525
Trp Tyr Gln Thr Asn Phe Val Phe Pro Pro Asn Thr Pro Asn Asn     540
Ala Asn Met Ile Cys Phe Val Ser Gly Cys Lys Asp Phe Cys Leu     555
Arg Met Ala Arg Asp Thr Asp Met His Val Gln Asn Val Pro Ile     570
Thr Gln Asn Pro Val Glu Asn Tyr Ile Asp Glu Val Leu Asn Glu     585
Val Leu Val Val Pro Asn Ile Arg Glu Ser His Pro Thr Thr Ser     600
Asn Ala Ala Thr Ala Leu Asp Ala Ala Gly Thr Gly His Thr Ser     615
Ser Ile Gln Pro Glu Asp Thr Ile Glu Thr Arg Tyr Val Gln Thr     630
```

-continued

```
Ser His Thr Arg Asp Glu Met Ser Val Glu Ser Phe Leu Gly Arg    645
Ser Gly Cys Ile His Ile Ser Thr Ile Thr Met Lys Lys Gln Asn    660
Tyr Asn Gln His Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Glu His leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863
```

HRV39 Attn M4

(SEQ ID NO: 78)

```
Met Gly Ala Gln Val Ser Arg Gln Asn Val Gly Thr His Ser Thr     15
Gln Asn Ser Val Ser Gly Gly Ser Ser Leu Asn Tyr Phe Asn Ile     30
Asn Tyr Phe Lys Asp Ala Ala Ser Ser Gly Ala Ser Lys Leu Glu     45
Phe Ser Gln Asp Pro Ser Lys Phe Thr Asp Pro Val Lys Asp Val     60
Leu Glu Lys Gly Ile Pro Thr Leu Gln Ser Pro Thr Val Glu Ala     75
Cys Gly Tyr Ser Asp Arg Ile Ile Gln Ile Thr Arg Gly Asp Ser     90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Glu Ser Lys Val Trp Lys Arg Asp Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Arg Ala Asn Asn Glu Lys Gln Pro Ser Asp Asp Asn    240
Trp Leu Asn Phe Asp Gly Thr Leu Leu Gly Asn Leu Leu Ile Phe    255
Pro His Gln Phe Ile Asn Leu Arg Ser Asn Asn Ser Ala Thr Ile    270
Ile Val Pro Tyr Val Asn Ala Val Pro Met Asp Ser Met Leu Arg    285
His Asn Asn Trp Ser Leu Leu Ile Ile Pro Val Ser Pro Leu Asp    300
Ala Asp Thr Ser Ala Thr Ala Ile Val Pro Ile Thr Val Ser Ile    315
Ser Pro Met Phe Ser Glu Phe Ser Gly Ala Arg Ala Arg Pro Ala    330
Ala Ala Thr Gln Gly Leu Pro Val Tyr Met Thr Pro Gly Ser Gly    345
Gln Phe Leu Thr Thr Asp Asp Leu Gln Ser Pro Ser Ala Leu Pro    360
```

```
Trp Tyr His Pro Thr Lys Glu Ile Phe Ile Pro Gly Gln Val Arg    375
Asn Leu Ile Glu Met Cys Gln Val Asp Thr Met Ile Pro Ile Asn    390
Asn Thr Asn Glu Arg Ile Gly Asn Val Asn Met Tyr Thr Val Ser    405
Leu Thr Ser Gln Thr Asn Thr Ala Glu Gln Ile Phe Ala Ile Lys    420
Val Asp Ile Ala Ser Gln Pro Leu Ser Ser Thr Leu Ile Gly Glu    435
Ile Ala Ser Tyr Tyr Thr His Trp Thr Gly Ser Leu Arg Phe Ser    450
Phe Met Phe Cys Gly Thr Ala Asn Thr Thr Leu Lys Leu Leu Leu    465
Ala Tyr Thr Pro Pro Gly Ile Asp Lys Pro Thr Thr Arg Lys Gln    480
Ala Met Leu Gly Thr His Ile Val Trp Asp Ile Gly Leu Gln Ser    495
Thr Val Ser Leu Val Val Pro Trp Val Ser Ala Ser His Phe Arg    510
Tyr Thr Thr Pro Asp Thr Tyr Ser Met Ala Gly Tyr Ile Thr Cys    525
Trp Tyr Gln Thr Asn Phe Val Phe Pro Pro Asn Thr Pro Asn Asn    540
Ala Asn Met Ile Cys Phe Val Ser Gly Cys Lys Asp Phe Cys Leu    555
Arg Met Ala Arg Asp Thr Asp Met His Val Gln Asn Val Pro Ile    570
Thr Gln Asn Pro Val Glu Asn Tyr Ile Asp Glu Val Leu Asn Glu    585
Val Leu Val Val Pro Asn Ile Arg Glu Ser His Pro Thr Thr Ser    600
Asn Ala Ala Thr Ala Leu Asp Ala Ala Gly Thr Gly His Thr Ser    615
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Lys Lys Glu Asn    660
Tyr Asn Asp His Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Ala His leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863
HRV39 Attn M5
                                                 (SEQ ID NO: 79)
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
```

-continued

| | | | | | | | | | | | | | |
|---|---|---|---|---|---|---|---|---|---|---|---|---|---|
| Cys | Gly | Tyr | Ser | Asp | Arg | Ile | Ile | Gln | Ile | Thr | Arg | Gly | Asp | Ser | 90 |
| Thr | Ile | Thr | Ser | Gln | Asp | Val | Ala | Asn | Ala | Val | Val | Gly | Tyr | Gly | 105 |
| Val | Trp | Pro | His | Tyr | Leu | Thr | Ala | Asp | Ala | Ser | Ala | Ile | Asp | 120 |
| Lys | Pro | Thr | Gln | Pro | Asp | Thr | Ser | Ser | Asn | Arg | Phe | Tyr | Thr | Leu | 135 |
| Glu | Ser | Lys | Val | Trp | Lys | Arg | Asp | Ser | Lys | Gly | Trp | Trp | Trp | Lys | 150 |
| Leu | Pro | Asp | Ala | Leu | Lys | Asp | Met | Gly | Ile | Phe | Gly | Glu | Asn | Met | 165 |
| Tyr | Tyr | His | Phe | Leu | Gly | Arg | Ser | Gly | Tyr | Thr | Val | His | Val | Gln | 180 |
| Cys | Asn | Ala | Ser | Lys | Phe | His | Gln | Gly | Thr | Leu | Leu | Ile | Ala | Met | 195 |
| Val | Pro | Glu | His | Gln | Leu | Ala | Ser | Ala | Asn | Tyr | Gly | Asn | Val | Thr | 210 |
| Ala | Gly | Tyr | Asn | Tyr | Thr | His | Pro | Gly | Glu | Ala | Gly | Arg | Asp | Val | 225 |
| Gly | Gln | Gln | Arg | Ala | Asn | Asn | Glu | Lys | Gln | Pro | Ser | Asp | Asp | Asn | 240 |
| Trp | Leu | Asn | Phe | Asp | Gly | Thr | Leu | Leu | Gly | Asn | Leu | Leu | Ile | Phe | 255 |
| Pro | His | Gln | Phe | Ile | Asn | Leu | Arg | Ser | Asn | Asn | Ser | Ala | Thr | Ile | 270 |
| Ile | Val | Pro | Tyr | Val | Asn | Ala | Val | Pro | Met | Asp | Ser | Met | Leu | Arg | 285 |
| His | Asn | Asn | Trp | Ser | Leu | Leu | Ile | Ile | Pro | Val | Ser | Pro | Leu | Asp | 300 |
| Ala | Asp | Thr | Ser | Ala | Thr | Ala | Ile | Val | Pro | Ile | Thr | Val | Ser | Ile | 315 |
| Ser | Pro | Met | Phe | Ser | Glu | Phe | Ser | Gly | Ala | Arg | Ala | Arg | Pro | Ala | 330 |
| Ala | Ala | Thr | Gln | Gly | Leu | Pro | Val | Tyr | Met | Thr | Pro | Gly | Ser | Gly | 345 |
| Gln | Phe | Leu | Thr | Thr | Asp | Asp | Leu | Gln | Ser | Pro | Ser | Ala | Leu | Pro | 360 |
| Trp | Tyr | His | Pro | Thr | Lys | Glu | Ile | Phe | Ile | Pro | Gly | Gln | Val | Arg | 375 |
| Asn | Leu | Ile | Glu | Met | Cys | Gln | Val | Asp | Thr | Met | Ile | Pro | Ile | Asn | 390 |
| Asn | Thr | Asn | Glu | Arg | Ile | Gly | Asn | Val | Asn | Met | Tyr | Thr | Val | Ser | 405 |
| Leu | Thr | Ser | Gln | Thr | Asn | Thr | Ala | Glu | Gln | Ile | Phe | Ala | Ile | Lys | 420 |
| Val | Asp | Ile | Ala | Ser | Gln | Pro | Leu | Ser | Ser | Thr | Leu | Ile | Gly | Glu | 435 |
| Ile | Ala | Ser | Tyr | Tyr | Thr | His | Trp | Thr | Gly | Ser | Leu | Arg | Phe | Ser | 450 |
| Phe | Met | Phe | Cys | Gly | Thr | Ala | Asn | Thr | Thr | Leu | Lys | Leu | Leu | Leu | 465 |
| Ala | Tyr | Thr | Pro | Pro | Gly | Ile | Asp | Lys | Pro | Thr | Thr | Arg | Lys | Gln | 480 |
| Ala | Met | Leu | Gly | Thr | His | Ile | Val | Trp | Asp | Ile | Gly | Leu | Gln | Ser | 495 |
| Thr | Val | Ser | Leu | Val | Val | Pro | Trp | Val | Ser | Ala | Ser | His | Phe | Arg | 510 |
| Tyr | Thr | Thr | Pro | Asp | Thr | Tyr | Ser | Met | Ala | Gly | Tyr | Ile | Thr | Cys | 525 |
| Trp | Tyr | Gln | Thr | Asn | Phe | Val | Phe | Pro | Pro | Asn | Thr | Pro | Asn | Asn | 540 |
| Ala | Asn | Met | Ile | Cys | Phe | Val | Ser | Gly | Cys | Lys | Asp | Phe | Cys | Leu | 555 |
| Arg | Met | Ala | Arg | Asp | Thr | Asp | Met | His | Val | Gln | Asn | Val | Pro | Ile | 570 |
| Thr | Gln | Asn | Pro | Val | Glu | Asn | Tyr | Ile | Asp | Glu | Val | Leu | Asn | Glu | 585 |
| Val | Leu | Val | Val | Pro | Asn | Ile | Arg | Glu | Ser | His | Pro | Thr | Thr | Ser | 600 |
| Asn | Ala | Ala | Thr | Ala | Leu | Asp | Ala | Ala | Gly | Thr | Gly | His | Thr | Ser | 615 |
| Ser | Ile | Gln | Pro | Glu | Asp | Thr | Ile | Glu | Thr | Arg | Tyr | Val | Gln | Thr | 630 |
| Ser | His | Thr | Arg | Asp | Glu | Met | Ser | Val | Glu | Ser | Phe | Leu | Gly | Arg | 645 |
| Ser | Gly | Cys | Ile | His | Ile | Ser | Thr | Ile | Thr | Met | Lys | Lys | Glu | Asn | 660 |
| Tyr | Asn | Asp | Ala | Asn | Phe | Val | Asp | Trp | Lys | Ile | Thr | Leu | Gln | Glu | 675 |
| Met | Ala | Gln | Val | Arg | Arg | Lys | Phe | Glu | Met | Phe | Thr | Tyr | Val | Arg | 690 |

-continued

```
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Glu His leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863
```

HRV39 Attn M6
(SEQ ID NO: 80)
```
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
Cys Gly Tyr Ser Asp Arg Ile Ile Gln Ile Thr Arg Gly Asp Ser    90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Glu Ser Lys Val Trp Lys Arg Asp Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Arg Ala Asn Asn Glu Lys Gln Pro Ser Asp Asp Asn    240
Trp Leu Asn Phe Asp Gly Thr Leu Leu Gly Asn Leu Leu Ile Phe    255
Pro His Gln Phe Ile Asn Leu Arg Ser Asn Asn Ser Ala Thr Ile    270
Ile Val Pro Tyr Val Asn Ala Val Pro Met Asp Ser Met Leu Arg    285
His Asn Asn Trp Ser Leu Leu Ile Ile Pro Val Ser Pro Leu Asp    300
Ala Asp Thr Ser Ala Thr Ala Ile Val Pro Ile Thr Val Ser Ile    315
Ser Pro Met Phe Ser Glu Phe Ser Gly Ala Arg Ala Arg Pro Ala    330
Ala Ala Thr Gln Gly Leu Pro Val Tyr Met Thr Pro Gly Ser Gly    345
Gln Phe Leu Thr Thr Asp Asp Leu Gln Ser Pro Ser Ala Leu Pro    360
Trp Tyr His Pro Thr Lys Glu Ile Phe Ile Pro Gly Gln Val Arg    375
Asn Leu Ile Glu Met Cys Gln Val Asp Thr Met Ile Pro Ile Asn    390
Asn Thr Asn Glu Arg Ile Gly Asn Val Asn Met Tyr Thr Val Ser    405
```

-continued

```
Leu Thr Ser Gln Thr Asn Thr Ala Glu Gln Ile Phe Ala Ile Lys    420
Val Asp Ile Ala Ser Gln Pro Leu Ser Ser Thr Leu Ile Gly Glu    435
Ile Ala Ser Tyr Tyr Thr His Trp Thr Gly Ser Leu Arg Phe Ser    450
Phe Met Phe Cys Gly Thr Ala Asn Thr Thr Leu Lys Leu Leu Leu    465
Ala Tyr Thr Pro Pro Gly Ile Asp Lys Pro Thr Thr Arg Lys Gln    480
Ala Met Leu Gly Thr His Ile Val Trp Asp Ile Gly Leu Gln Ser    495
Thr Val Ser Leu Val Val Pro Trp Val Ser Ala Ser His Phe Arg    510
Tyr Thr Thr Pro Asp Thr Tyr Ser Met Ala Gly Tyr Ile Thr Cys    525
Trp Tyr Gln Thr Asn Phe Val Phe Pro Pro Asn Thr Pro Asn Asn    540
Ala Asn Met Ile Cys Phe Val Ser Gly Cys Lys Asp Phe Cys Leu    555
Arg Met Ala Arg Asp Thr Asp Met His Val Gln Asn Val Pro Ile    570
Thr Gln Asn Pro Val Glu Asn Tyr Ile Asp Glu Val Leu Asn Glu    585
Val Leu Val Val Pro Asn Ile Arg Glu Ser His Pro Thr Thr Ser    600
Asn Ala Ala Thr Ala Leu Asp Ala Ala Gly Thr Gly His Thr Ser    615
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Lys Lys Glu Asn    660
Tyr Asn Asp Ala Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Ala His leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863

HRV39 Attn M7
                                                    (SEQ ID NO: 81)
Met Gly Ala Gln Val Ser Arg Gln Asn Val Gly Thr His Ser Thr     15
Gln Asn Ser Val Ser Gly Gly Ser Ser Leu Asn Tyr Phe Asn Ile     30
Asn Tyr Phe Lys Asp Ala Ala Ser Ser Gly Ala Ser Lys Leu Glu     45
Phe Ser Gln Asp Pro Ser Lys Phe Thr Asp Pro Val Lys Asp Val     60
Leu Glu Lys Gly Ile Pro Thr Leu Gln Ser Pro Thr Val Glu Ala     75
Cys Gly Tyr Ser Asp Arg Ile Ile Gln Ile Thr Arg Gly Asp Ser     90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
```

```
Glu Ser Lys Val Trp Lys Arg Asp Ser Lys Gly Trp Trp Lys      150
Leu Pro Asp Ala Leu Lys Asp Met Gly Ile Phe Gly Glu Asn Met  165
Tyr Tyr His Phe Leu Gly Arg Ser Gly Tyr Thr Val His Val Gln  180
Cys Asn Ala Ser Lys Phe His Gln Gly Thr Leu Leu Ile Ala Met  195
Val Pro Glu His Gln Leu Ala Ser Ala Asn Tyr Gly Asn Val Thr  210
Ala Gly Tyr Asn Tyr Thr His Pro Gly Glu Ala Gly Arg Asp Val  225
Gly Gln Gln Arg Ala Leu Ile Glu Lys Gln Pro Ser Asp Asp Asn  240
Trp Leu Asn Phe Asp Gly Thr Leu Leu Gly Asn Leu Leu Ile Phe  255
Pro His Gln Phe Ile Asn Leu Arg Ser Asn Asn Ser Ala Thr Ile  270
Ile Val Pro Tyr Val Asn Ala Val Pro Met Asp Ser Met Leu Arg  285
His Asn Asn Trp Ser Leu Leu Ile Ile Pro Val Ser Pro Leu Asp  300
Ala Asp Thr Ser Ala Thr Ala Ile Val Pro Ile Thr Val Ser Ile  315
Ser Pro Met Phe Ser Glu Phe Ser Gly Ala Arg Ala Arg Pro Ala  330
Ala Ala Thr Gln Gly Leu Pro Val Tyr Met Thr Pro Gly Ser Gly  345
Gln Phe Leu Thr Thr Asp Asp Leu Gln Ser Pro Ser Ala Leu Pro  360
Trp Tyr His Pro Thr Lys Glu Ile Phe Ile Pro Gly Gln Val Arg  375
Asn Leu Ile Glu Met Cys Gln Val Asp Thr Met Ile Pro Ile Asn  390
Asn Thr Asn Glu Arg Ile Gly Asn Val Asn Met Tyr Thr Val Ser  405
Leu Thr Ser Gln Thr Asn Thr Ala Glu Gln Ile Phe Ala Ile Lys  420
Val Asp Ile Ala Ser Gln Pro Leu Ser Ser Thr Leu Ile Gly Glu  435
Ile Ala Ser Tyr Tyr Thr His Trp Thr Gly Ser Leu Arg Phe Ser  450
Phe Met Phe Cys Gly Thr Ala Asn Thr Thr Leu Lys Leu Leu Leu  465
Ala Tyr Thr Pro Pro Gly Ile Asp Lys Pro Thr Thr Arg Lys Gln  480
Ala Met Leu Gly Thr His Ile Val Trp Asp Ile Gly Leu Gln Ser  495
Thr Val Ser Leu Val Val Pro Trp Val Ser Ala Ser His Phe Arg  510
Tyr Thr Thr Pro Asp Thr Tyr Ser Met Ala Gly Tyr Ile Thr Cys  525
Trp Tyr Gln Thr Asn Phe Val Phe Pro Pro Asn Thr Pro Asn Asn  540
Ala Asn Met Ile Cys Phe Val Ser Gly Cys Lys Asp Phe Cys Leu  555
Arg Met Ala Arg Asp Thr Asp Met His Val Gln Asn Val Pro Ile  570
Thr Gln Asn Pro Val Glu Asn Tyr Ile Asp Glu Val Leu Asn Glu  585
Val Leu Val Val Pro Asn Ile Arg Glu Ser His Pro Thr Thr Ser  600
Asn Ala Ala Thr Ala Leu Asp Ala Ala Gly Thr Gly His Thr Ser  615
Ser Ile Gln Pro Glu Asp Thr Ile Glu Thr Arg Tyr Val Gln Thr  630
Ser His Thr Arg Asp Glu Met Ser Val Glu Ser Phe Leu Gly Arg  645
Ser Gly Cys Ile His Ile Ser Thr Ile Thr Met Lys Lys Glu Asn  660
Tyr Asn Asp His Asn Phe Val Asp Trp Lys Ile Thr Leu Gln Glu  675
Met Ala Gln Val Arg Arg Lys Phe Glu Met Phe Thr Tyr Val Arg  690
Phe Asp Ser Glu Ile Thr Leu Val Pro Cys Ile Ala Gly Arg Gly  705
Glu Asp Ile Gly His Ile Val Met Gln Tyr Met Tyr Val Pro Pro  720
Gly Ala Pro Val Pro Lys Lys Arg Asp Asp Tyr Thr Trp Gln Ser  735
```

-continued

```
Gly Thr Asn Ala Ser Val Phe Trp Gln His Gly Gln Pro Tyr Pro      750
Arg Phe Ser Leu Pro Phe Leu Ser Ile Ala Ser Ala Tyr Tyr Met      765
Phe Tyr Asp Gly Tyr Asp Gly Asp Lys Ser Ser Ser Arg Tyr Gly      780
Val Ser Val Thr Asn Asp Met Gly Thr Leu Cys Thr Arg Ile Val      795
Thr Asn Gln Gln Glu His leu Val Glu Val Thr Thr Arg Val Tyr      810
His Lys Ala Lys His Val Lys Ala Trp Cys Pro Arg Ala Pro Arg      825
Ala Val Pro Tyr Thr His Ser Asn Val Thr Asn Tyr Lys Val Arg      840
Asp Gly Glu Pro Thr Leu Phe Ile Lys Ser Arg Glu Asn Leu Thr      855
Thr Ala Gly Pro Ser Asp Met Tyr                                  863
```

HRV39 Attn M8

(SEQ ID NO: 82)

```
Met Gly Ala Gln Val Ser Arg Gln Asn Val Gly Thr His Ser Thr       15
Gln Asn Ser Val Ser Gly Gly Ser Ser Leu Asn Tyr Phe Asn Ile       30
Asn Tyr Phe Lys Asp Ala Ala Ser Ser Gly Ala Ser Lys Leu Glu       45
Phe Ser Gln Asp Pro Ser Lys Phe Thr Asp Pro Val Lys Asp Val       60
Leu Glu Lys Gly Ile Pro Thr Leu Gln Ser Pro Thr Val Glu Ala       75
Cys Gly Tyr Ser Asp Arg Ile Ile Gln Ile Thr Arg Gly Asp Ser       90
Thr Ile Thr Ser Gln Asp Val Ala Asn Ala Val Val Gly Tyr Gly      105
Val Trp Pro His Tyr Leu Thr Ala Asp Asp Ala Ser Ala Ile Asp      120
Lys Pro Thr Gln Pro Asp Thr Ser Ser Asn Arg Phe Tyr Thr Leu      135
Glu Ser Lys Val Trp Lys Arg Asp Ser Lys Gly Trp Trp Trp Lys      150
Leu Pro Asp Ala Leu Lys Asp Met Gly Ile Phe Gly Glu Asn Met      165
Tyr Tyr His Phe Leu Gly Arg Ser Gly Tyr Thr Val His Val Gln      180
Cys Asn Ala Ser Lys Phe His Gln Gly Thr Leu Leu Ile Ala Met      195
Val Pro Glu His Gln Leu Ala Ser Ala Asn Tyr Gly Asn Val Thr      210
Ala Gly Tyr Asn Tyr Thr His Pro Gly Glu Ala Gly Arg Asp Val      225
Gly Gln Gln Arg Ala Asn Asn Glu Lys Gln Pro Ser Asp Asp Asn      240
Trp Leu Asn Phe Asp Gly Thr Leu Leu Gly Asn Leu Leu Ile Phe      255
Pro His Gln Phe Ile Asn Leu Arg Ser Asn Asn Ser Ala Thr Ile      270
Ile Val Pro Tyr Val Asn Ala Val Pro Met Asp Ser Met Leu Arg      285
His Asn Asn Trp Ser Leu Leu Ile Ile Pro Val Ser Pro Leu Asp      300
Ala Asp Thr Ser Ala Thr Ala Ile Val Pro Ile Thr Val Ser Ile      315
Ser Pro Met Phe Ser Glu Phe Ser Gly Ala Arg Ala Arg Pro Ala      330
Ala Ala Thr Gln Gly Leu Pro Val Tyr Met Thr Pro Gly Ser Gly      345
Gln Phe Leu Thr Thr Asp Asp Leu Gln Ser Pro Ser Ala Leu Pro      360
Trp Tyr His Pro Thr Lys Glu Ile Phe Ile Pro Gly Gln Val Arg      375
Asn Leu Ile Glu Met Cys Gln Val Asp Thr Met Ile Pro Ile Asn      390
Asn Thr Ala Glu Arg Ile Gly Asn Val Asn Met Tyr Thr Val Ser      405
Leu Thr Ser Gln Thr Asn Thr Ala Glu Gln Ile Phe Ala Ile Lys      420
Val Asp Ile Ala Ser Gln Pro Leu Ser Ser Thr Leu Ile Gly Glu      435
Ile Ala Ser Tyr Tyr Thr His Trp Thr Gly Ser Leu Arg Phe Ser      450
Phe Met Phe Cys Gly Thr Ala Asn Thr Thr Leu Lys Leu Leu Leu      465
```

-continued

```
Ala Tyr Thr Pro Pro Gly Ile Asp Lys Pro Thr Thr Arg Lys Gln    480
Ala Met Leu Gly Thr His Ile Val Trp Asp Ile Gly Leu Gln Ser    495
Thr Val Ser Leu Val Val Pro Trp Val Ser Ala Ser His Phe Arg    510
Tyr Thr Thr Pro Asp Thr Tyr Ser Met Ala Gly Tyr Ile Thr Cys    525
Trp Tyr Gln Thr Asn Phe Val Phe Pro Pro Asn Thr Pro Asn Asn    540
Ala Asn Met Ile Cys Phe Val Ser Gly Cys Lys Asp Phe Cys Leu    555
Arg Met Ala Arg Asp Thr Asp Met His Val Gln Asn Val Pro Ile    570
Thr Gln Asn Pro Val Glu Asn Tyr Ile Asp Glu Val Leu Asn Glu    585
Val Leu Val Val Pro Asn Ile Arg Glu Ser His Pro Thr Thr Ser    600
Asn Ala Ala Thr Ala Leu Asp Ala Ala Gly Thr Gly His Thr Ser    615
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Lys Lys Glu Asn    660
Tyr Asn Asp His Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Glu His leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863
```

HRV39 Attn M9

(SEQ ID NO: 83)
```
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
Cys Gly Tyr Ser Asp Arg Ile Ile Gln Ile Thr Arg Gly Asp Ser    90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Glu Ser Lys Val Trp Lys Arg Asp Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
```

-continued

| | | | | | | | | | | | | | | |
|---|---|---|---|---|---|---|---|---|---|---|---|---|---|---|
|Cys|Asn|Ala|Ser|Lys|Phe|His|Gln|Gly|Thr|Leu|Leu|Ile|Ala|Met|195|
|Val|Pro|Glu|His|Gln|Leu|Ala|Ser|Ala|Asn|Tyr|Gly|Asn|Val|Thr|210|
|Ala|Gly|Tyr|Asn|Tyr|Thr|His|Pro|Gly|Glu|Ala|Gly|Arg|Asp|Val|225|
|Gly|Gln|Gln|Arg|Ala|Asn|Asn|Glu|Lys|Gln|Pro|Ser|Asp|Asp|Asn|240|
|Trp|Leu|Asn|Phe|Asp|Gly|Thr|Leu|Leu|Gly|Asn|Leu|Leu|Ile|Phe|255|
|Pro|His|Gln|Phe|Ile|Asn|Leu|Arg|Ser|Asn|Asn|Ser|Ala|Thr|Ile|270|
|Ile|Val|Pro|Tyr|Val|Asn|Ala|Val|Pro|Met|Asp|Ser|Met|Leu|Arg|285|
|His|Asn|Asn|Trp|Ser|Leu|Leu|Ile|Ile|Pro|Val|Ser|Pro|Leu|Asp|300|
|Ala|Asp|Thr|Ser|Ala|Thr|Ala|Ile|Val|Pro|Ile|Thr|Val|Ser|Ile|315|
|Ser|Pro|Met|Phe|Ser|Glu|Phe|Ser|Gly|Ala|Arg|Ala|Arg|Pro|Ala|330|
|Ala|Ala|Thr|Gln|Gly|Leu|Pro|Val|Tyr|Met|Thr|Pro|Gly|Ser|Gly|345|
|Gln|Phe|Leu|Thr|Thr|Asp|Asp|Leu|Gln|Ser|Pro|Ser|Ala|Leu|Pro|360|
|Trp|Tyr|His|Pro|Thr|Lys|Glu|Ile|Phe|Ile|Pro|Gly|Gln|Val|Arg|375|
|Asn|Leu|Ile|Glu|Met|Cys|Gln|Val|Asp|Thr|Met|Ile|Pro|Ile|Asn|390|
|Asn|Thr|Asn|Glu|Arg|Ile|Gly|Asn|Val|Asn|Met|Tyr|Thr|Val|Ser|405|
|Leu|Thr|Ser|Gln|Thr|Asn|Thr|Ala|Glu|Gln|Ile|Phe|Ala|Ile|Lys|420|
|Val|Asp|Ile|Ala|Ser|Gln|Pro|Leu|Ser|Ser|Thr|Leu|Ile|Gly|Glu|435|
|Ile|Ala|Ser|Tyr|Tyr|Thr|His|Trp|Thr|Gly|Ser|Leu|Arg|Phe|Ser|450|
|Phe|Met|Phe|Cys|Gly|Thr|Ala|Asn|Thr|Thr|Leu|Lys|Leu|Leu|Leu|465|
|Ala|Tyr|Thr|Pro|Pro|Gly|Ile|Asp|Lys|Pro|Thr|Thr|Arg|Lys|Gln|480|
|Ala|Met|Leu|Gly|Thr|His|Ile|Val|Trp|Asp|Ile|Gly|Leu|Gln|Ser|495|
|Thr|Val|Ser|Leu|Val|Val|Pro|Trp|Val|Ser|Ala|Ser|His|Phe|Arg|510|
|Tyr|Thr|Thr|Pro|Asp|Thr|Tyr|Ser|Met|Ala|Gly|Tyr|Ile|Thr|Cys|525|
|Trp|Tyr|Gln|Thr|Asn|Phe|Val|Phe|Pro|Pro|Asn|Thr|Pro|Asn|Asn|540|
|Ala|Asn|Met|Ile|Cys|Phe|Val|Ser|Gly|Cys|Lys|Asp|Phe|Cys|Leu|555|
|Arg|Met|Ala|Arg|Asp|Thr|Asp|Met|His|Val|Gln|Asn|Val|Pro|Ile|570|
|Thr|Gln|Asn|Pro|Val|Glu|Asn|Tyr|Ile|Asp|Glu|Val|Leu|Asn|Glu|585|
|Val|Leu|Val|Val|Pro|Asn|Ile|Arg|Glu|Ser|His|Pro|Thr|Thr|Ser|600|
|Asn|Ala|Ala|Thr|Ala|Leu|Asp|Ala|Ala|Gly|Thr|Gly|His|Thr|Ser|615|
|Ser|Ile|Gln|Pro|Glu|Asp|Thr|Ile|Glu|Thr|Arg|Tyr|Val|Gln|Thr|630|
|Ser|His|Thr|Arg|Asp|Glu|Met|Ser|Val|Glu|Ser|Phe|Leu|Gly|Arg|645|
|Ser|Gly|Cys|Ile|His|Ile|Ser|Thr|Ile|Thr|Met|Lys|Lys|Glu|Asn|660|
|Tyr|Asn|Asp|His|Asn|Phe|Val|Asp|Trp|Lys|Ile|Thr|Leu|Gln|Glu|675|
|Met|Ala|Gln|Val|Arg|Arg|Lys|Phe|Glu|Met|Phe|Thr|Tyr|Val|Arg|690|
|Phe|Asp|Ser|Glu|Ile|Thr|Leu|Val|Pro|Cys|Ile|Ala|Gly|Arg|Gly|705|
|Glu|Asp|Ile|Gly|His|Ile|Val|Met|Gln|Tyr|Met|Tyr|Val|Pro|Pro|720|
|Gly|Ala|Pro|Val|Pro|Lys|Lys|Arg|Asp|Asp|Tyr|Thr|Trp|Gln|Ser|735|
|Gly|Thr|Asn|Ala|Ser|Val|Phe|Trp|Gln|His|Gly|Gln|Pro|Tyr|Pro|750|
|Arg|Phe|Ser|Leu|Pro|Phe|Leu|Ser|Ile|Ala|Ser|Ala|Tyr|Tyr|Met|765|
|Phe|Tyr|Asp|Gly|Tyr|Asp|Gly|Asp|Lys|Ser|Ser|Ser|Arg|Tyr|Gly|780|
|Val|Ser|Val|Thr|Asn|Asp|Met|Gly|Thr|Leu|Cys|Thr|Arg|Ile|Val|795|

-continued

```
Thr Asn Gln Gln Glu His Leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Ala Val Arg    840
Asp Gly Glu Pro Thr Leu Phe Ile Lys Ser Arg Glu Asn Leu Thr    855
Thr Ala Gly Pro Ser Asp Met Tyr                                 863
```

HRV39 Attn M10
(SEQ ID NO: 84)

```
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
Cys Gly Tyr Ser Asp Arg Ile Ile Gln Ile Thr Arg Gly Asp Ser    90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Glu Ser Lys Val Trp Lys Arg Asp Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Ile Thr Asn Asn Gln Lys Gln Pro Ser Asp Asp Asn    240
Trp Leu Asn Phe Asp Gly Thr Leu Leu Gly Asn Leu Leu Ile Phe    255
Pro His Gln Phe Ile Asn Leu Arg Ser Asn Asn Ser Ala Thr Ile    270
Ile Val Pro Tyr Val Asn Ala Val Pro Met Asp Ser Met Leu Arg    285
His Asn Asn Trp Ser Leu Leu Ile Ile Pro Val Ser Pro Leu Asp    300
Ala Asp Thr Ser Ala Thr Ala Ile Val Pro Ile Thr Val Ser Ile    315
Ser Pro Met Phe Ser Glu Phe Ser Gly Ala Arg Ala Arg Pro Ala    330
Ala Ala Thr Gln Gly Leu Pro Val Tyr Met Thr Pro Gly Ser Gly    345
Gln Phe Leu Thr Thr Asp Asp Leu Gln Ser Pro Ser Ala Leu Pro    360
Trp Tyr His Pro Thr Lys Glu Ile Phe Ile Pro Gly Gln Val Arg    375
Asn Leu Ile Glu Met Cys Gln Val Asp Thr Met Ile Pro Ile Asn    390
Asn Thr Asn Glu Ala Ile Gly Asn Val Asn Met Tyr Thr Val Ser    405
Leu Thr Ser Gln Thr Asn Thr Ala Glu Gln Ile Phe Ala Ile Lys    420
Val Asp Ile Ala Ser Gln Pro Leu Ser Ser Thr Leu Ile Gly Glu    435
Ile Ala Ser Tyr Tyr Thr His Trp Thr Gly Ser Leu Arg Phe Ser    450
Phe Met Phe Cys Gly Thr Ala Asn Thr Thr Leu Lys Leu Leu Leu    465
Ala Tyr Thr Pro Pro Gly Ile Asp Lys Pro Thr Thr Arg Lys Gln    480
Ala Met Leu Gly Thr His Ile Val Trp Asp Ile Gly Leu Gln Ser    495
Thr Val Ser Leu Val Val Pro Trp Val Ser Ala Ser His Phe Arg    510
```

```
Tyr Thr Thr Pro Asp Thr Tyr Ser Met Ala Gly Tyr Ile Thr Cys    525
Trp Tyr Gln Thr Asn Phe Val Phe Pro Pro Asn Thr Pro Asn Asn    540
Ala Asn Met Ile Cys Phe Val Ser Gly Cys Lys Asp Phe Cys Leu    555
Arg Met Ala Arg Asp Thr Asp Met His Val Gln Asn Val Pro Ile    570
Thr Gln Asn Pro Val Glu Asn Tyr Ile Asp Glu Val Leu Asn Glu    585
Val Leu Val Val Pro Asn Ile Arg Glu Ser His Pro Thr Thr Ser    600
Asn Ala Ala Thr Ala Leu Asp Ala Ala Gly Thr Gly His Thr Ser    615
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Lys Lys Glu Asn    660
Tyr Asn Asp His Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Glu His Leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863
HRV39 Attn M11
                                                     (SEQ ID NO: 85)
Met Gly Ala Gln Val Ser Arg Gln Asn Val Gly Thr His Ser Thr    15
Gln Asn Ser Val Ser Gly Gly Ser Ser Leu Asn Tyr Phe Asn Ile    30
Asn Tyr Phe Lys Asp Ala Ala Ser Ser Gly Ala Ser Lys Leu Glu    45
Phe Ser Gln Asp Pro Ser Lys Phe Thr Asp Pro Val Lys Asp Val    60
Leu Glu Lys Gly Ile Pro Thr Leu Gln Ser Pro Thr Val Glu Ala    75
Cys Gly Tyr Ser Asp Arg Ile Ile Gln Ile Thr Arg Gly Asp Ser    90
Thr Ile Thr Ser Gln Asp Val Ala Asn Ala Val Val Gly Tyr Gly    105
Val Trp Pro His Tyr Leu Thr Ala Asp Ala Ser Ala Ile Asp        120
Lys Pro Thr Gln Pro Asp Thr Ser Ser Asn Arg Phe Tyr Thr Leu    135
Glu Ser Lys Val Trp Lys Arg Asp Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Arg Ala Asn Asn Glu Lys Gln Pro Ser Asp Asp Asn    240
```

-continued

| | | | | | | | | | | |
|---|---|---|---|---|---|---|---|---|---|---|
|Trp|Leu|Asn|Phe|Asp|Gly|Thr|Leu|Leu|Gly|Asn|Leu|Leu|Ile|Phe|255|
|Pro|His|Gln|Phe|Ile|Asn|Leu|Arg|Ser|Asn|Asn|Ser|Ala|Thr|Ile|270|
|Ile|Val|Pro|Tyr|Val|Asn|Ala|Val|Pro|Met|Asp|Ser|Met|Leu|Arg|285|
|His|Asn|Asn|Trp|Ser|Leu|Leu|Ile|Ile|Pro|Val|Ser|Pro|Leu|Asp|300|
|Ala|Asp|Thr|Ser|Ala|Thr|Ala|Ile|Val|Pro|Ile|Thr|Val|Ser|Ile|315|
|Ser|Pro|Met|Phe|Ser|Glu|Phe|Ser|Gly|Ala|Arg|Ala|Arg|Pro|Ala|330|
|Ala|Ala|Thr|Gln|Gly|Leu|Pro|Val|Tyr|Met|Thr|Pro|Gly|Ser|Gly|345|
|Gln|Phe|Leu|Thr|Thr|Asp|Asp|Leu|Gln|Ser|Pro|Ser|Ala|Leu|Pro|360|
|Trp|Tyr|His|Pro|Thr|Lys|Glu|Ile|Phe|Ile|Pro|Gly|Gln|Val|Arg|375|
|Asn|Leu|Ile|Glu|Met|Cys|Gln|Val|Asp|Thr|Met|Ile|Pro|Ile|Asn|390|
|Asn|Thr|Asn|Glu|Ala|Ile|Gly|Asn|Val|Asn|Met|Tyr|Thr|Val|Ser|405|
|Leu|Thr|Ser|Gln|Thr|Asn|Thr|Ala|Glu|Gln|Ile|Phe|Ala|Ile|Lys|420|
|Val|Asp|Ile|Ala|Ser|Gln|Pro|Leu|Ser|Ser|Thr|Leu|Ile|Gly|Glu|435|
|Ile|Ala|Ser|Tyr|Tyr|Thr|His|Trp|Thr|Gly|Ser|Leu|Arg|Phe|Ser|450|
|Phe|Met|Phe|Cys|Gly|Thr|Ala|Asn|Thr|Thr|Leu|Lys|Leu|Leu|Leu|465|
|Ala|Tyr|Thr|Pro|Pro|Gly|Ile|Asp|Lys|Pro|Thr|Thr|Arg|Lys|Gln|480|
|Ala|Met|Leu|Gly|Thr|His|Ile|Val|Trp|Asp|Ile|Gly|Leu|Gln|Ser|495|
|Thr|Val|Ser|Leu|Val|Val|Pro|Trp|Val|Ser|Ala|Ser|His|Phe|Arg|510|
|Tyr|Thr|Thr|Pro|Asp|Thr|Tyr|Ser|Met|Ala|Gly|Tyr|Ile|Thr|Cys|525|
|Trp|Tyr|Gln|Thr|Asn|Phe|Val|Phe|Pro|Pro|Asn|Thr|Pro|Asn|Asn|540|
|Ala|Asn|Met|Ile|Cys|Phe|Val|Ser|Gly|Cys|Lys|Asp|Phe|Cys|Leu|555|
|Arg|Met|Ala|Arg|Asp|Thr|Asp|Met|His|Val|Gln|Asn|Val|Pro|Ile|570|
|Thr|Gln|Asn|Pro|Val|Glu|Asn|Tyr|Ile|Asp|Glu|Val|Leu|Asn|Glu|585|
|Val|Leu|Val|Val|Pro|Asn|Ile|Arg|Glu|Ser|His|Pro|Thr|Thr|Ser|600|
|Asn|Ala|Ala|Thr|Ala|Leu|Asp|Ala|Ala|Gly|Thr|Gly|His|Thr|Ser|615|
|Ser|Ile|Gln|Pro|Glu|Asp|Thr|Ile|Glu|Thr|Arg|Tyr|Val|Gln|Thr|630|
|Ser|His|Thr|Arg|Asp|Glu|Met|Ser|Val|Glu|Ser|Phe|Leu|Gly|Arg|645|
|Ser|Gly|Cys|Ile|His|Ile|Ser|Thr|Ile|Thr|Met|Lys|Lys|Glu|Asn|660|
|Tyr|Asn|Asp|His|Asn|Phe|Val|Asp|Trp|Lys|Ile|Thr|Leu|Gln|Glu|675|
|Met|Ala|Gln|Val|Arg|Arg|Lys|Phe|Glu|Met|Phe|Thr|Tyr|Val|Arg|690|
|Phe|Asp|Ser|Glu|Ile|Thr|Leu|Val|Pro|Cys|Ile|Ala|Gly|Arg|Gly|705|
|Glu|Asp|Ile|Gly|His|Ile|Val|Met|Gln|Tyr|Met|Tyr|Val|Pro|Pro|720|
|Gly|Ala|Pro|Val|Pro|Lys|Lys|Arg|Asp|Asp|Tyr|Thr|Trp|Gln|Ser|735|
|Gly|Thr|Asn|Ala|Ser|Val|Phe|Trp|Gln|His|Gly|Gln|Pro|Tyr|Pro|750|
|Arg|Phe|Ser|Leu|Pro|Phe|Leu|Ser|Ile|Ala|Ser|Ala|Tyr|Tyr|Met|765|
|Phe|Tyr|Asp|Gly|Tyr|Asp|Gly|Asp|Lys|Ser|Ser|Ser|Arg|Tyr|Gly|780|
|Val|Ser|Val|Thr|Asn|Asp|Met|Gly|Thr|Leu|Cys|Thr|Arg|Ile|Val|795|
|Thr|Asn|Gln|Gln|Glu|His|Leu|Val|Glu|Val|Thr|Thr|Arg|Val|Tyr|810|
|His|Lys|Ala|Lys|His|Val|Lys|Ala|Trp|Cys|Pro|Arg|Ala|Pro|Arg|825|
|Ala|Val|Pro|Tyr|Thr|His|Ser|Asn|Val|Thr|Asn|Tyr|Lys|Val|Ile|840|

-continued

Asp Gly Glu Pro Thr Leu Phe Ile Lys Ser Arg Ile Asn Leu Thr    855

Thr Ala Gly Pro Ser Asp Met Tyr    863

HRV39 Attn M12
(SEQ ID NO: 86)

Met Gly Ala Gln Val Ser Arg Gln Asn Val Gly Thr His Ser Thr    15

Gln Asn Ser Val Ser Gly Gly Ser Ser Leu Asn Tyr Phe Asn Ile    30

Asn Tyr Phe Lys Asp Ala Ala Ser Ser Gly Ala Ser Lys Leu Glu    45

Phe Ser Gln Asp Pro Ser Lys Phe Thr Asp Pro Val Lys Asp Val    60

Leu Glu Lys Gly Ile Pro Thr Leu Gln Ser Pro Thr Val Glu Ala    75

Cys Gly Tyr Ser Asp Arg Ile Ile Gln Ile Thr Arg Gly Asp Ser    90

Thr Ile Thr Ser Gln Asp Val Ala Asn Ala Val Val Gly Tyr Gly    105

Val Trp Pro His Tyr Leu Thr Ala Asp Ala Ser Ala Ile Asp    120

Lys Pro Thr Gln Pro Asp Thr Ser Ser Asn Arg Phe Tyr Thr Leu    135

Glu Ser Lys Val Trp Lys Arg Asp Ser Lys Gly Trp Trp Trp Lys    150

Leu Pro Asp Ala Leu Lys Asp Met Gly Ile Phe Gly Glu Asn Met    165

Tyr Tyr His Phe Leu Gly Arg Ser Gly Tyr Thr Val His Val Gln    180

Cys Asn Ala Ser Lys Phe His Gln Gly Thr Leu Leu Ile Ala Met    195

Val Pro Glu His Gln Leu Ala Ser Ala Asn Tyr Gly Asn Val Thr    210

Ala Gly Tyr Asn Tyr Thr His Pro Gly Glu Ala Gly Arg Asp Val    225

Gly Gln Gln Arg Ala Leu Ile Gln Lys Gln Pro Ser Asp Asp Asn    240

Trp Leu Asn Phe Asp Gly Thr Leu Leu Gly Asn Leu Leu Ile Phe    255

Pro His Gln Phe Ile Asn Leu Arg Ser Asn Asn Ser Ala Thr Ile    270

Ile Val Pro Tyr Val Asn Ala Val Pro Met Asp Ser Met Leu Arg    285

His Asn Asn Trp Ser Leu Leu Ile Ile Pro Val Ser Pro Leu Asp    300

Ala Asp Thr Ser Ala Thr Ala Ile Val Pro Ile Thr Val Ser Ile    315

Ser Pro Met Phe Ser Glu Phe Ser Gly Ala Arg Ala Arg Pro Ala    330

Ala Ala Thr Gln Gly Leu Pro Val Tyr Met Thr Pro Gly Ser Gly    345

Gln Phe Leu Thr Thr Asp Asp Leu Gln Ser Pro Ser Ala Leu Pro    360

Trp Tyr His Pro Thr Lys Glu Ile Phe Ile Pro Gly Gln Val Arg    375

Asn Leu Ile Glu Met Cys Gln Val Asp Thr Met Ile Pro Ile Asn    390

Asn Thr Ala Glu Arg Ile Gly Asn Val Asn Met Tyr Thr Val Ser    405

Leu Thr Ser Gln Thr Asn Thr Ala Glu Gln Ile Phe Ala Ile Lys    420

Val Asp Ile Ala Ser Gln Pro Leu Ser Ser Thr Leu Ile Gly Glu    435

Ile Ala Ser Tyr Tyr Thr His Trp Thr Gly Ser Leu Arg Phe Ser    450

Phe Met Phe Cys Gly Thr Ala Asn Thr Thr Leu Lys Leu Leu Leu    465

Ala Tyr Thr Pro Pro Gly Ile Asp Lys Pro Thr Thr Arg Lys Gln    480

Ala Met Leu Gly Thr His Ile Val Trp Asp Ile Gly Leu Gln Ser    495

Thr Val Ser Leu Val Val Pro Trp Val Ser Ala Ser His Phe Arg    510

Tyr Thr Thr Pro Asp Thr Tyr Ser Met Ala Gly Tyr Ile Thr Cys    525

Trp Tyr Gln Thr Asn Phe Val Phe Pro Pro Asn Thr Pro Asn Asn    540

Ala Asn Met Ile Cys Phe Val Ser Gly Cys Lys Asp Phe Cys Leu    555

Arg Met Ala Arg Asp Thr Asp Met His Val Gln Asn Val Pro Ile    570

-continued

```
Thr Gln Asn Pro Val Glu Asn Tyr Ile Asp Glu Val Leu Asn Glu      585
Val Leu Val Val Pro Asn Ile Arg Glu Ser His Pro Thr Thr Ser      600
Asn Ala Ala Thr Ala Leu Asp Ala Ala Gly Thr Gly His Thr Ser      615
Ser Ile Gln Pro Glu Asp Thr Ile Glu Thr Arg Tyr Val Gln Thr      630
Ser His Thr Arg Asp Glu Met Ser Val Glu Ser Phe Leu Gly Arg      645
Ser Gly Cys Ile His Ile Ser Thr Ile Thr Met Lys Lys Glu Asn      660
Tyr Asn Asp His Asn Phe Val Asp Trp Lys Ile Thr Leu Gln Glu      675
Met Ala Gln Val Arg Arg Lys Phe Glu Met Phe Thr Tyr Val Arg      690
Phe Asp Ser Glu Ile Thr Leu Val Pro Cys Ile Ala Gly Arg Gly      705
Glu Asp Ile Gly His Ile Val Met Gln Tyr Met Tyr Val Pro Pro      720
Gly Ala Pro Val Pro Lys Lys Arg Asp Asp Tyr Thr Trp Gln Ser      735
Gly Thr Asn Ala Ser Val Phe Trp Gln His Gly Gln Pro Tyr Pro      750
Arg Phe Ser Leu Pro Phe Leu Ser Ile Ala Ser Ala Tyr Tyr Met      765
Phe Tyr Asp Gly Tyr Asp Gly Asp Lys Ser Ser Ser Arg Tyr Gly      780
Val Ser Val Thr Asn Asp Met Gly Thr Leu Cys Thr Arg Ile Val      795
Thr Asn Gln Gln Glu His Leu Val Glu Val Thr Thr Arg Val Tyr      810
His Lys Ala Lys His Val Lys Ala Trp Cys Pro Arg Ala Pro Arg      825
Ala Val Pro Tyr Thr His Ser Asn Val Thr Asn Tyr Lys Val Arg      840
Asp Gly Glu Ala Thr Leu Phe Ile Lys Ser Arg Gln Asn Leu Thr      855
Thr Ala Gly Pro Ser Asp Met Tyr                                  863

HRV39 Attn M13
                                                        (SEQ ID NO: 87)
Met Gly Ala Gln Val Ser Arg Gln Asn Val Gly Thr His Ser Thr       15
Gln Asn Ser Val Ser Gly Gly Ser Ser Leu Asn Tyr Phe Asn Ile       30
Asn Tyr Phe Lys Asp Ala Ala Ser Ser Gly Ala Ser Lys Leu Glu       45
Phe Ser Gln Asp Pro Ser Lys Phe Thr Asp Pro Val Lys Asp Val       60
Leu Glu Lys Gly Ile Pro Thr Leu Gln Ser Pro Thr Val Glu Ala       75
Cys Gly Tyr Ser Asp Arg Ile Ile Gln Ile Thr Arg Gly Asp Ser       90
Thr Ile Thr Ser Gln Asp Val Ala Asn Ala Val Val Gly Tyr Gly      105
Val Trp Pro His Tyr Leu Thr Ala Asp Asp Ala Ser Ala Ile Asp      120
Lys Pro Thr Gln Pro Asp Thr Ser Ser Asn Arg Phe Tyr Thr Leu      135
Glu Ser Lys Val Trp Lys Arg Asp Ser Lys Gly Trp Trp Trp Lys      150
Leu Pro Asp Ala Leu Lys Asp Met Gly Ile Phe Gly Glu Asn Met      165
Tyr Tyr His Phe Leu Gly Arg Ser Gly Tyr Thr Val His Val Gln      180
Cys Asn Ala Ser Lys Phe His Gln Gly Thr Leu Leu Ile Ala Met      195
Val Pro Glu His Gln Leu Ala Ser Ala Asn Tyr Gly Asn Val Thr      210
Ala Gly Tyr Asn Tyr Thr His Pro Gly Glu Ala Gly Arg Asp Val      225
Gly Gln Gln Ile Ala Asn Asn Gln Lys Gln Pro Ser Asp Asp Asn      240
Trp Leu Asn Phe Asp Gly Thr Leu Leu Gly Asn Leu Leu Ile Phe      255
Pro His Gln Phe Ile Asn Leu Arg Ser Asn Asn Ser Ala Thr Ile      270
Ile Val Pro Tyr Val Asn Ala Val Pro Met Asp Ser Met Leu Arg      285
```

```
His Asn Asn Trp Ser Leu Leu Ile Ile Pro Val Ser Pro Leu Asp    300
Ala Asp Thr Ser Ala Thr Ala Ile Val Pro Ile Thr Val Ser Ile    315
Ser Pro Met Phe Ser Glu Phe Ser Gly Ala Arg Ala Arg Pro Ala    330
Ala Ala Thr Gln Gly Leu Pro Val Tyr Met Thr Pro Gly Ser Gly    345
Gln Phe Leu Thr Thr Asp Asp Leu Gln Ser Pro Ser Ala Leu Pro    360
Trp Tyr His Pro Thr Lys Glu Ile Phe Ile Pro Gly Gln Val Arg    375
Asn Leu Ile Glu Met Cys Gln Val Asp Thr Met Ile Pro Ile Asn    390
Asn Thr Asn Glu Ala Ile Gly Asn Val Asn Met Tyr Thr Val Ser    405
Leu Thr Ser Gln Thr Asn Thr Ala Glu Gln Ile Phe Ala Ile Lys    420
Val Asp Ile Ala Ser Gln Pro Leu Ser Ser Thr Leu Ile Gly Glu    435
Ile Ala Ser Tyr Tyr Thr His Trp Thr Gly Ser Leu Arg Phe Ser    450
Phe Met Phe Cys Gly Thr Ala Asn Thr Thr Leu Lys Leu Leu Leu    465
Ala Tyr Thr Pro Pro Gly Ile Asp Lys Pro Thr Thr Arg Lys Gln    480
Ala Met Leu Gly Thr His Ile Val Trp Asp Ile Gly Leu Gln Ser    495
Thr Val Ser Leu Val Val Pro Trp Val Ser Ala Ser His Phe Arg    510
Tyr Thr Thr Pro Asp Thr Tyr Ser Met Ala Gly Tyr Ile Thr Cys    525
Trp Tyr Gln Thr Asn Phe Val Phe Pro Pro Asn Thr Pro Asn Asn    540
Ala Asn Met Ile Cys Phe Val Ser Gly Cys Lys Asp Phe Cys Leu    555
Arg Met Ala Arg Asp Thr Asp Met His Val Gln Asn Val Pro Ile    570
Thr Gln Asn Pro Val Glu Asn Tyr Ile Asp Glu Val Leu Asn Glu    585
Val Leu Val Val Pro Asn Ile Arg Glu Ser His Pro Thr Thr Ser    600
Asn Ala Ala Thr Ala Leu Asp Ala Ala Gly Thr Gly His Thr Ser    615
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Lys Lys Glu Asn    660
Tyr Asn Asp His Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Glu His Leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Ile    840
Asp Gly Glu Pro Thr Leu Phe Ile Lys Leu Arg Ile Asn Leu Thr    855
Thr Ala Gly Pro Ser Asp Met Tyr                                863
HRV39 Attn M14
                                                    (SEQ ID NO: 88)
Met Gly Ala Gln Val Ser Arg Gln Asn Val Gly Thr His Ser Thr     15
```

-continued

```
Gln Asn Ser Val Ser Gly Gly Ser Ser Leu Asn Tyr Phe Asn Ile      30
Asn Tyr Phe Lys Asp Ala Ala Ser Ser Gly Ala Ser Lys Leu Glu      45
Phe Ser Gln Asp Pro Ser Lys Phe Thr Asp Pro Val Lys Asp Val      60
Leu Glu Lys Gly Ile Pro Thr Leu Gln Ser Pro Thr Val Glu Ala      75
Cys Gly Tyr Ser Asp Arg Ile Ile Gln Ile Thr Arg Gly Asp Ser      90
Thr Ile Thr Ser Gln Asp Val Ala Asn Ala Val Val Gly Tyr Gly     105
Val Trp Pro His Tyr Leu Thr Ala Asp Asp Ala Ser Ala Ile Asp     120
Lys Pro Thr Gln Pro Asp Thr Ser Ser Asn Arg Phe Tyr Thr Leu     135
Glu Ser Lys Val Trp Lys Arg Asp Ser Lys Gly Trp Trp Trp Lys     150
Leu Pro Asp Ala Leu Lys Asp Met Gly Ile Phe Gly Glu Asn Met     165
Tyr Tyr His Phe Leu Gly Arg Ser Gly Tyr Thr Val His Val Gln     180
Cys Asn Ala Ser Lys Phe His Gln Gly Thr Leu Leu Ile Ala Met     195
Val Pro Glu His Gln Leu Ala Ser Ala Asn Tyr Gly Asn Val Thr     210
Ala Gly Tyr Asn Tyr Thr His Pro Gly Glu Ala Gly Arg Asp Val     225
Gly Gln Gln Arg Ala Asn Asn Gln Lys Gln Pro Ser Asp Asp Asn     240
Trp Leu Asn Phe Asp Gly Thr Leu Leu Gly Asn Leu Leu Ile Phe     255
Pro His Gln Phe Ile Asn Leu Arg Ser Asn Asn Ser Ala Thr Ile     270
Ile Val Pro Tyr Val Asn Ala Val Pro Met Asp Ser Met Leu Arg     285
His Asn Asn Trp Ser Leu Leu Ile Ile Pro Val Ser Pro Leu Asp     300
Ala Asp Thr Ser Ala Thr Leu Ile Val Pro Ile Thr Val Ser Ile     315
Ser Pro Met Phe Ser Glu Phe Ser Gly Ala Arg Ala Arg Pro Ala     330
Ala Ala Thr Gln Gly Leu Pro Val Tyr Met Thr Pro Gly Ser Gly     345
Gln Phe Leu Thr Thr Asp Asp Leu Gln Ser Pro Ser Ala Leu Pro     360
Trp Tyr His Pro Thr Lys Glu Ile Phe Ile Pro Gly Gln Val Arg     375
Asn Leu Ile Glu Met Cys Gln Val Asp Thr Met Ile Pro Ile Asn     390
Asn Thr Asn Glu Arg Ile Gly Asn Val Asn Met Tyr Thr Val Ser     405
Leu Thr Ser Gln Thr Asn Thr Ala Glu Gln Ile Phe Ala Ile Lys     420
Val Asp Ile Ala Ser Gln Pro Leu Ser Ser Thr Leu Ile Gly Glu     435
Ile Ala Ser Tyr Tyr Thr His Trp Thr Gly Ser Leu Arg Phe Ser     450
Phe Met Phe Cys Gly Thr Ala Asn Thr Thr Leu Lys Leu Leu Leu     465
Ala Tyr Thr Pro Pro Gly Ile Asp Lys Pro Thr Thr Arg Lys Gln     480
Ala Met Leu Gly Thr His Ile Val Trp Asp Ile Gly Leu Gln Ser     495
Thr Val Ser Leu Val Val Pro Trp Val Ser Ala Ser His Phe Arg     510
Tyr Thr Thr Pro Asp Thr Tyr Ser Met Ala Gly Tyr Ile Thr Cys     525
Trp Tyr Gln Thr Asn Phe Val Phe Pro Pro Asn Thr Pro Asn Asn     540
Ala Asn Met Ile Cys Phe Val Ser Gly Cys Lys Asp Phe Cys Leu     555
Arg Met Ala Arg Asp Thr Asp Met His Val Gln Asn Val Pro Ile     570
Thr Gln Asn Pro Val Glu Asn Tyr Ile Asp Glu Val Leu Asn Glu     585
Val Leu Val Val Pro Asn Ile Arg Glu Ser His Pro Thr Thr Ser     600
Asn Ala Ala Thr Ala Leu Asp Ala Ala Gly Thr Gly His Thr Ser     615
```

-continued

```
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Lys Lys Glu Asn    660
Tyr Asn Asp His Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
Gly Ala Pro Val Pro Lys Lys Arg Asp Asp Tyr Thr Trp Gln Ser    735
Gly Thr Asn Ala Ser Val Phe Trp Gln His Gly Gln Pro Tyr Pro    750
Arg Phe Ser Leu Pro Phe Leu Ser Ile Ala Ser Ala Tyr Tyr Met    765
Phe Tyr Asp Gly Tyr Asp Gly Asp Lys Ser Ser Ser Arg Tyr Gly    780
Val Ser Val Thr Asn Asp Met Gly Thr Leu Cys Thr Arg Ile Val    795
Thr Asn Gln Gln Glu His Leu Val Glu Val Thr Thr Arg Val Tyr    810
His Lys Ala Lys His Val Lys Ala Trp Cys Pro Arg Ala Pro Arg    825
Ala Val Pro Tyr Thr His Ser Asn Val Thr Asn Tyr Lys Val Arg    840
Asp Gly Glu Pro Thr Leu Phe Ile Lys Ser Arg Glu Asn Leu Thr    855
Thr Ala Gly Pro Ser Asp Met Tyr                                863

HRV39 Attn M15
                                                    (SEQ ID NO: 89)
Met Gly Ala Gln Val Ser Arg Gln Asn Val Gly Thr His Ser Thr     15
Gln Asn Ser Val Ser Gly Gly Ser Ser Leu Asn Tyr Phe Asn Ile     30
Asn Tyr Phe Lys Asp Ala Ala Ser Ser Gly Ala Ser Lys Leu Glu     45
Phe Ser Gln Asp Pro Ser Lys Phe Thr Asp Pro Val Lys Asp Val     60
Leu Glu Lys Gly Ile Pro Thr Leu Gln Ser Pro Thr Val Glu Ala     75
Cys Gly Tyr Ser Asp Arg Ile Ile Gln Ile Thr Arg Gly Asp Ser     90
Thr Ile Thr Ser Gln Asp Val Ala Asn Ala Val Val Gly Tyr Gly    105
Val Trp Pro His Tyr Leu Thr Ala Asp Asp Ala Ser Ala Ile Asp    120
Lys Pro Thr Gln Pro Asp Thr Ser Ser Asn Arg Phe Tyr Thr Leu    135
Glu Ser Lys Val Trp Lys Ala Gly Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Arg Ala Asn Asn Gln Lys Gln Pro Ser Asp Asp Asn    240
Trp Leu Asn Phe Asp Gly Thr Leu Leu Gly Asn Leu Leu Ile Phe    255
Pro His Gln Phe Ile Asn Leu Arg Ser Asn Asn Ser Ala Thr Ile    270
Ile Val Pro Tyr Val Asn Ala Val Pro Met Asp Ser Met Leu Arg    285
His Asn Asn Trp Ser Leu Leu Ile Ile Pro Val Ser Pro Leu Asp    300
Ala Asp Thr Ser Ala Thr Ala Ile Val Pro Ile Thr Val Ser Ile    315
Ser Pro Met Phe Ser Glu Phe Ser Gly Ala Arg Ala Arg Pro Ala    330
Ala Ala Thr Gln Gly Leu Pro Val Tyr Met Thr Pro Gly Ser Gly    345
```

-continued

```
Gln Phe Leu Thr Thr Asp Asp Leu Gln Ser Pro Ser Ala Leu Pro      360
Trp Tyr His Pro Thr Lys Glu Ile Phe Ile Pro Gly Gln Val Arg      375
Asn Leu Ile Glu Met Cys Gln Val Asp Thr Met Ile Pro Ile Asn      390
Asn Thr Asn Glu Arg Ile Gly Asn Val Asn Met Tyr Thr Val Ser      405
Leu Thr Ser Gln Thr Asn Thr Ala Glu Gln Ile Phe Ala Ile Lys      420
Val Asp Ile Ala Ser Gln Pro Leu Ser Ser Thr Leu Ile Gly Glu      435
Ile Ala Ser Tyr Tyr Thr His Trp Thr Gly Ser Leu Arg Phe Ser      450
Phe Met Phe Cys Gly Thr Ala Asn Thr Thr Leu Lys Leu Leu Leu      465
Ala Tyr Thr Pro Pro Gly Ile Asp Lys Pro Thr Thr Arg Lys Gln      480
Ala Met Leu Gly Thr His Ile Val Trp Asp Ile Gly Leu Gln Ser      495
Thr Val Ser Leu Val Val Pro Trp Val Ser Ala Ser His Phe Arg      510
Tyr Thr Thr Pro Asp Thr Tyr Ser Met Ala Gly Tyr Ile Thr Cys      525
Trp Tyr Gln Thr Asn Phe Val Phe Pro Pro Asn Thr Pro Asn Asn      540
Ala Asn Met Ile Cys Phe Val Ser Gly Cys Lys Asp Phe Cys Leu      555
Arg Met Ala Arg Asp Thr Asp Met His Val Gln Asn Val Pro Ile      570
Thr Gln Asn Pro Val Glu Asn Tyr Ile Asp Glu Val Leu Asn Glu      585
Val Leu Val Val Pro Asn Ile Arg Glu Ser His Pro Thr Thr Ser      600
Asn Ala Ala Thr Ala Leu Asp Ala Ala Gly Thr Gly His Thr Ser      615
Ser Ile Gln Pro Glu Asp Thr Ile Glu Thr Arg Tyr Val Gln Thr      630
Ser His Thr Arg Asp Glu Met Ser Val Glu Ser Phe Leu Gly Arg      645
Ser Gly Cys Ile His Ile Ser Thr Ile Thr Met Lys Lys Glu Asn      660
Tyr Asn Asp His Asn Phe Val Asp Trp Lys Ile Thr Leu Gln Glu      675
Met Ala Gln Val Arg Arg Lys Phe Glu Met Phe Thr Tyr Val Arg      690
Phe Asp Ser Glu Ile Thr Leu Val Pro Cys Ile Ala Gly Arg Gly      705
Glu Asp Ile Gly His Ile Val Met Gln Tyr Met Tyr Val Pro Pro      720
Gly Ala Pro Val Pro Lys Lys Arg Asp Asp Tyr Thr Trp Gln Ser      735
Gly Thr Asn Ala Ser Val Phe Trp Gln His Gly Gln Pro Tyr Pro      750
Arg Phe Ser Leu Pro Phe Leu Ser Ile Ala Ser Ala Tyr Tyr Met      765
Phe Tyr Asp Gly Tyr Asp Gly Asp Lys Ser Ser Ser Arg Tyr Gly      780
Val Ser Val Thr Asn Asp Met Gly Thr Leu Cys Thr Arg Ile Val      795
Thr Asn Gln Gln Glu His Leu Val Glu Val Thr Thr Arg Val Tyr      810
His Lys Ala Lys His Val Lys Ala Trp Cys Pro Arg Ala Pro Arg      825
Ala Val Pro Tyr Thr His Ser Asn Val Thr Asn Tyr Lys Val Arg      840
Asp Gly Glu Pro Thr Leu Phe Ile Lys Ser Arg Glu Asn Leu Thr      855
Thr Ala Gly Pro Ser Asp Met Tyr                                  863

HRV39 Attn M16
                                                    (SEQ ID NO: 90)
Met Gly Ala Gln Val Ser Arg Gln Asn Val Gly Thr His Ser Thr       15
Gln Asn Ser Val Ser Gly Gly Ser Ser Leu Asn Tyr Phe Asn Ile       30
Asn Tyr Phe Lys Asp Ala Ala Ser Ser Gly Ala Ser Lys Leu Glu       45
Phe Ser Gln Asp Pro Ser Lys Phe Thr Asp Pro Val Lys Asp Val       60
```

-continued

```
Leu Glu Lys Gly Ile Pro Thr Leu Gln Ser Pro Thr Val Glu Ala         75
Cys Gly Tyr Ser Asp Arg Ile Ile Gln Ile Thr Arg Gly Asp Ser         90
Thr Ile Thr Ser Gln Asp Val Ala Asn Ala Val Val Gly Tyr Gly        105
Val Trp Pro His Tyr Leu Thr Ala Asp Asp Ala Ser Ala Ile Asp        120
Lys Pro Thr Gln Pro Asp Thr Ser Ser Asn Arg Phe Tyr Thr Leu        135
Glu Ser Lys Val Trp Lys Ala Gly Ser Lys Gly Trp Trp Trp Lys        150
Leu Pro Asp Ala Leu Lys Asp Met Gly Ile Phe Gly Glu Asn Met        165
Tyr Tyr His Phe Leu Gly Arg Ser Gly Tyr Thr Val His Val Gln        180
Cys Asn Ala Ser Lys Phe His Gln Gly Thr Leu Leu Ile Ala Met        195
Val Pro Glu His Gln Leu Ala Ser Ala Asn Tyr Gly Asn Val Thr        210
Ala Gly Tyr Asn Tyr Thr His Pro Gly Glu Ala Gly Arg Asp Val        225
Gly Gln Gln Arg Ala Asn Asn Gln Lys Gln Pro Ser Asp Asp Asn        240
Trp Leu Asn Phe Asp Gly Thr Leu Leu Gly Asn Leu Leu Ile Phe        255
Pro His Gln Phe Ile Asn Leu Arg Ser Asn Asn Ser Ala Thr Ile        270
Ile Val Pro Tyr Val Asn Ala Val Pro Met Asp Ser Met Leu Arg        285
His Asn Asn Trp Ser Leu Leu Ile Ile Pro Val Ser Pro Leu Asp        300
Ala Asp Thr Ser Gly Thr Leu Ile Val Pro Ile Thr Val Ser Ile        315
Ser Pro Met Phe Ser Glu Phe Ser Gly Ala Arg Ala Arg Pro Ala        330
Ala Ala Thr Gln Gly Leu Pro Val Tyr Met Thr Pro Gly Ser Gly        345
Gln Phe Leu Thr Thr Asp Asp Leu Gln Ser Pro Ser Ala Leu Pro        360
Trp Tyr His Pro Thr Lys Glu Ile Phe Ile Pro Gly Gln Val Arg        375
Asn Leu Ile Glu Met Cys Gln Val Asp Thr Met Ile Pro Ile Asn        390
Asn Thr Asn Glu Arg Ile Gly Asn Val Asn Met Tyr Thr Val Ser        405
Leu Thr Ser Gln Thr Asn Thr Ala Glu Gln Ile Phe Ala Ile Lys        420
Val Asp Ile Ala Ser Gln Pro Leu Ser Ser Thr Leu Ile Gly Glu        435
Ile Ala Ser Tyr Tyr Thr His Trp Thr Gly Ser Leu Arg Phe Ser        450
Phe Met Phe Cys Gly Thr Ala Asn Thr Thr Leu Lys Leu Leu Leu        465
Ala Tyr Thr Pro Pro Gly Ile Asp Lys Pro Thr Thr Arg Lys Gln        480
Ala Met Leu Gly Thr His Ile Val Trp Asp Ile Gly Leu Gln Ser        495
Thr Val Ser Leu Val Val Pro Trp Val Ser Ala Ser His Phe Arg        510
Tyr Thr Thr Pro Asp Thr Tyr Ser Met Ala Gly Tyr Ile Thr Cys        525
Trp Tyr Gln Thr Asn Phe Val Phe Pro Pro Asn Thr Pro Asn Asn        540
Ala Asn Met Ile Cys Phe Val Ser Gly Cys Lys Asp Phe Cys Leu        555
Arg Met Ala Arg Asp Thr Asp Met His Val Gln Asn Val Pro Ile        570
Thr Gln Asn Pro Val Glu Asn Tyr Ile Asp Glu Val Leu Asn Glu        585
Val Leu Val Val Pro Asn Ile Arg Glu Ser His Pro Thr Thr Ser        600
Asn Ala Ala Thr Ala Leu Asp Ala Ala Gly Thr Gly His Thr Ser        615
Ser Ile Gln Pro Glu Asp Thr Ile Glu Thr Arg Tyr Val Gln Thr        630
Ser His Thr Arg Asp Glu Met Ser Val Glu Ser Phe Leu Gly Arg        645
Ser Gly Cys Ile His Ile Ser Thr Ile Thr Met Lys Lys Glu Asn        660
Tyr Asn Asp His Asn Phe Val Asp Trp Lys Ile Thr Leu Gln Glu        675
```

-continued

```
Met Ala Gln Val Arg Arg Lys Phe Glu Met Phe Thr Tyr Val Arg      690
Phe Asp Ser Glu Ile Thr Leu Val Pro Cys Ile Ala Gly Arg Gly      705
Glu Asp Ile Gly His Ile Val Met Gln Tyr Met Tyr Val Pro Pro      720
Gly Ala Pro Val Pro Lys Lys Arg Asp Asp Tyr Thr Trp Gln Ser      735
Gly Thr Asn Ala Ser Val Phe Trp Gln His Gly Gln Pro Tyr Pro      750
Arg Phe Ser Leu Pro Phe Leu Ser Ile Ala Ser Ala Tyr Tyr Met      765
Phe Tyr Asp Gly Tyr Asp Gly Asp Lys Ser Ser Ser Arg Tyr Gly      780
Val Ser Val Thr Asn Asp Met Gly Thr Leu Cys Thr Arg Ile Val      795
Thr Asn Gln Gln Glu His Leu Val Glu Val Thr Thr Arg Val Tyr      810
His Lys Ala Lys His Val Lys Ala Trp Cys Pro Arg Ala Pro Arg      825
Ala Val Pro Tyr Thr His Ser Asn Val Thr Asn Tyr Lys Val Arg      840
Asp Gly Glu Pro Thr Leu Phe Ile Lys Ser Arg Glu Asn Leu Thr      855
Thr Ala Gly Pro Ser Asp Met Tyr                                  863
```

HRV39 Attn M17

(SEQ ID NO: 91)

```
Met Gly Ala Gln Val Ser Arg Gln Asn Val Gly Thr His Ser Thr       15
Gln Asn Ser Val Ser Gly Gly Ser Ser Leu Asn Tyr Phe Asn Ile       30
Asn Tyr Phe Lys Asp Ala Ala Ser Ser Gly Ala Ser Lys Leu Glu       45
Phe Ser Gln Asp Pro Ser Lys Phe Thr Asp Pro Val Lys Asp Val       60
Leu Glu Lys Gly Ile Pro Thr Leu Gln Ser Pro Thr Val Glu Ala       75
Cys Gly Tyr Ser Asp Arg Ile Ile Gln Ile Thr Arg Gly Asp Ser       90
Thr Ile Thr Ser Gln Asp Val Ala Asn Ala Val Val Gly Tyr Gly      105
Val Trp Pro His Tyr Leu Thr Ala Asp Asp Ala Ser Ala Ile Asp      120
Lys Pro Thr Gln Pro Asp Thr Ser Ser Asn Arg Phe Tyr Thr Leu      135
Glu Ser Lys Val Trp Lys Arg Asp Ser Lys Gly Trp Trp Trp Lys      150
Leu Pro Asp Ala Leu Lys Asp Met Gly Ile Phe Gly Glu Asn Met      165
Tyr Tyr His Phe Leu Gly Arg Ser Gly Tyr Thr Val His Val Gln      180
Cys Asn Ala Ser Lys Phe His Gln Gly Thr Leu Leu Ile Ala Met      195
Val Pro Glu His Gln Leu Ala Ser Ala Asn Tyr Gly Asn Val Thr      210
Ala Gly Tyr Asn Tyr Thr His Pro Gly Glu Ala Gly Arg Asp Val      225
Gly Gln Gln Arg Ala Leu Ile Gln Lys Gln Pro Ser Asp Asp Asn      240
Trp Leu Asn Phe Asp Gly Thr Leu Leu Gly Asn Leu Leu Ile Phe      255
Pro His Gln Phe Ile Asn Leu Arg Ser Asn Asn Ser Ala Thr Ile      270
Ile Val Pro Tyr Val Asn Ala Val Pro Met Asp Ser Met Leu Arg      285
His Asn Asn Trp Ser Leu Leu Ile Ile Pro Val Ser Pro Leu Asp      300
Ala Asp Thr Ser Ala Thr Leu Ile Val Pro Ile Thr Val Ser Ile      315
Ser Pro Met Phe Ser Glu Phe Ser Gly Ala Arg Ala Arg Pro Ala      330
Ala Ala Thr Gln Gly Leu Pro Val Tyr Met Thr Pro Gly Ser Gly      345
Gln Phe Leu Thr Thr Asp Asp Leu Gln Ser Pro Ser Ala Leu Pro      360
Trp Tyr His Pro Thr Lys Glu Ile Phe Ile Pro Gly Gln Val Arg      375
Asn Leu Ile Glu Met Cys Gln Val Asp Thr Met Ile Pro Ile Asn      390
```

-continued

```
Asn Thr Ala Glu Arg Ile Gly Asn Val Asn Met Tyr Thr Val Ser      405
Leu Thr Ser Gln Thr Asn Thr Ala Glu Gln Ile Phe Ala Ile Lys      420
Val Asp Ile Ala Ser Gln Pro Leu Ser Ser Thr Leu Ile Gly Glu      435
Ile Ala Ser Tyr Tyr Thr His Trp Thr Gly Ser Leu Arg Phe Ser      450
Phe Met Phe Cys Gly Thr Ala Asn Thr Thr Leu Lys Leu Leu Leu      465
Ala Tyr Thr Pro Pro Gly Ile Asp Lys Pro Thr Thr Arg Lys Gln      480
Ala Met Leu Gly Thr His Ile Val Trp Asp Ile Gly Leu Gln Ser      495
Thr Val Ser Leu Val Val Pro Trp Val Ser Ala Ser His Phe Arg      510
Tyr Thr Thr Pro Asp Thr Tyr Ser Met Ala Gly Tyr Ile Thr Cys      525
Trp Tyr Gln Thr Asn Phe Val Phe Pro Pro Asn Thr Pro Asn Asn      540
Ala Asn Met Ile Cys Phe Val Ser Gly Cys Lys Asp Phe Cys Leu      555
Arg Met Ala Arg Asp Thr Asp Met His Val Gln Asn Val Pro Ile      570
Thr Gln Asn Pro Val Glu Asn Tyr Ile Asp Glu Val Leu Asn Glu      585
Val Leu Val Val Pro Asn Ile Arg Glu Ser His Pro Thr Thr Ser      600
Asn Ala Ala Thr Ala Leu Asp Ala Ala Gly Thr Gly His Thr Ser      615
Ser Ile Gln Pro Glu Asp Thr Ile Glu Thr Arg Tyr Val Gln Thr      630
Ser His Thr Arg Asp Glu Met Ser Val Glu Ser Phe Leu Gly Arg      645
Ser Gly Cys Ile His Ile Ser Thr Ile Thr Met Leu Ile Glu Asn      660
Tyr Asn Asp Ala Asn Phe Val Asp Trp Lys Ile Thr Leu Gln Glu      675
Met Ala Gln Val Arg Arg Lys Phe Glu Met Phe Thr Tyr Val Arg      690
Phe Asp Ser Glu Ile Thr Leu Val Pro Cys Ile Ala Gly Arg Gly      705
Glu Asp Ile Gly His Ile Val Met Gln Tyr Met Tyr Val Pro Pro      720
Gly Ala Pro Val Pro Lys Lys Arg Asp Asp Tyr Thr Trp Gln Ser      735
Gly Thr Asn Ala Ser Val Phe Trp Gln His Gly Gln Pro Tyr Pro      750
Arg Phe Ser Leu Pro Phe Leu Ser Ile Ala Ser Ala Tyr Tyr Met      765
Phe Tyr Asp Gly Tyr Asp Gly Asp Lys Ser Ser Ser Arg Tyr Gly      780
Val Ser Val Thr Asn Asp Met Gly Thr Leu Cys Thr Arg Ile Val      795
Thr Asn Gln Gln Glu His Leu Val Glu Val Thr Thr Arg Val Tyr      810
His Lys Ala Lys His Val Lys Ala Trp Cys Pro Arg Ala Pro Arg      825
Ala Val Pro Tyr Thr His Ser Asn Val Thr Asn Tyr Lys Val Arg      840
Asp Gly Glu Ala Thr Leu Phe Ile Lys Ser Arg Glu Asn Leu Thr      855
Thr Ala Gly Pro Ser Asp Met Tyr                                  863
```

HRV39 Attn M18

(SEQ ID NO: 92)
```
Met Gly Ala Gln Val Ser Arg Gln Asn Val Gly Thr His Ser Thr       15
Gln Asn Ser Val Ser Gly Gly Ser Ser Leu Asn Tyr Phe Asn Ile       30
Asn Tyr Phe Lys Asp Ala Ala Ser Ser Gly Ala Ser Lys Leu Glu       45
Phe Ser Gln Asp Pro Ser Lys Phe Thr Asp Pro Val Lys Asp Val       60
Leu Glu Lys Gly Ile Pro Thr Leu Gln Ser Pro Thr Val Glu Ala       75
Cys Gly Tyr Ser Asp Arg Ile Ile Gln Ile Thr Arg Gly Asp Ser       90
Thr Ile Thr Ser Gln Asp Val Ala Asn Ala Val Val Gly Tyr Gly      105
Val Trp Pro His Tyr Leu Thr Ala Asp Asp Ala Ser Ala Ile Asp      120
```

```
Lys Pro Thr Gln Pro Asp Thr Ser Ser Asn Arg Phe Tyr Thr Leu    135
Glu Ser Lys Val Trp Lys Ala Gly Ser Lys Gly Trp Trp Trp Lys    150
Leu Pro Asp Ala Leu Lys Asp Met Gly Ile Phe Gly Glu Asn Met    165
Tyr Tyr His Phe Leu Gly Arg Ser Gly Tyr Thr Val His Val Gln    180
Cys Asn Ala Ser Lys Phe His Gln Gly Thr Leu Leu Ile Ala Met    195
Val Pro Glu His Gln Leu Ala Ser Ala Asn Tyr Gly Asn Val Thr    210
Ala Gly Tyr Asn Tyr Thr His Pro Gly Glu Ala Gly Arg Asp Val    225
Gly Gln Gln Ile Ala Asn Asn Gln Lys Gln Pro Ser Asp Asp Asn    240
Trp Leu Asn Phe Asp Gly Thr Leu Leu Gly Asn Leu Leu Ile Phe    255
Pro His Gln Phe Ile Asn Leu Arg Ser Asn Asn Ser Ala Thr Ile    270
Ile Val Pro Tyr Val Asn Ala Val Pro Met Asp Ser Met Leu Arg    285
His Asn Asn Trp Ser Leu Leu Ile Ile Pro Val Ser Pro Leu Asp    300
Ala Asp Thr Ser Ala Thr Ala Ile Val Pro Ile Thr Val Ser Ile    315
Ser Pro Met Phe Ser Glu Phe Ser Gly Ala Arg Ala Arg Pro Ala    330
Ala Ala Thr Gln Gly Leu Pro Val Tyr Met Thr Pro Gly Ser Gly    345
Gln Phe Leu Thr Thr Asp Asp Leu Gln Ser Pro Ser Ala Leu Pro    360
Trp Tyr His Pro Thr Lys Glu Ile Phe Ile Pro Gly Gln Val Arg    375
Asn Leu Ile Glu Met Cys Gln Val Asp Thr Met Ile Pro Ile Asn    390
Asn Thr Asn Glu Ala Ile Gly Asn Val Asn Met Tyr Thr Val Ser    405
Leu Thr Ser Gln Thr Asn Thr Ala Glu Gln Ile Phe Ala Ile Lys    420
Val Asp Ile Ala Ser Gln Pro Leu Ser Ser Thr Leu Ile Gly Glu    435
Ile Ala Ser Tyr Tyr Thr His Trp Thr Gly Ser Leu Arg Phe Ser    450
Phe Met Phe Cys Gly Thr Ala Asn Thr Thr Leu Lys Leu Leu Leu    465
Ala Tyr Thr Pro Pro Gly Ile Asp Lys Pro Thr Thr Arg Lys Gln    480
Ala Met Leu Gly Thr His Ile Val Trp Asp Ile Gly Leu Gln Ser    495
Thr Val Ser Leu Val Val Pro Trp Val Ser Ala Ser His Phe Arg    510
Tyr Thr Thr Pro Asp Thr Tyr Ser Met Ala Gly Tyr Ile Thr Cys    525
Trp Tyr Gln Thr Asn Phe Val Phe Pro Pro Asn Thr Pro Asn Asn    540
Ala Asn Met Ile Cys Phe Val Ser Gly Cys Lys Asp Phe Cys Leu    555
Arg Met Ala Arg Asp Thr Asp Met His Val Gln Asn Val Pro Ile    570
Thr Gln Asn Pro Val Glu Asn Tyr Ile Asp Glu Val Leu Asn Glu    585
Val Leu Val Val Pro Asn Ile Arg Glu Ser His Pro Thr Thr Ser    600
Asn Ala Ala Thr Ala Leu Asp Ala Ala Gly Thr Gly His Thr Ser    615
Ser Ile Gln Pro Glu Asp Thr Ile Glu Thr Arg Tyr Val Gln Thr    630
Ser His Thr Arg Asp Glu Met Ser Val Glu Ser Phe Leu Gly Arg    645
Ser Gly Cys Ile His Ile Ser Thr Ile Thr Met Leu Ile Glu Asn    660
Tyr Asn Asp Ala Asn Phe Val Asp Trp Lys Ile Thr Leu Gln Glu    675
Met Ala Gln Val Arg Arg Lys Phe Glu Met Phe Thr Tyr Val Arg    690
Phe Asp Ser Glu Ile Thr Leu Val Pro Cys Ile Ala Gly Arg Gly    705
Glu Asp Ile Gly His Ile Val Met Gln Tyr Met Tyr Val Pro Pro    720
```

```
Gly Ala Pro Val Pro Lys Lys Arg Asp Asp Tyr Thr Trp Gln Ser    735

Gly Thr Asn Ala Ser Val Phe Trp Gln His Gly Gln Pro Tyr Pro    750

Arg Phe Ser Leu Pro Phe Leu Ser Ile Ala Ser Ala Tyr Tyr Met    765

Phe Tyr Asp Gly Tyr Asp Gly Asp Lys Ser Ser Ser Arg Tyr Gly    780

Val Ser Val Thr Asn Asp Met Gly Thr Leu Cys Thr Arg Ile Val    795

Thr Asn Gln Gln Ala His Leu Val Glu Val Thr Thr Arg Val Tyr    810

His Lys Ala Lys His Val Lys Ala Trp Cys Pro Arg Ala Pro Arg    825

Ala Val Pro Tyr Thr His Ser Asn Val Thr Asn Tyr Lys Val Ile    840

Asp Gly Glu Pro Thr Leu Phe Ile Lys Leu Arg Ile Asn Leu Thr    855

Thr Ala Gly Pro Ser Asp Met Tyr                                863
```

---

What is claimed is:

1. A polypeptide or virus comprising an epitope of a human rhinovirus comprising an amino acid sequence selected from the group consisting of SEQ ID NOs: 16-33, 35, 37, 39, 41, 45, 47, 49, 65-73, 75-91 and 92.

2. A fusion protein comprising the polypeptide of claim 1.

3. A virus-like particle (VLP) comprising the polypeptide of claim 1.

4. The VLP of claim 3, further comprising a toxic or therapeutic molecule.

5. A recombinant virus comprising the polypeptide of claim 1.

6. The recombinant virus of claim 5, further comprising a toxic or therapeutic molecule.

7. An immunogenic composition comprising the polypeptide or virus of claim 1.

8. The immunogenic composition of claim 7, further comprising an adjuvant.

9. The immunogenic composition of claim 8, wherein the adjuvant is selected from a group consisting of an aluminum salt, a salt of calcium, a salt of iron, a salt of zinc, an insoluble suspension of acylated tyrosine, acetylated sugars, cationically or anionically derived polysaccharides, and polyphosphazenes.

10. A pharmaceutical composition comprising the polypeptide or virus of claim 1.

* * * * *